US011897889B2

(12) United States Patent
Zhou et al.

(10) Patent No.: US 11,897,889 B2
(45) Date of Patent: Feb. 13, 2024

(54) PROCESS AND INTERMEDIATES FOR PREPARING A JAK1 INHIBITOR

(71) Applicant: Incyte Corporation, Wilmington, DE (US)

(72) Inventors: Jiacheng Zhou, Newark, DE (US); Shili Chen, Newark, DE (US); Pingli Liu, Wilmington, DE (US); David J. Meloni, Bear, DE (US); Yongchun Pan, Wilmington, DE (US); Naijing Su, Hockessin, DE (US); Michael Xia, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/404,461

(22) Filed: Aug. 17, 2021

(65) Prior Publication Data
US 2022/0056034 A1 Feb. 24, 2022

Related U.S. Application Data

(60) Provisional application No. 63/067,062, filed on Aug. 18, 2020.

(51) Int. Cl.
*C07D 487/04* (2006.01)
*C07D 205/04* (2006.01)
*C07D 401/14* (2006.01)

(52) U.S. Cl.
CPC ......... *C07D 487/04* (2013.01); *C07D 205/04* (2013.01); *C07D 401/14* (2013.01)

(58) Field of Classification Search
CPC ... C07D 487/04; C07D 205/04; C07D 401/14
See application file for complete search history.

(56) References Cited

U.S. PATENT DOCUMENTS

| | | | |
|---|---|---|---|
| 7,335,667 B2 | 2/2008 | Rodgers et al. |
| 7,598,257 B2 | 10/2009 | Rodgers et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,445,488 B2 | 5/2013 | Rodgers et al. |
| 8,486,902 B2 | 7/2013 | Rodgers et al. |
| 8,530,485 B2 | 9/2013 | Rodgers et al. |
| 8,541,425 B2 | 9/2013 | Rodgers et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,883,806 B2 | 11/2014 | Zhou |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,443 B2 | 3/2015 | Liu et al. |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 9,193,733 B2 | 11/2015 | Rodgers et al. |
| 9,206,187 B2 | 12/2015 | Rodgers et al. |
| 9,216,984 B2 | 12/2015 | Li et al. |
| 9,221,845 B2 | 12/2015 | Cao |
| 9,249,145 B2 | 2/2016 | Rodgers et al. |
| 9,290,506 B2 | 3/2016 | Zhou et al. |
| 9,334,274 B2 | 5/2016 | Rodgers et al. |
| 9,359,358 B2 | 6/2016 | Rodgers et al. |
| 9,376,439 B2 | 6/2016 | Rodgers et al. |
| 9,382,231 B2 | 7/2016 | Li et al. |
| 9,464,088 B2 | 10/2016 | Huang et al. |
| 9,487,521 B2 | 11/2016 | Zhou et al. |
| 9,512,161 B2 | 12/2016 | Rodgers et al. |
| 9,580,419 B2 | 2/2017 | Rodgers et al. |
| 9,611,269 B2 | 4/2017 | Yao et al. |
| 9,623,029 B2 | 4/2017 | Li et al. |
| 9,662,335 B2 | 5/2017 | Rodgers et al. |
| 9,714,233 B2 | 7/2017 | Liu et al. |
| 9,718,834 B2 | 8/2017 | Zhou et al. |

(Continued)

FOREIGN PATENT DOCUMENTS

| | | |
|---|---|---|
| CN | 2928286 | 10/2016 |
| CN | 106397443 | 2/2017 |

(Continued)

OTHER PUBLICATIONS

Aleksanyan et al., "Synthesis and transformations of novel formyl-substituted quinolines," Heterocycl Commun., Jan. 1, 2011, 17(3-4):105-110.
Arnold, "Synthetic Reactions of Dimethyl Formamide," Collect Czech Chem Comm., 1963, 28:863-868 (English Abstract).
Arnold, "Synthetic reactions of dimethylformamide. XV. Synthesis of symmetrical tetraformylethane," Collect Czech Chem Comm., 1962, 27:2993-2995.
Berge et al., "Pharmaceutical Salts," Journal of Pharmaceutical Science, 1977, 66:1-19.
Blume-Jensen P. et al., "Oncogenic kinase signalling," Nature, 2001, 411(6835):355-365.
Borrell et al., "Design and synthesis of two pyrazole libraries based on o-hydroxyacetophenones," Mol Divers., 2004, 8(2):147-157.
Bredereck et al., "Reactions of Activated Methyl Groups Attached to Heterocycles," Agnew Chem Internat Edit., 1963, 2(12):738.

(Continued)

*Primary Examiner* — Rebecca L Anderson
(74) *Attorney, Agent, or Firm* — Fish & Richardson P.C.

(57) ABSTRACT

The present invention is related to processes for preparing itacitinib, or a salt thereof, and related synthetic intermediates related thereto.

69 Claims, 9 Drawing Sheets

(56) References Cited

U.S. PATENT DOCUMENTS

| | | |
|---|---|---|
| 9,802,957 B2 | 10/2017 | Zhou et al. |
| 9,814,722 B2 | 11/2017 | Rodgers et al. |
| 9,879,010 B2 | 1/2018 | Rodgers et al. |
| 9,908,888 B2 | 3/2018 | Zhou et al. |
| 9,926,301 B2 | 3/2018 | Li et al. |
| 9,974,790 B2 | 5/2018 | Rodgers et al. |
| 9,999,619 B2 | 6/2018 | Huang et al. |
| 10,016,429 B2 | 7/2018 | Rodgers et al. |
| 10,166,191 B2 | 1/2019 | Ni et al. |
| 10,364,248 B2 | 7/2019 | Zhou et al. |
| 10,398,699 B2 | 9/2019 | Rodgers et al. |
| 10,428,104 B2 | 10/2019 | Tatlock et al. |
| 10,435,392 B2 | 10/2019 | Li et al. |
| 10,450,325 B2 | 10/2019 | Zhou et al. |
| 10,463,667 B2 | 11/2019 | Rodgers et al. |
| 10,513,522 B2 | 12/2019 | Yao et al. |
| 10,562,904 B2 | 2/2020 | Zhang et al. |
| 10,610,530 B2 | 4/2020 | Li et al. |
| 10,639,310 B2 | 5/2020 | Rodgers et al. |
| 10,640,506 B2 | 5/2020 | Rodgers et al. |
| 10,695,337 B2 | 6/2020 | Huang et al. |
| 10,758,543 B2 | 9/2020 | Parikh et al. |
| 10,766,900 B2 | 9/2020 | Lai |
| 10,869,870 B2 | 12/2020 | Parikh et al. |
| 10,874,616 B2 | 12/2020 | Ni et al. |
| 10,899,736 B2 | 1/2021 | Wang et al. |
| 10,975,085 B2 | 4/2021 | Zhou et al. |
| 11,001,571 B2 | 5/2021 | Li et al. |
| 11,213,528 B2 | 1/2022 | Li et al. |
| 11,214,573 B2 | 1/2022 | Yao et al. |
| 11,219,624 B2 | 1/2022 | Parikh et al. |
| 11,285,140 B2 | 3/2022 | Huang et al. |
| 11,331,320 B2 | 5/2022 | Rodgers et al. |
| 11,337,927 B2 | 5/2022 | Ni et al. |
| 2007/0135461 A1 | 6/2007 | Rodgers et al. |
| 2008/0312259 A1 | 12/2008 | Rodgers et al. |
| 2009/0233903 A1 | 9/2009 | Rodgers et al. |
| 2010/0190981 A1 | 7/2010 | Zhou et al. |
| 2011/0224190 A1 | 9/2011 | Huang et al. |
| 2012/0022058 A1 | 1/2012 | Arhancet et al. |
| 2013/0060026 A1 | 3/2013 | Zhou et al. |
| 2014/0256941 A1 | 9/2014 | Liu et al. |
| 2015/0087632 A1 | 3/2015 | Rodgers et al. |
| 2015/0065484 A1 | 10/2015 | Yeleswaram et al. |
| 2019/0023712 A1 | 1/2019 | Zhang et al. |
| 2019/0169200 A1 | 6/2019 | Pan et al. |
| 2019/0211021 A1 | 7/2019 | Zhang et al. |
| 2019/0233392 A1 | 8/2019 | Wang et al. |
| 2021/0238168 A1 | 8/2021 | Li et al. |
| 2022/0056035 A1 | 2/2022 | Zhou et al. |
| 2023/0059389 A1 | 2/2023 | Zhou et al. |

FOREIGN PATENT DOCUMENTS

| | | |
|---|---|---|
| CN | 107759601 | 3/2018 |
| CN | 107759623 | 3/2018 |
| CN | 109651424 | 4/2019 |
| CN | 110003216 | 7/2019 |
| CN | 110724145 | 1/2020 |
| CN | 113480546 | 10/2021 |
| EP | 434940 | 7/1991 |
| EP | 2398774 | 12/2011 |
| EP | 3262057 | 1/2018 |
| EP | 3398952 | 11/2018 |
| GB | 812366 | 4/1959 |
| IN | 2015CH05639 | 4/2017 |
| IN | 201641026603 | 2/2018 |
| WO | WO 2004/021979 | 3/2004 |
| WO | WO 2005/116035 | 12/2005 |
| WO | WO 2007/012953 | 2/2007 |
| WO | WO 2007/092213 | 8/2007 |
| WO | WO 2009/016460 | 2/2009 |
| WO | WO 2010/039939 | 4/2010 |
| WO | WO 2010/083283 | 7/2010 |
| WO | WO 2010/116282 | 10/2010 |
| WO | WO 2011/057022 | 5/2011 |
| WO | WO 2011/063159 | 5/2011 |
| WO | WO 2011/103423 | 8/2011 |
| WO | WO 2011/133637 | 10/2011 |
| WO | WO 2013/024895 | 2/2013 |
| WO | WO 2016/026974 | 2/2016 |
| WO | WO 2016/026975 | 2/2016 |
| WO | WO 2016/035014 | 3/2016 |
| WO | WO 2016/063294 | 4/2016 |
| WO | WO 2016/135582 | 9/2016 |
| WO | WO 2017/032349 | 3/2017 |
| WO | WO 2017/106957 | 6/2017 |
| WO | WO 2017/114461 | 7/2017 |
| WO | WO 2017/125097 | 7/2017 |
| WO | WO 2018/055097 | 3/2018 |
| WO | WO 2019/224677 | 11/2019 |
| WO | WO 2020/163653 | 8/2020 |
| WO | WO 2022040172 | 2/2022 |

OTHER PUBLICATIONS

Brown et al., "Vilsmeier Reaction on 6-Methylpurine," J Chem Soc., 1971, 0:128-132.

CAS No. 945950-37-8 "4-Methyl-7H-pyrrolo[2,3-d]pyrimidine," Chemical Book, retrieved on Mar. 9, 2021, retrieved from URL <https://www.chemicalbook.com/CASEN_945950-37-8.htm>, 3 pages.

Ciernik, "Formylation of Nitrogen-containing heterocycles and their quaternary salts," Collection Czechoslov Chem., 1972, 37:2273-2281 (English Abstract).

Doohan et al., "The photomediated reaction of alkynes with cycloalkanes," Organic & Biomolecular Chemistry., 2006, 4(5):942-952.

Greene et al., "Protective Groups in Organic Synthesis," 4d Ed., Wiley & Sons, 2007, 1111 pages.

Gupton et al., "Preparation of indole containing building blocks for the regiospecific construction of indole appended pyrazoles and pyrroles," Tetrahedron, Jul. 1, 2013, 69(29):5829-5840.

Li et al., "Synthesis of INCB018424 with High ee Value," Hecheng Huaxue, 2011, 19(2):280-282 (English Abstract).

International Search Report and Written Opinion in International Application No. PCT/US2021/046286, dated Nov. 9, 2021, 17 pages.

International Search Report and Written Opinion in International Application No. PCT/US2021/046298, dated Nov. 11, 2021, 14 pages.

Jones et al., "The Vilsmeier Reaction of Non-Aromatic Compounds," Organic Reactions, Hoboken, NJ, 2000, vol. 56, Ch. 2, pp. 355-659.

Kobor et al., "Synthesis of Acetic Acid, Propionic and Aminomethyl Theophylline Darivatives Substituted at Position 8," A Juhász Gyula Tanárképző Főiskola tudományos közleményei, 1977, pp. 31-40 (English Abstract).

Lin et al., "Enantioselective synthesis of Janus kinase inhibitor INCB018424 via an organocatalytic aza-Michael reaction," Organic Letters, May 2009, 11(9):1999-2002.

Mulyana et al., "New cobalt(II) and zinc(II) coordination frameworks incorporating a pyridyl-pyrazole ditopic ligand," Dalton Translations, 2005, 9:1598-1601.

Ooms et al., "Chemistry of Tetra-alkoxyethenes. Part V1.1 Cycloadditions with ag-Unsaturated Carbonyl Compounds and Chemistry of the Resulting Tetra-alkoxydihydropyrans," Journal of the Chemical Society, Perkin Transactions 1: Organic and Bio-Organic Chemistry, 1976, 14:1533-1538.

Ravin "Preformulation," Remington's Pharmaceutical Sciences, Mack Publishing Company, Easton, Pa., 1985,17th Ed., Chapter 76, pp. 1409-1423.

Saxena et al., "Synthesis and antiviral activity of certain 4-substituted and 2,4-disubstituted 7-[(2-hydroxyethoxy)methyl]pyrrolo[2,3-d]pyrimidines," Journal of Medicinal Chemistry, 1988, 31(8):1501-6.

Scott et al., "Jaks, STATs, Cytokines, and Sepsis." Clin Diagn Lab Immunol., 2002, 9(6):1153-1159.

Seus, "Vilsmeier Formylation of 4-Dimethylaminostilbene," J Org Chem., Aug. 1965, 30:2818-2821.

(56) References Cited

OTHER PUBLICATIONS

STN Reg No. 105-56-6, "Acetic acid, 2-cyano-, ethyl ester," dated Nov. 16, 1984, 1 page.
STN Reg No. 3473-63-0, "Methanimidamide, acetate," date Nov. 16, 1984, 1 page.
STN Reg No. 39929-79-8, "1H-Pyrrolo[2,3-d]pyrimidine-2,4(3H,7H)-dione," dated Nov. 16, 1984, 1 page.
STN Reg No. 5977-14-0, "Butanamide, 3-oxo-," dated Nov. 16, 1984, 1 page.
STN Reg No. 7252-83-7, "Ethane, 2-bromo-1, 1-dimethoxy-," dated Nov. 16, 1984, 1 page.
STN Reg No. 873-83-6, "2,4(1H,3H)-Pyrimidinedione, 6-amino-," dated Nov. 16, 1984, 1 page.
STN Reg No. 90213-66-4, "7H-Pyrrolo[2,3-d]pyrimidine, 2,4-dichloro-," dated Nov. 16, 1984, 1 page.
STN Reg No. 933715-40-3, "5-Pyrimidineacetic acid, 4-amino-6-methyl-," dated Apr. 30, 2007, 1 page.
Thiyagarajan et al., "Structure based medicinal chemistry approach to develop 4-methyl-7-deazaadenine carbocyclic nucleosides as anti-HCV agent," Bioorganic & Medicinal Chemistry Letters, 2012, 22(24):7742-7747.
Wiest et al., "A Route to 2-Substituted 3-Cyanopyrroles: Synthesis of Danaidal and Suffrutine A," Journal of Organic Chemistry (2016), 81(14):6149-6156.
International Preliminary Report on Patentability in International Application No. PCT/US2021/046286, dated Mar. 2, 2023, 9 pages.
International Preliminary Report on Patentability in International Application No. PCT/US2021/046298, dated Mar. 2, 2023, 7 pages.
International Search Report and Written Opinion in International Application No. PCT/US2022/073599, dated Sep. 30, 2022, 18 pages.

PROCESS AND INTERMEDIATES FOR PREPARING A JAK1 INHIBITOR

FIELD

The present invention is related to processes for preparing itacitinib, salts thereof, and related synthetic intermediate compounds and salts thereof. Itacitinib and salts thereof are useful as inhibitors of the Janus Kinase family of protein tyrosine kinases (JAKs) for treatment of inflammatory diseases, myeloproliferative disorders, and other diseases.

BACKGROUND

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P. et al, Nature 2001, 411(6835):355-365). Thus far, oncogenic protein kinases represent one of the largest and most attractive groups of protein targets for cancer intervention and drug development.

Protein kinases can be categorized as receptor type and non-receptor type. Receptor tyrosine kinases (RTKs) have an extracellular portion, a transmembrane domain, and an intracellular portion, while non-receptor tyrosine kinases are entirely intracellular. The Janus kinase family of protein tyrosine kinases (JAKs) belong to the non-receptor type of tyrosine kinases and include family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2).

The pathway involving JAKs and Signal Transducers and Activators of Transcription (STATs) is engaged in the signaling of a wide range of cytokines. Cytokines are low-molecular weight polypeptides or glycoproteins that stimulate biological responses in virtually all cell types. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription (Scott, M. J., C. J. Godshall, et al. (2002). "Jaks, STATs, Cytokines, and Sepsis." Clin Diagn Lab Immunol 9(6): 1153-9).

The JAK family plays a role in the cytokine-dependent regulation of proliferation and function of cells involved in immune response. The JAK/STAT pathway, and in particular all four members of the JAK family, are believed to play a role in the pathogenesis of the asthmatic response, chronic obstructive pulmonary disease, bronchitis, and other related inflammatory diseases of the lower respiratory tract. Moreover, multiple cytokines that signal through JAK kinases have been linked to inflammatory diseases or conditions of the upper respiratory tract such as those affecting the nose and sinuses (e.g., rhinitis, sinusitis) whether classically allergic reactions or not. The JAK/STAT pathway has also been implicated to play a role in inflammatory diseases/conditions of the eye including, but not limited to, iritis, uveitis, scleritis, conjunctivitis, as well as chronic allergic responses. Therefore, inhibition of JAK kinases may have a beneficial role in the therapeutic treatment of these diseases.

Blocking signal transduction at the level of the JAK kinases holds promise for developing treatments for human cancers. Inhibition of the JAK kinases is also envisioned to have therapeutic benefits in patients suffering from skin immune disorders such as psoriasis, and skin sensitization. Accordingly, inhibitors of Janus kinases or related kinases are widely sought and several publications report effective classes of compounds. For example, JAK inhibitor itacitinib, (2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile), is reported in U.S. Pat. App. Pub. Nos. 2011/0224190 and 2015/0065484; and their disclosures are incorporated herein by reference.

In view of the growing demand for compounds for the treatment of disorders related to the inhibition of kinases such as Janus kinases, new and more efficient routes to itacitinib, salts thereof, and intermediates related thereto, are needed. The processes and compounds described herein help meet these and other needs.

SUMMARY

The present disclosure provides, inter alia, processes of preparing itacitinib, salts thereof, and related synthetic intermediate compounds and salts of the intermediates.

Accordingly, the present disclosure provides processes of preparing itacitinib, or a salt thereof, comprising reacting a compound of formula 3:

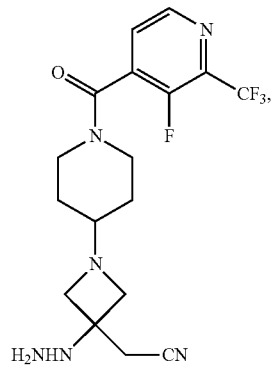

or a salt thereof, with a reagent selected from (i) a salt of formula 2a and (ii) a compound of formula 2b:

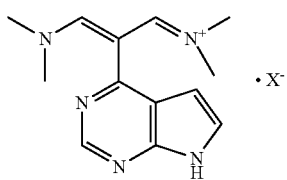

2a

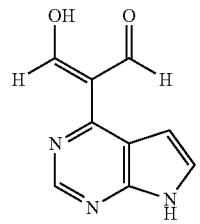

2b wherein X⁻ is a counter anion.

In some embodiments, the processes of preparing itacitinib, or a salt thereof, provided herein comprise:

reacting a compound of formula 50:

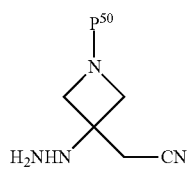

50 or a salt thereof, with a reagent selected from (i) a salt of formula 2a and (ii) a compound of formula 2b:

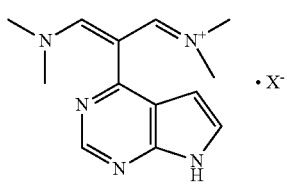

2a

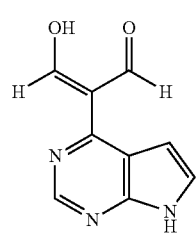

2b to form a compound of formula 51:

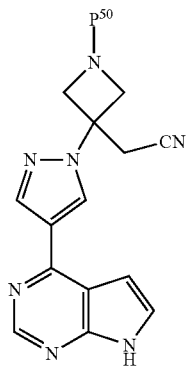

51 wherein X⁻ is a counter anion; and $P^{50}$ is an amino protecting group.

The present disclosure further provides processes of preparing itacitinib, or a salt thereof, comprising reacting a salt of formula 2c:

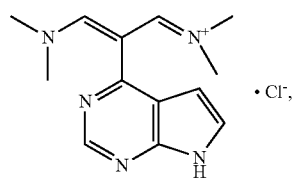

2c with a compound of formula 3:

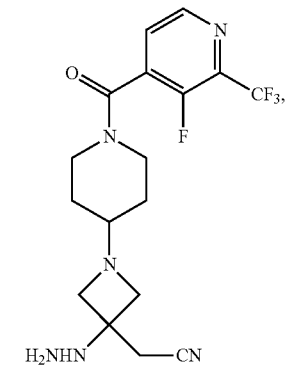

3 or a salt thereof, to form the itacitinib, or the salt thereof.

The present disclosure further provides processes of preparing itacitinib, or a salt thereof, comprising reacting a salt of formula 2c:

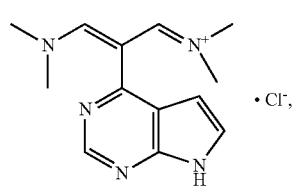

2c with a compound of formula 50:

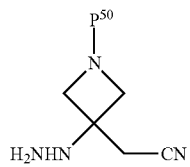

or a salt thereof, to form a compound of formula 51:

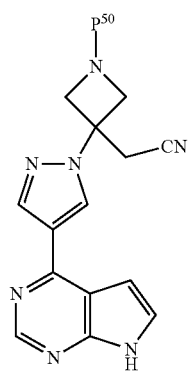

or a salt thereof, wherein P⁵⁰ is an amino protecting group;
deprotecting the compound of formula 51 to form a compound of formula 52:

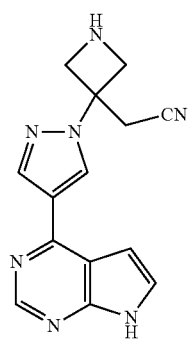

or a salt thereof; and
reacting the compound of formula 52, or a salt thereof, with a compound of formula 53:

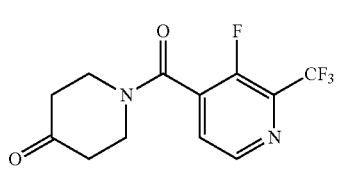

in the presence of coupling agent and a base to form itacitinib, or a salt thereof.

In some embodiments, the salt of formula 2c is prepared by a process comprising reacting a salt of formula 2d:

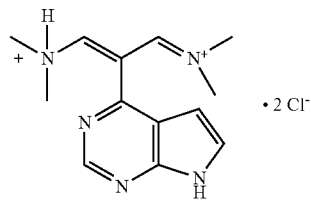

with a base to form the salt of formula 2c.

In some embodiments, the salt of formula 2d is prepared by a process comprising:
reacting a compound of formula 2P:

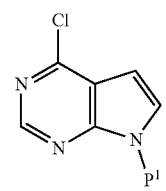

with MeMgBr in the presence of a Grignard catalyst to form a compound of formula 1aP:

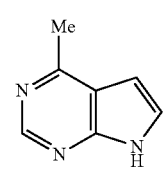

deprotecting the compound of formula 1aP to form a compound of formula 1a:

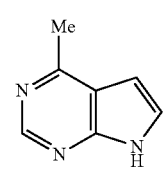

or a salt thereof; and
reacting the compound of formula 1a, or the salt thereof, with a Vilsmeier reagent formed from dimethylformamide and a chlorinating agent to form the salt of formula 2d;
wherein P¹ is an amino protecting group.

In some embodiments, the salt of formula 2d is prepared by a process comprising:
reacting a compound of formula 22P:

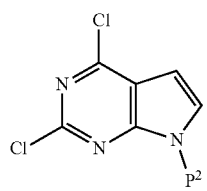

with MeMgBr in the presence of a Grignard catalyst to form a compound of formula 23P:

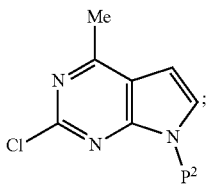

reducing the compound of formula 23P to form a compound of formula 1a:

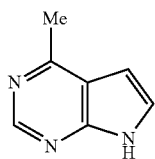

or a salt thereof; and
reacting the compound of formula 1a, or the salt thereof, with a Vilsmeier reagent formed from dimethylformamide and a chlorinating agent to form the salt of formula 2d;
wherein $P^2$ is an amino protecting group.

The present disclosure further provides a compound of formula 50, having the formula:

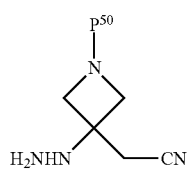

or a salt thereof, wherein $P^{50}$ is an amino protecting group.

The present disclosure further provides a compound of formula 3, having the formula:

or a salt thereof.

The details of one or more embodiments of the invention are set forth in the accompanying drawings and the description below. Other features, objects, and advantages of the invention will be apparent from the description and drawings, and from the claims.

DETAILED DESCRIPTION

Processes and Intermediates

Figure 1:
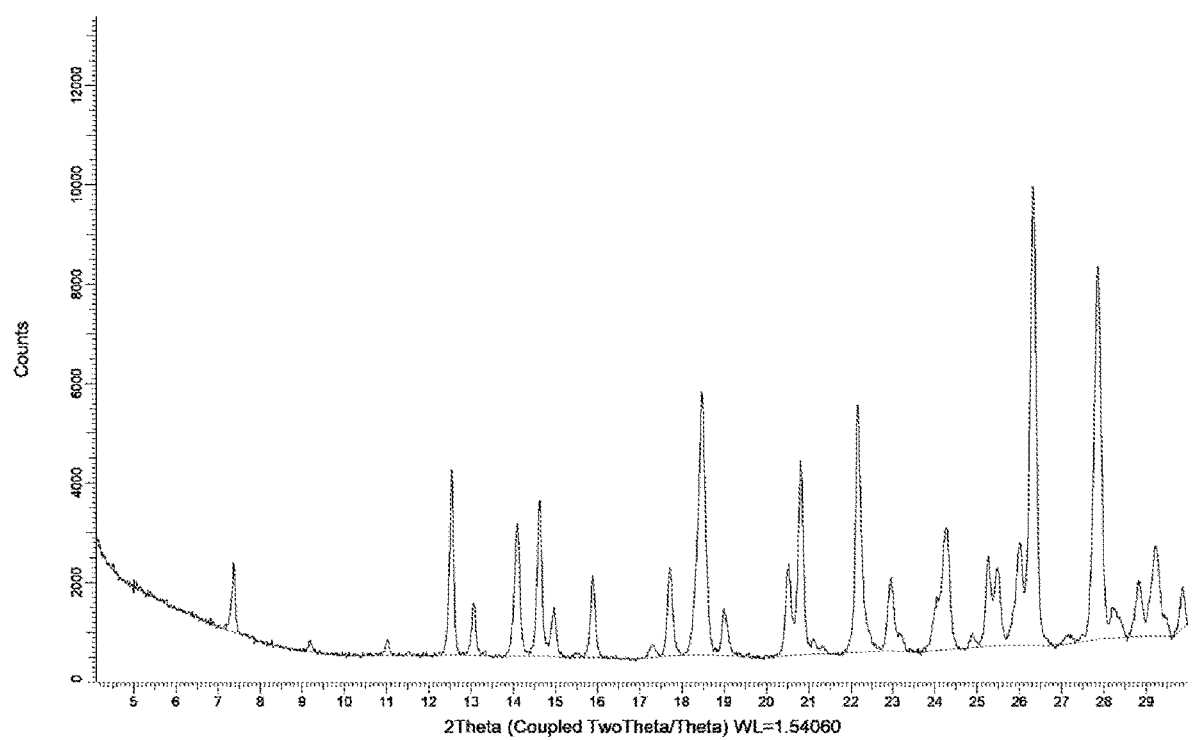
FIG. 1 is an X-ray powder diffraction (XRPD) pattern of Compound 2d Form I.

The present disclosure provides processes of preparing the selective JAK1 inhibitor itacitinib, also known as 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile, and intermediates thereof as well as salts and crystalline forms of itacitinib and intermediates. Itacitinib (also known as INCB039110) has the following structure:

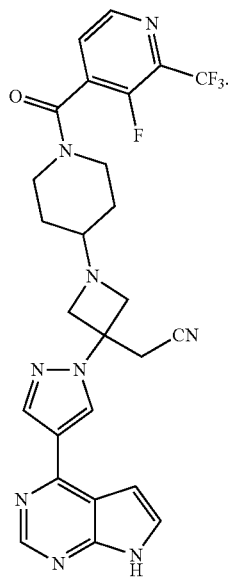

Compound 1

2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile is also referred to as Compound 1 in this disclosure. The compound and various processes of preparing the compound are disclosed in U.S. Pat. App. Pub. Nos. 2011/0224190, 2013/0060026, 2014/0256941, and 2015/0065484, which are hereby incorporated herein by reference. Itacitinib is a potent JAK1 inhibitor with more than 10-fold selectivity over JAK2 and JAK3.

The present disclosure provides a process of preparing itacitinib, or a salt thereof, comprising:
reacting a compound of formula 3:

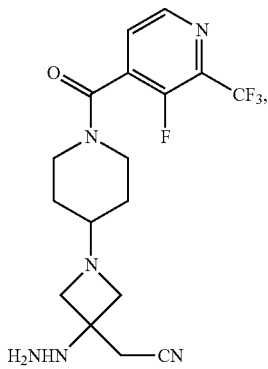

3 or a salt thereof, with a reagent selected from (i) a salt of formula 2a, or a salt thereof, and (ii) a compound of formula 2b:

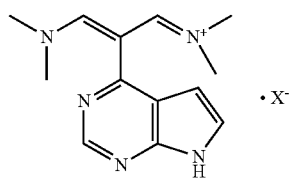

2a

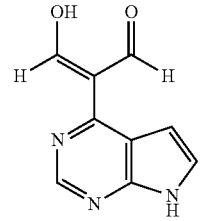

2b wherein X⁻ is a counter anion.

The present disclosure provides a process of preparing itacitinib, or a salt thereof, comprising:
reacting a compound of formula 3:

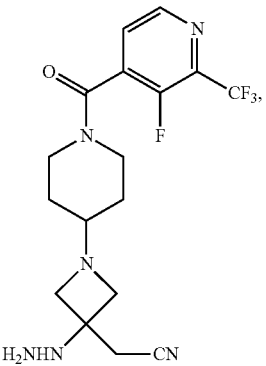

3 or a salt thereof, with a reagent selected from (i) a salt of formula 2a and (ii) a compound of formula 2b:

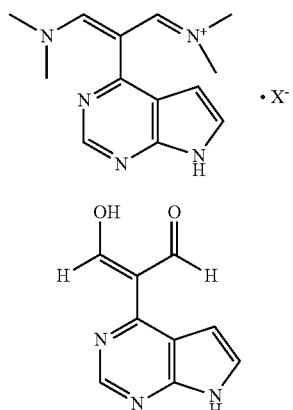

2a

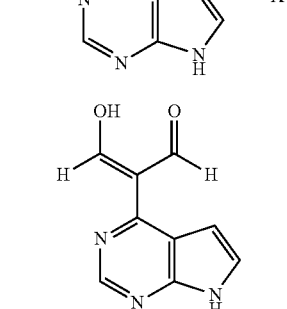

2b wherein X⁻ is a counter anion.

In some embodiments, the reagent is the salt of formula 2a.

In some embodiments, the reagent is the compound of formula 2b.

In some embodiments, the reagent is the salt of the salt of formula 2a, wherein X⁻ is Cl⁻.

In some embodiments, the reagent is the hydrochloric acid salt of the salt of formula 2a, wherein X⁻ is Cl⁻.

In some embodiments, about 1 to about 1.5 molar equivalents of the compound of formula 3, or the salt thereof, is utilized relative to the reagent. In some embodiments, about 1.2 to about 1.4 molar equivalents of the compound of formula 3, or the salt thereof, is utilized relative to the reagent. In some embodiments, about 1.3 molar equivalents of the compound of formula 3, or the salt thereof, is utilized relative to the reagent.

In some embodiments, the reacting of the reagent with the compound of formula 3, or the salt thereof, is carried out in a solvent component S1. In some embodiments, the solvent component S1 comprises a polar protic solvent or a polar aprotic solvent.

In some embodiments, the solvent component S1 comprises an alcohol. In some embodiments, the solvent component S1 comprises formula $C_{1-6}$ alkyl-OH. In some embodiments, the solvent component S1 comprises ethanol. In some embodiments, the solvent component S1 is ethanol.

In some embodiments, the reacting of the compound of formula 3, or a salt thereof, with the reagent is conducted at a temperature of from about 20° C. to about 30° C. In some embodiments, the reacting of the compound of formula 3, or a salt thereof, with the reagent is conducted at an ambient temperature.

In some embodiments, the present application further provides a process of preparing itacitinib, or a salt thereof, comprising:

reacting a compound of formula 50:

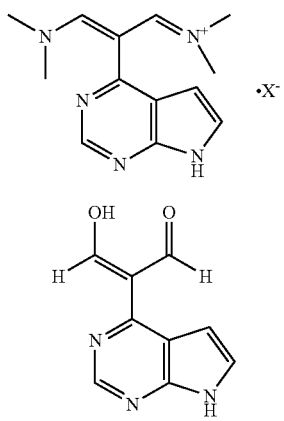

50 or a salt thereof, with a reagent selected from (i) a salt of formula 2a, and (ii) a compound of formula 2b:

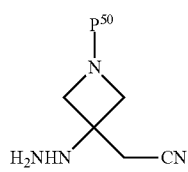

2a

2b to form a compound of formula 51:

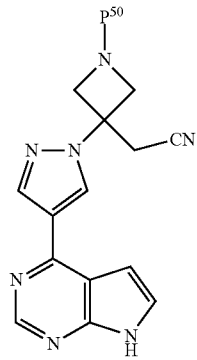

51 wherein X⁻ is a counter anion; and $P^{50}$ is an amino protecting group.

In some embodiments, $P^{50}$ is selected from $R^{50}$—O—C(O)—, wherein $R^{50}$ is $C_{1-6}$ alkyl.

In some embodiments, $R^{50}$ is methyl, ethyl, propyl, isopropyl, butyl or t-butyl. In some embodiments, $P^{50}$ is t-butyl-O—C(O)—.

In some embodiments, from about 1 to about 1.5 molar equivalents of the compound of formula 50, or the salt thereof, is utilized relative to the reagent. In some embodiments, from about 1.2 to about 1.4 molar equivalents of the compound of formula 50, or the salt thereof, is utilized relative to the reagent. In some embodiments, about 1.3 molar equivalents of the compound of formula 50, or the salt thereof, is utilized relative to the reagent.

In some embodiments, the reacting of the reagent with the compound of formula 50, or the salt thereof, is carried out in a solvent component S50. In some embodiments, the solvent component S50 comprises a polar protic solvent or a polar aprotic solvent.

In some embodiments, the solvent component S50 comprises an alcohol. In some embodiments, the solvent component S50 comprises formula $C_{1-6}$ alkyl-OH. In some embodiments, the solvent component S50 comprises ethanol.

In some embodiments, the reacting of the compound of formula 50, or a salt thereof, with the reagent is conducted at a temperature of from about 20° C. to about 30° C. In some embodiments, the reacting of the compound of formula 50, or a salt thereof, with the reagent is conducted at an ambient temperature.

In some embodiments, the process of preparing itacitinib, or a salt thereof, further comprises deprotecting the compound of formula 51 to form a compound of formula 52:

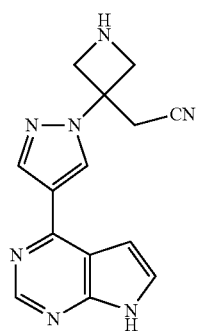

52 or a salt thereof.

In some embodiments, the deprotecting of the compound of formula 51 comprises treating the compound of formula 51 with a strong acid A51.

In some embodiments, the strong acid A51 is HCl. In some embodiments, about 5 to 10 molar equivalents of HCl are used relative to the compound of formula 51. In some embodiments, from about 6 to 8 molar equivalents of HCl are used relative to the compound of formula 51.

In some embodiments, the treating of the compound of formula 51 with a strong acid A51 is conducted in a solvent component S51. In some embodiments, the solvent component S51 comprises a polar protic solvent and an organic solvent.

In some embodiments, the solvent component S51 comprises water, alcohol and halogenated hydrocarbon. In some embodiments, the alcohol of solvent component S50 comprises formula $C_{1-6}$ alkyl-OH.

In some embodiments, the solvent component S51 comprises water, isopropanol, and dichloromethane.

In some embodiments, the treating of the compound of formula 51 with a strong acid A51 is conducted at a reflux temperature.

In some embodiments, the treating of the compound of formula 51 with a strong acid A51 is conducted at a temperature of from about 30° C. to about 60° C.

In some embodiments, the treating of the compound of formula 51 with a strong acid A51 is conducted at a temperature of from about 35° C. to about 50° C.

In some embodiments, the treating of the compound of formula 51 with a strong acid A51 is conducted at a temperature of from about 40° C. to about 45° C.

In some embodiments, the compound of formula 52, or salt thereof, is the dihydrochloride salt of the compound of formula 52.

In some embodiments, the process of preparing itacitinib, or a salt thereof, further comprises reacting the compound of formula 52, or a salt thereof, with a compound of formula 53:

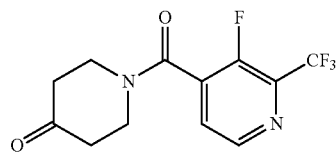

53 in the presence of coupling agent to form itacitinib.

In some embodiments, the coupling agent is sodium triacetoxyborohydride.

In some embodiments, the reacting of the compound of formula 52, or a salt thereof, with a compound of formula 53 is conducted in the presence of a base B53.

In some embodiments, the base B53 is a tertiary amine. In some embodiments, the base B53 is a tri-($C_{1-6}$ alkyl)amine. In some embodiments, the base B53 is triethylamine.

In some embodiments, from about 1 to about 1.5 molar equivalents of the compound of formula 53 are utilized relative to the compound of formula 52, or the salt thereof.

In some embodiments, from about 1 to about 1.1 molar equivalents of the compound of formula 53 are utilized relative to the compound of formula 52, or the salt thereof.

In some embodiments, from about 1 to about 3 molar equivalents of the coupling agent are utilized relative to the compound of formula 52, or the salt thereof. In some embodiments, about 2 molar equivalents of the coupling agent are utilized relative to the compound of formula 52, or the salt thereof. In some embodiments, from about 1 to about 3 molar equivalents of base B53 are utilized relative to the compound of formula 52, or the salt thereof. In some embodiments, about 2 molar equivalents of the base B53 are utilized relative to the compound of formula 52, or the salt thereof.

In some embodiments, the reacting of the compound of formula 52, or a salt thereof, with a compound of formula 53 is conducted in a solvent component S52. In some embodiments, the solvent component S52 comprises an organic solvent.

In some embodiments, the solvent component S52 comprises dichloromethane.

In some embodiments, the reacting of the compound of formula 52, or a salt thereof, with a compound of formula 53 is conducted at a temperature of from about 20° C. to about 30° C. In some embodiments, the reacting of the compound of formula 52, or a salt thereof, with a compound of formula 53 is conducted at an ambient temperature.

In some embodiments, the process of preparing itacitinib, or a salt thereof, further comprises reacting itacitinib with at least one equivalent of adipic acid to form itacitinib adipate (i.e., itacitinib adipic acid salt).

In some embodiments, the reagent is the salt of formula 2a. $X^-$ can be selected from $Cl^-$, $Br^-$, $I^-$, $BF_4^-$, $PF_6^-$, $AsF_6^-$, $SbF_6^-$, and $ClO_4^-$. In some embodiments, $X^-$ is selected from $Cl^-$, $BF_4^-$, $PF_6^-$, $AsF_6^-$, $SbF_6^-$, and $ClO_4^-$. In some embodiments, $X^-$ is $BF_4^-$. In some embodiments, $X^-$ is $PF_6^-$. In some embodiments, $X^-$ is $AsF_6^-$. In some embodiments, $X^-$ is $SbF_6^-$. In some embodiments, $X^-$ is $ClO_4^-$. In some embodiments, $X^-$ is $Cl^-$.

In some embodiments, the reagent is the compound of formula 2b. The compound of formula 2b can be prepared by a process comprising reacting the salt of formula 2a with a base B1. In some embodiments, the reacting of the salt of formula 2a with the base B1 is conducted in a solvent component S2 comprising water. In some embodiments, the base B1 is a strong base. In some embodiments, the base B1 is a hydroxide. In some embodiments, the base B1 is an alkali metal hydroxide. In some embodiments, the base B1 is sodium hydroxide. In some embodiments, from about 10 to about 15 molar equivalents of the base B1 is utilized relative to the salt of formula 2a, or salt thereof. In some embodiments, from about 12 molar equivalents of the base B1 is utilized relative to the salt of formula 2a, or salt thereof. In some embodiments, the reacting of the salt of formula 2a with the base B1 is conducted at a temperature of from about −10° C. to about 60° C. In some embodiments, temperature is from about 0° C. to room temperature. In some embodiments, temperature is from about 40° C. to about 60° C. In some embodiments, the temperature is from 0° C. to room temperature and then heated to from about 40° C. to about 60° C.

In some embodiments, the salt of formula 2a or the compound of formula 2b can be prepared by a process comprising:

reacting the compound of formula 1a:

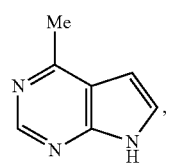

1a

, or a salt thereof, with a Vilsmeier reagent formed from dimethylformamide.

In the some embodiments, the salt of formula 2a or the compound of formula 2b can be prepared by a process comprising:

reacting the compound of formula 5a:

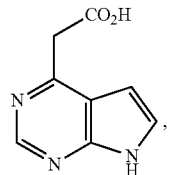

or a salt thereof, with a Vilsmeier reagent formed from dimethylformamide.

In some embodiments, the compound of formula 5a is a salt. For example, the compound of formula 5a is the sodium salt.

In some embodiments, the reacting of the compound of formula 5a, or salt thereof, with a Vilsmeier reagent produces a compound of formula 2c:

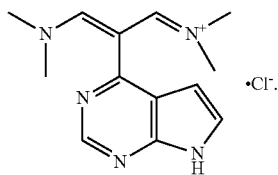

In some embodiments, after the reacting with a Vilsmeier reagent, the compound of formula 2c is reacted with a salt of formula $M^+X^-$, wherein $M^+$ is a counter cation.

In some embodiments, the Vilsmeier reagent is prepared by a process comprising reacting dimethylformamide with a chlorinating agent. In some embodiments, the chlorinating agent is selected from oxalyl chloride, phosphorus oxychloride, triphosgene, thionyl chloride, sulfuryl chloride, and phosphorus pentachloride. In some embodiments, the chlorinating agent is selected from oxalyl chloride, phosphorus oxychloride, and triphosgene. In some embodiments, the chlorinating agent is oxalyl chloride. In some embodiments, the chlorinating agent is phosphorus oxychloride. In some embodiments, the chlorinating agent is triphosgene.

In some embodiments, from about 1 to about 5 molar equivalents of the chlorinating agent are utilized relative to the compound of formula 1a or 5a, or the salt thereof. In some embodiments, from about 1 to about 4 molar equivalents of the chlorinating agent are utilized relative to the compound of formula 1a or 5a, or the salt thereof. In some embodiments, from about 1 to about 3 molar equivalents of the chlorinating agent are utilized relative to the compound of formula 1a or 5a, or the salt thereof. In some embodiments, about 1 molar equivalent of the chlorinating agent is utilized relative to the compound of formula 1a or 5a, or the salt thereof. In some embodiments, about 2 molar equivalents of the chlorinating agent are utilized relative to the compound of formula 1a or 5a, or the salt thereof. In some embodiments, about 3 molar equivalents of the chlorinating agent are utilized relative to the compound of formula 1a or 5a, or the salt thereof. In some embodiments, about 4 molar equivalents of the chlorinating agent are utilized relative to the compound of formula 1a or 5a, or the salt thereof. In some embodiments, about 5 molar equivalents of the chlorinating agent are utilized relative to the compound of formula 1a or 5a, or the salt thereof.

In some embodiments, from about 10 to about 25 molar equivalents of dimethylformamide are utilized relative to the compound of formula 1a or 5a, or the salt thereof. In some embodiments, from about 10 to about 20 molar equivalents of dimethylformamide are utilized relative to the compound of formula 1a or 5a, or the salt thereof. In some embodiments, from about 10 to about 15 molar equivalents of dimethylformamide are utilized relative to the compound of formula 1a or 5a, or the salt thereof. In some embodiments, from about 11 to about 14 molar equivalents of dimethylformamide are utilized relative to the compound of formula 1a or 5a, or the salt thereof. In some embodiments, from about 11 to about 13 molar equivalents of dimethylformamide are utilized relative to the compound of formula 1a or 5a, or the salt thereof.

In some embodiments, the preparation of the Vilsmeier reagent is carried out in a solvent component S3. In some embodiments, the solvent component S3 comprises an organic solvent. In some embodiments, the solvent component S3 comprises a polar aprotic solvent. In some embodiments, the solvent component S3 comprises acetonitrile, dimethylformamide, or a combination thereof.

In some embodiments, the Vilsmeier reagent is prepared at a temperature between from about −10° C. to about 60° C. In some embodiments, the Vilsmeier reagent is prepared at a temperature between from about −10° C. to about 30° C. For example, the Vilsmeier reagent is prepared at a temperature between from about −10° C. to about room temperature. For example, the temperature is about 0° C. to about room temperature. In some embodiments, the Vilsmeier reagent is prepared at a temperature between from about room temperature to about 60° C. In some embodiments, the Vilsmeier reagent is prepared at a temperature between from about 30° C. to about 70° C., about 40° C. to about 70° C., about 30° C. to about 60° C., or about 40° C. to about 60° C.

In some embodiments, the reacting of the compound of formula 1a or 5a, or the salt thereof, with the Vilsmeier reagent is carried out at a temperature of from about 40° C. to about 100° C. In some embodiments, the reacting of the compound of formula 1a or 5a, or the salt thereof, with the Vilsmeier reagent is carried out at a temperature of from about 70° C. to about 100° C. In some embodiments, the reacting of the compound of formula 1a or 5a, or the salt thereof, with the Vilsmeier reagent is carried out at a temperature of from about 40° C. to about 60° C. For example, the Vilsmeier reagent is prepared at a temperature between from about 75° C. to about 80° C., 80° C. to 90° C., or 85° C. to 90° C.

In some embodiments, the product of the reacting with the Vilsmeier reagent has formula 2c:

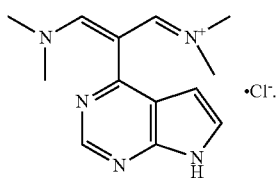

In some embodiments, the salt of formula 2a can be formed by a process comprising:
reacting the salt of formula 2c:

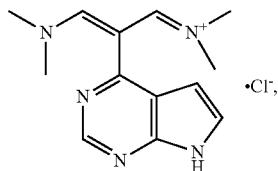

with a salt of formula M⁺X⁻, wherein:
M⁺ is a counter cation; and
X⁻ is a counter anion other than Cl⁻.

In some embodiments, M⁺ is an alkali metal counter cation. For example, M⁺ is Li⁺, Na⁺ or K⁺. In some embodiments, M⁺ is Na⁺. In some embodiments, X⁻ is selected from Br⁻, I⁻, BF$_4^-$, PF$_6^-$, AsF$_6^-$, SbF$_6^-$, and ClO$_4^-$. For example, X⁻ is selected from BF$_4^-$, PF$_6^-$, AsF$_6^-$, SbF$_6^-$, and ClO$_4^-$. In some embodiments, X⁻ is BF$_4^-$. In some embodiments, X⁻ is PF$_6^-$. In some embodiments, X⁻ is AsF$_6^-$. In some embodiments, X⁻ is SbF$_6^-$. In some embodiments, X⁻ is ClO$_4^-$.

In some embodiments, the product of the reacting with the Vilsmeier reagent has formula 2c:

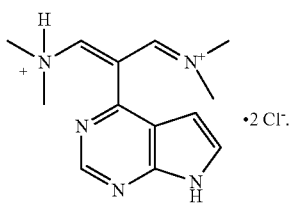

In some embodiments, the salt of formula 2c can be produced by a process comprising:
reacting a salt of formula 2d:

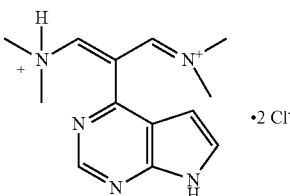

with a base.

In some embodiments, the compound of formula 2b is prepared by a process comprising reacting a salt of formula 2d with a base B2. In some embodiments, (i) the reacting of the salt of formula 2d with a base B2 and (ii) the reacting of the salt of formula 2a with the compound of formula 3 are conducted in a single pot (e.g., in a single reaction vessel). In some embodiments, the reacting of the salt of formula 2d with a base B2 is conducted in a solvent component comprising water. In some embodiments, the base B2 is a strong base. In some embodiments, the base B2 is a hydroxide base. In some embodiments, the base B2 is an alkali metal hydroxide. For example, the base B2 is sodium hydroxide.

In some embodiments, the reacting of the salt of formula 2d with a base B2 is conducted at a temperature of from about −10° C. to about 15° C. In some embodiments, the compound of formula 1a, or the salt thereof, is the hydrochloride salt.

In some embodiments, the compound of formula 1a, or the salt thereof, can be prepared by a process comprising:
deprotecting a compound of formula 1aP:

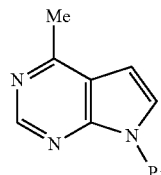

wherein P¹ is an amino protecting group.

In some embodiments, P¹ is selected from (R¹)₃Si, wherein R¹ is C$_{1-6}$ alkyl. In some embodiments, R¹ is methyl, ethyl, propyl, isopropyl, butyl or t-butyl. In some embodiments, P¹ is t-butyldimethylsilyl. In some embodiments, the deprotecting is carried out by reacting the compound of formula 1aP with a base B3. In some embodiments, the base B3 is a hydroxide base. For example, the base B3 is ammonium hydroxide. In some embodiments, the deprotecting is carried out in a solvent component S4. In some embodiments, the solvent component S4 comprises a polar protic solvent. In some embodiments, the solvent component S4 comprises an alcohol. In some embodiments, the solvent component S4 comprises formula C$_{1-6}$ alkyl-OH. For example, the solvent component S4 comprises methanol.

In some embodiments, the compound of formula 1aP can be prepared by a process comprising:
reacting a compound of formula 2P:

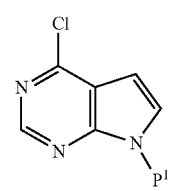

with MeMgBr in the presence of a Grignard catalyst,
wherein P¹ is an amino protecting group.

In some embodiments, the catalyst is an iron catalyst. In some embodiments, the iron catalyst is iron(III) acetylacetonate. In some embodiments, from about 1 to about 2 molar equivalents of MeMgCl are utilized relative to the compound of formula 2P. In some embodiments, from about 1% to about 10% molar equivalents of the catalyst are utilized relative to the compound of formula 2P. In some embodiments, the reacting of the compound formula 2P with MeMgCl is carried out in a solvent component S5. In some embodiments, the solvent component S5 comprises a di-C$_{1-6}$ alkyl ether or a 4-10 membered heterocycloalkyl ether. For example, the solvent component S5 comprises a tetrahydrofuran. In some embodiments, the reacting of the compound formula 2P with MeMgCl is carried out at a temperature of from about −10° C. to about 30° C.

In some embodiments, the compound of formula 2P can be prepared by a process comprising:

protecting a compound of formula 12a:

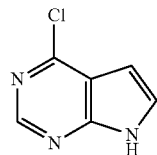

12a to form the compound of formula 2P.

In some embodiments, the protecting comprises reacting the compound of formula 12a with an alkali metal hydride and P¹—Y, wherein Y is halo. In some embodiments, P¹—Y is $(R^1)_3Si$—Y, wherein Y is halo and $R^1$ is $C_{1-6}$ alkyl. In some embodiments, $P^1$ is $(R^1)_3Si$, wherein $R^1$ is $C_{1-6}$ alkyl. In some embodiments, $R^1$ is methyl, ethyl, propyl, isopropyl, butyl or t-butyl. In some embodiments, $P^1$ is t-butyldimethylsilyl. In some embodiments, the alkali metal hydride is sodium hydride. In some embodiments, from about 1 to about 2 molar equivalents of the alkali metal hydride is utilized relative to the compound of formula 12a. In some embodiments, from about 1 to about 2 molar equivalents of P¹—Y is utilized relative to the compound of formula 12a. In some embodiments, the reacting of the compound of formula 12a with the alkali metal hydride and P¹—Y is carried out at a temperature of about −10° C. to about 20° C. In some embodiments, the reacting of the compound of formula 12a with the alkali metal hydride and P¹—Y is carried out in a solvent component S6, wherein the solvent component S6 comprises an organic solvent. In some embodiments, the solvent component S6 comprises a di-$C_{1-6}$ alkyl ether or a 4-10 membered heterocycloalkyl ether. In some embodiments, the solvent component S6 comprises a tetrahydrofuran.

In some embodiments, the compound of formula 1a, or the salt thereof, can be prepared by a process comprising:

reducing a compound of formula 23P:

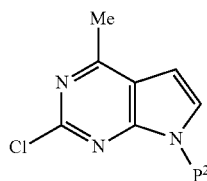

23P wherein $P^2$ is an amino protecting group.

In some embodiments, the reducing of the compound of formula 23P is accomplished by a process comprising reacting the compound of formula 23P with hydrogen gas in the presence of a catalyst. For example, the catalyst is $Pd^0$ on carbon. In some embodiments, the amount of the catalyst relative to the compound of formula 23P is about 5% to about 15% by weight. In some embodiments, the reacting of the compound of formula 23P with hydrogen and the catalyst is carried out at a temperature of about 40° C. to about 70° C. In some embodiments, the reacting of the compound of formula 23P with hydrogen and the catalyst is carried out at a temperature of about 50° C. to about 60° C. In some embodiments, the reacting of the compound of formula 23P with hydrogen and the catalyst is carried out at a temperature of about 50° C. to about 55° C. In some embodiments, the reacting of the compound of formula 23aP with hydrogen and the catalyst is carried out in a solvent component S7. In some embodiments, the solvent component S7 comprises a polar protic solvent. In some embodiments, the solvent component S7 comprises an alcohol. In some embodiments, the solvent component S7 comprises formula $C_{1-6}$ alkyl-OH. For example, the solvent component S7 comprises methanol.

In some embodiments, the compound of formula 23P can be prepared by a process comprising:

reacting a compound of formula 22P:

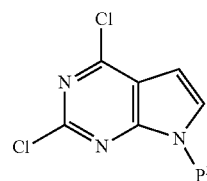

22P with MeMgBr in the presence of a Grignard catalyst, wherein $P^2$ is an amino protecting group.

In some embodiments, the catalyst is an iron catalyst. For example, the iron catalyst is iron(III) acetylacetonate. In some embodiments, from about 1 to about 2 molar equivalents of MeMgCl is utilized relative to the compound of formula 22P. In some embodiments, from about 1% to about 10% molar equivalents of the catalyst are utilized relative to the compound of formula 22P. In some embodiments, the reacting of the compound formula 22P with MeMgCl is carried out in a solvent component S8. In some embodiments, the solvent component S8 comprises a di-$C_{1-6}$ alkyl ether or a 4-10 membered heterocycloalkyl ether. For example, the solvent component S8 comprises a tetrahydrofuran. In some embodiments, the reacting of the compound formula 2P with MeMgCl is carried out at a temperature of from about −10° C. to about 30° C.

In some embodiments, the compound of formula 22P can be prepared by a process comprising:

protecting a compound of formula 22a:

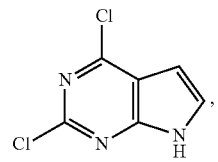

22a to form the compound of formula 22P.

In some embodiments, the protecting comprise reacting the compound of formula 22a with an alkali metal hydride and P²—Y, wherein Y is halo. In some embodiments, $P^2$ is $(R^1)_3Si$, wherein $R^1$ is $C_{1-6}$ alkyl. In some embodiments, $R^1$ is methyl, ethyl, propyl, isopropyl, butyl or t-butyl. In some embodiments, $P^2$ is t-butyldimethylsilyl. In some embodiments, the alkali metal hydride is sodium hydride.

In some embodiments, from about 1 to about 2 molar equivalents of the alkali metal hydride is utilized relative to the compound of formula 22a. In some embodiments, from about 1 to about 2 molar equivalents of P²—Y is utilized relative to the compound of formula 22a. In some embodiments, the reacting of the compound of formula 22a with the alkali metal hydride and $P^2$—Y is carried out at a temperature of about –10° C. to about 20° C. In some embodiments, the reacting of the compound of formula 22a with the alkali metal hydride and $P^2$—Y is carried out in a solvent component S9, wherein the solvent component S9 comprises an organic solvent. In some embodiments, the solvent component S9 comprises a di-$C_{1-6}$ alkyl ether or a 4-10 membered heterocycloalkyl ether. For example, the solvent component S9 comprises a tetrahydrofuran.

In some embodiments, the compound of formula 1a, or the salt thereof, can be prepared by a process comprising:
reacting a compound of formula 18a:

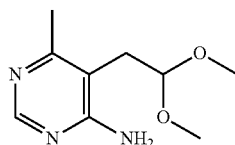

18a with an acid A1 to form the compound of formula 1a.

In some embodiments, the acid A1 is a strong acid. For example, the acid A1 is hydrochloric acid. In some embodiments, the reacting of the compound of formula 18a with the acid A1 is carried out in a solvent component S10, wherein the solvent component S10 comprises a polar protic solvent. In some embodiments, the solvent component S10 comprises an alcohol. In some embodiments, the solvent component S10 comprises formula $C_{1-6}$ alkyl-OH. For example, the solvent component S10 comprises isopropyl alcohol.

In some embodiments, the compound of formula 18a, or a salt thereof, can be prepared by a process comprising:
reacting a compound of formula 17a:

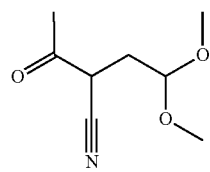

17a with formamidine acetate and triethyl orthoformate to form the compound of formula 17a.

In some embodiments, from about 10 to about 15 molar equivalents of formamidine acetate is utilized relative to the compound of formula 17a. In some embodiments, about 10, about 11, about 12, about 13, about 14, or about 15 molar equivalents of formamidine acetate is utilized relative to the compound of formula 17a. In some embodiments, about 12 molar equivalents of formamidine acetate is utilized relative to the compound of formula 17a. In some embodiments, from about 6 to about 10 molar equivalents of triethyl orthoformate is utilized relative to the compound of formula 17a. In some embodiments, about 6, about 7, about 8, about 9, or about 10 molar equivalents of triethyl orthoformate is utilized relative to the compound of formula 17a. For example, about 8 molar equivalents of triethyl orthoformate is utilized relative to the compound of formula 17a. In some embodiments, the reacting of the compound of formula 17a with formamidine acetate and triethyl orthoformate is carried out at a temperature of about 100° C. to about 150° C. For example, the temperature can be about 110° C. to about 120° C. In some embodiments, the reacting of the compound of formula 17a with formamidine acetate and triethyl orthoformate is carried out in a solvent component S11, wherein the solvent component S11 comprises a polar protic solvent. In some embodiments, the solvent component S11 comprises an alcohol. In some embodiments, the solvent component S11 comprises formula $C_{1-6}$ alkyl-OH. For example, the solvent component S11 comprises 1-butanol.

In some embodiments, the compound of formula 17a, or a salt thereof, can be prepared by a process comprising:
reacting a compound of formula 20a:

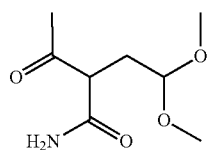

20a with a compound of formula 21a:

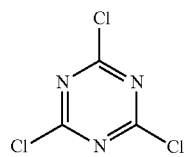

21a to form the compound of formula 17a.

In some embodiments, from about 0.4 to about 1 molar equivalents of the compound of formula 21a is utilized relative to the compound of formula 20a. In some embodiments, the reacting of the compound of formula 20a with the compound of formula 21a is carried out at room temperature. In some embodiments, the reacting of the compound of formula 20a with the compound of formula 21a is carried out in a solvent component S12, wherein the solvent component S12 comprises a polar aprotic solvent. For example, the solvent component S12 comprises dimethylformamide.

In some embodiments, the compound of formula 20a, or a salt thereof, can be prepared by a process comprising:
reacting a compound of formula 19a:

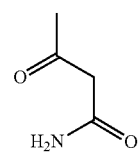

19a with bromo-1,1-dimethoxyethane and a base B4 to form the compound of formula 20a.

In some embodiments, the base B4 is an alkali metal carbonate. For example, the base B4 is cesium carbonate. In some embodiments, from about 1 to about 2 molar equivalents of the base B4 is utilized relative to the compound of formula 19a. In some embodiments, from about 1 to about 2 molar equivalents of bromo-1,1-dimethoxyethane is utilized relative to the compound of formula 19a. In some embodiments, the reacting of the compound of formula 19a with bromo-1,1-dimethoxyethane is carried out at a temperature of about 70° C. to about 100° C. In some embodiments, the reacting of the compound of formula 19a with bromo-1,1-dimethoxyethane is carried out in a solvent component S13, wherein the solvent component S13 comprises a polar aprotic solvent. In some embodiments, the solvent component S13 comprises dimethylformamide.

In some embodiments, the compound of formula 17a, or a salt thereof, can prepared by a process comprising:
reacting a compound of formula 16a:

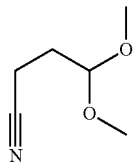

16a with ethyl acetate and a base B5 to form the compound of formula 17a.

In some embodiments, the base B5 is an alkali metal alkoxide. For example, the base B5 is potassium tert-butoxide. In some embodiments, from about 1 to about 3 molar equivalents of the base B5 is utilized relative to the compound of formula 16a. In some embodiments, from about 1 to about 2 molar equivalents of ethyl acetate is utilized relative to the compound of formula 16a. In some embodiments, about 2 molar equivalents of the base B5 is utilized relative to the compound of formula 16a. In some embodiments, the reacting of the compound of formula 17a with ethyl acetate and a base B5 is carried out at room temperature. In some embodiments, the reacting of the compound of formula 17a with ethyl acetate and a base B5 is carried out in a solvent component S14, wherein the solvent component S14 comprises an organic solvent. In some embodiments, the solvent component S14 comprises a di-$C_{1-6}$ alkyl ether or a 4-10 membered heterocycloalkyl ether. For example, the solvent component S14 comprises a tetrahydrofuran.

In some embodiments, the compound of formula 5a, or the salt thereof, can be prepared by a process comprising:
hydrolyzing a compound of formula 27a:

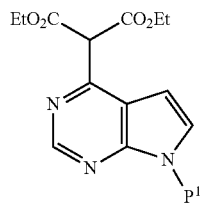

27a in water in the presence of a base B6.

In some embodiments, the base B6 is an alkali metal hydroxide. For example, the base B6 is sodium hydroxide. In some embodiments, from about 1 to about 2 molar equivalents of the base B6 is utilized relative to the compound of formula 27a. In some embodiments, about 1.5 molar equivalents of the base B6 is utilized relative to the compound of formula 27a. In some embodiments, the hydrolyzing of the compound of formula 27a is carried out at room temperature. In some embodiments, the hydrolyzing of the compound of formula 27a is carried out in a solvent component S15, wherein the solvent component S15 comprises an organic solvent. For example, the solvent component S15 comprises tetrahydrofuran, acetone, or a combination thereof.

In some embodiments, the compound of formula 5a, or the salt thereof, is the sodium salt of the compound of formula 5a. In some embodiments, the compound of formula 5a, or the salt thereof, is the compound of formula 5a.

In some embodiments, the compound of formula 5a can be prepared by a process comprising reacting the sodium salt of the compound of formula 5a with a strong acid A2. For example, the strong acid A2 is hydrochloric acid. In some embodiments, (a) the reacting of the sodium salt of compound of formula 5a with a strong acid A2 and (b) the hydrolyzing of the sodium salt of the compound of formula 27a is carried out in a single pot.

In some embodiments, the compound of formula 27a can be prepared by a process comprising:
reacting a compound of formula 26P:

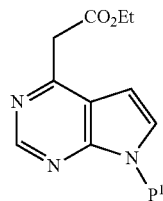

26P with a strong acid A3, wherein $P^1$ is an amino protecting group.

In some embodiments, $P^1$ is p-toluenesulfonyl. For example, A3 is hydrochloric acid. In some embodiments, the reacting of the compound of formula 26P with a strong acid A3 is carried out at room temperature. In some embodiments, the reacting of the compound of formula 26P with a strong acid A3 is carried out in a solvent component S16. In some embodiments, the solvent component S16 comprises formula $C_{1-6}$ alkyl-OH. In some embodiments, the solvent component S16 comprises ethanol.

In some embodiments, the compound of formula 26P can be prepared by a process comprising:
reacting a compound of formula 25P:

25P with alkali metal alkoxide B8 to form the compound of formula 26P, wherein $P^1$ is an amino protecting group.

In some embodiments, about 0.1 molar equivalents of alkali metal alkoxide B8 is utilized relative to the compound of formula 25P. In some embodiments, the reacting of the compound of formula 25P with alkali metal alkoxide B8 is carried out at room temperature. In some embodiments, the reacting of the compound of formula 25P with alkali metal alkoxide B8 is carried out in a solvent component S17, wherein the solvent component S17 comprises a polar protic solvent. For example, the alkali metal alkoxide B8 is sodium ethoxide. In some embodiments, the solvent component S17 comprises an alcohol. In some embodiments, the solvent component S17 comprises formula $C_{1-6}$ alkyl-OH. For example, the solvent component S17 comprises ethanol.

In some embodiments, the compound of formula 27a can be prepared by a process comprising:

reacting a compound of formula 25P:

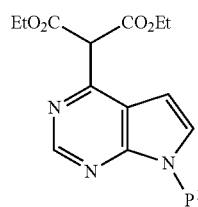

25P with an alkali metal alkoxide B9 to form the compound of formula 27a.

In some embodiments, from about 1 to about 2 molar equivalents of alkali metal alkoxide B9 is utilized relative to the compound of formula 25P. In some embodiments, about 1 molar equivalent of alkali metal alkoxide B9 is utilized relative to the compound of formula 25P. In some embodiments, the reacting of the compound of formula 25P with an alkali metal alkoxide B9 is carried out at a temperature of about 50° C. to about 80° C. In some embodiments, the reacting of the compound of formula 25P with an alkali metal alkoxide B9 is carried out in a solvent component S18, wherein the solvent component S18 comprises formula $C_{1-6}$ alkyl-OH. For example, the solvent component S18 comprises ethanol.

In some embodiments, the compound of formula 25P can be prepared by a process comprising:

reacting a compound of formula 2P:

2P with diethyl malonate and a base B10, wherein $P^1$ is an amino protecting group.

In some embodiments, the base B10 is an alkali metal carbonate. For example, the base B10 is cesium carbonate. In some embodiments, the reacting of the compound of formula 2P with a base B10 is carried out at a temperature of about 40° C. to about 70° C. In some embodiments, the reacting of the compound of formula 2P with a base B10 is carried out in a solvent component S19, wherein the solvent component S19 comprises a polar aprotic solvent. For example, the solvent component S19 comprises dimethylformamide.

In some embodiments, the compound of formula 2P can be prepared by a process comprising protecting a compound of formula 12a to form the compound of formula 2P. In some embodiments, the protecting comprise reacting the compound of formula 12a with a base B11 and $P^1$—Y, wherein Y is halo. For example, $P^1$ is p-toluenesulfonyl. In some embodiments, the base B11 is an alkali metal hydroxide. For example, the base B11 is sodium hydroxide. In some embodiments, the protecting comprise reacting the compound of formula 12a with a base B11 is carried out in a solvent component S20, wherein the solvent component S20 comprises a polar aprotic solvent. For example, the solvent component S20 comprises acetone.

In some embodiments, the compound of formula 12a can be prepared by a process comprising:

reacting a compound of formula 11a:

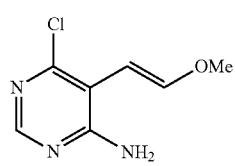

11a or a salt thereof, with a strong acid A4.

In some embodiments, the strong acid A4 is hydrochloric acid. In some embodiments, the reacting of the compound of formula 11a, or a salt thereof, with a strong acid A4 is carried out in a solvent component S21, wherein the solvent component S21 comprises a polar aprotic solvent. In some embodiments, the solvent component S21 comprises a di-$C_{1-6}$ alkyl ether or a 4-10 membered heterocycloalkyl ether. For example, the solvent component S21 comprises tetrahydrofuran. In some embodiments, the reacting of the compound of formula 11a, or a salt thereof, with a strong acid A4 is carried out at the refluxing temperature of tetrahydrofuran.

In some embodiments, the compound of formula 11a can be prepared by a process comprising:

reacting a compound of formula 10a:

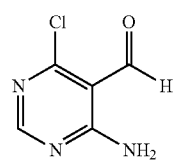

10a with (methoxymethyl)triphenylphosphonium chloride and a base B12.

In some embodiments, the base B12 is an alkali metal alkoxide. For example, the base B12 is potassium t-butoxide. In some embodiments, the reacting of the compound of formula 11a, or a salt thereof, with (methoxymethyl)triphenylphosphonium chloride and a base B12 is carried out at a temperature of about 10° C. to about 30° C. In some embodiments, the reacting of the compound of formula 11a, or a salt thereof, with (methoxymethyl)triphenylphosphonium chloride and a base B12 is carried out in a solvent component S22, wherein the solvent component S22 comprises a polar aprotic solvent. In some embodiments, the solvent component S22 comprises a di-$C_{1-6}$ alkyl ether or a 4-10 membered heterocycloalkyl ether. For example, the solvent component S22 comprises tetrahydrofuran.

In some embodiments, the compound of formula 10a can be prepared by a process comprising:

reacting a compound of formula 9a:

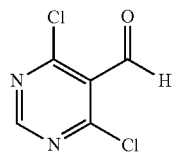

9a with ammonia.

In some embodiments, the reacting of the compound of formula 9a with ammonia is carried out at a temperature of about 40° C. to about 70° C. In some embodiments, the reacting of the compound of formula 9a with ammonia is carried out in a solvent component S23, wherein the solvent component S23 comprises organic solvent. For example, the solvent component S23 comprises toluene.

In some embodiments, the compound of formula 9a can be prepared by a process comprising:
reacting a compound of formula 8a:

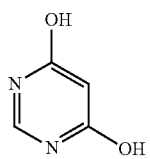

8a with a Vilsmeier reagent formed from dimethylformamide.

In some embodiments, the Vilsmeier reagent is prepared by a process comprising reacting dimethylformamide with a chlorinating agent. In some embodiments, the chlorinating agent is selected from oxalyl chloride, phosphorus oxychloride, triphosgene, thionyl chloride, sulfuryl chloride, and phosphorus pentachloride. For example, the chlorinating agent is phosphorus oxychloride. In some embodiments, about 4 to about 6 molar equivalents (e.g., 5 molar equivalents) of the chlorinating agent is utilized relative to a compound of formula 8a. In some embodiments, about 1 to about 3 molar equivalents (e.g., 2 molar equivalents) of the dimethylformamide is utilized relative to a compound of formula 8a. In some embodiments, the reacting dimethylformamide with a chlorinating agent is prepared at a temperature from about −10° C. to about 20° C. (e.g., about 0° C. to about 10° C.). In some embodiments, the reacting of a compound of formula 8a with a Vilsmeier reagent is carried out at a temperature from about 80° C. to about 130° C. (e.g., about 90° C. to about 120° C., or about 95° C. to about 115° C.).

In some embodiments, the compound of formula 12a can be prepared by a process comprising:
reacting a compound of formula 15a:

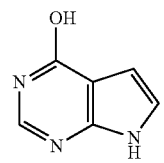

15a with a chlorinating agent.

In some embodiments, the chlorinating agent is selected from oxalyl chloride, phosphorus oxychloride, triphosgene, thionyl chloride, sulfuryl chloride, and phosphorus pentachloride. In some embodiments, the chlorinating agent is phosphorus oxychloride. In some embodiments, the reacting of the compound of formula 15a with a chlorinating agent is carried out at a temperature of about 50° C. to about 100° C. In some embodiments, the reacting of the compound of formula 15a with ammonia is carried out in a solvent component S24, wherein the solvent component S24 comprises an organic solvent. For example, the solvent component S24 comprises toluene.

In some embodiments, the compound of formula 15a can be prepared by a process comprising:
(i) reacting a compound of formula 14a:

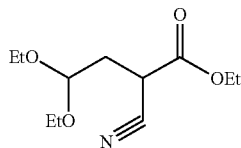

14a with formamidine acetate and an alkali metal hydroxide to generate a compound of formula 14aa:

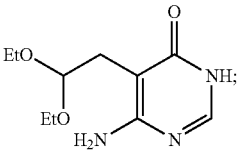

14aa and
(ii) reacting the compound of formula 14aa with a strong acid A4.

In some embodiments, the alkali metal hydroxide is sodium ethoxide. In some embodiments, the reacting of the compound of formula 14a with formamidine acetate and an alkali metal hydroxide is carried out at a temperature of about 50° C. to about 100° C. In some embodiments, the reacting of the compound of formula 14a with formamidine acetate and an alkali metal hydroxide is carried out in a solvent component S25, wherein the solvent component S25 comprises a polar protic solvent. In some embodiments, the solvent component S25 comprises an alcohol. In some embodiments, the solvent component S25 comprises formula $C_{1-6}$ alkyl-OH. For example, the solvent component S25 comprises ethanol. For example, the strong acid A4 is hydrochloric acid.

In some embodiments, the compound of formula 14a can be prepared by a process comprising:
reacting a compound of formula 13a:

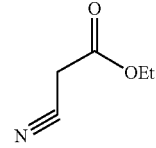

13a with bromoacetaldehyde diethyl acetal and sodium tert-amyloxide.

In some embodiments, the reacting of the compound of formula 13a with bromoacetaldehyde diethyl acetal and sodium tert-amyloxide is carried out at a temperature of about 80° C. to about 100° C. In some embodiments, the reacting of the compound of formula 13a with bromoacetaldehyde diethyl acetal and sodium tert-amyloxide is carried out in a solvent component S26, wherein the solvent component S26 comprises a polar aprotic solvent. In some embodiments, the solvent component S26 comprises dimethylsulfoxide.

In some embodiments, the compound of formula 3, or the salt thereof, is formed by a process comprising:

reacting a compound of formula A1:

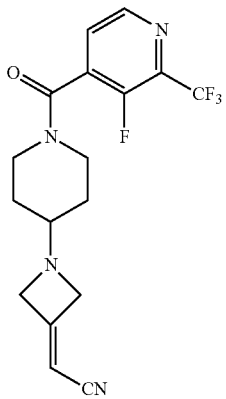

with hydrazine.

In some embodiments, the hydrazine is hydrazine hydrate.

In some embodiments, from about 1 to about 3 molar equivalents of hydrazine are utilized relative to the compound of formula A1. In some embodiments, from about 1.5 to about 2.5 molar equivalents of hydrazine are utilized relative to the compound of formula A1. In some embodiments, from about 2 to about 2.2 molar equivalents of hydrazine are utilized relative to the compound of formula A1. In some embodiments, about 2.1 molar equivalents of hydrazine are utilized relative to the compound of formula A1.

In some embodiments, the reacting of the compound of formula A1 is conducted in a solvent component S27. In some embodiments, the solvent component S27 comprises an organic solvent. In some embodiments, the solvent component S27 comprises an aprotic organic solvent.

In some embodiments, the solvent component S27 comprises acetonitrile.

In some embodiments, the reacting of the compound of formula A1 with hydrazine is conducted at a temperature of from about 20° C. to about 30° C. In some embodiments, the reacting of the compound of formula A1 with hydrazine is conducted at an ambient temperature.

In some embodiments, the compound of formula 50, or the salt thereof, is prepared by a process comprising:

reacting a compound of formula 54:

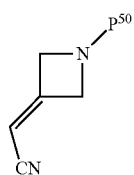

with hydrazine to form the compound of formula 50, or the salt thereof.

In some embodiments, the hydrazine is hydrazine hydrate.

In some embodiments, from about 1 to about 3 molar equivalents of hydrazine are utilized relative to the compound of formula 54. In some embodiments, from about 1.5 to about 2.5 molar equivalents of hydrazine are utilized relative to the compound of formula 54. In some embodiments, from about 2 to about 2.2 molar equivalents of hydrazine are utilized relative to the compound of formula 54. In some embodiments, about 2.1 molar equivalents of hydrazine are utilized relative to the compound of formula 54.

In some embodiments, the reacting of the compound of formula 54 is conducted in a solvent component S54. In some embodiments, the solvent component S54 comprises an organic solvent. In some embodiments, the solvent component S54 comprises an aprotic organic solvent.

In some embodiments, the solvent component S54 comprises acetonitrile.

In some embodiments, the reacting of the compound of formula 54 with hydrazine is conducted at a temperature of from about 20° C. to about 30° C. In some embodiments, the reacting of the compound of formula 54 with hydrazine is conducted at an ambient temperature.

Also provided herein is a compound of formula 50:

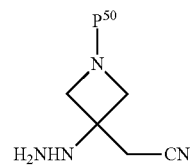

or a salt thereof, wherein $P^{50}$ is an amino protecting group.

In some embodiments, the compound of formula 50 is:

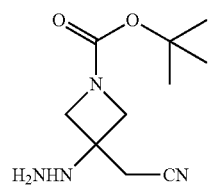

or a salt thereof.

Also provided herein is a compound of formula 3:

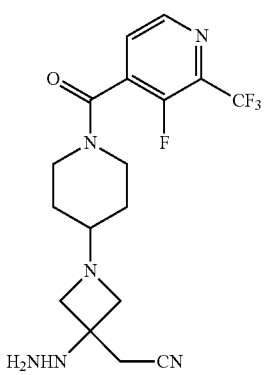

3 or a salt thereof.

In some embodiments, the compound of formula 1a or a salt thereof can be prepared by a process comprising:
reacting a compound of formula 12a:

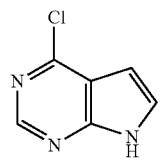

12a with t-butyldimethylsilyl chloride to generate a compound of formula 12b:

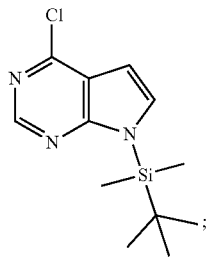

12b reacting the compound of formula 12b with MeMgBr in the presence of a Grignard catalyst to generate a compound of formula 12c:

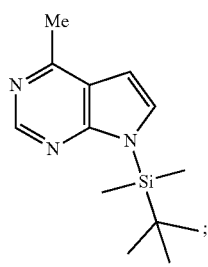

12c and
deprotecting the compound of formula 12c to generate a compound of formula 1a or a salt thereof.

In some embodiments, the compound of formula 1a or a salt thereof can be prepared by a process comprising:
reacting a compound of formula 22a:

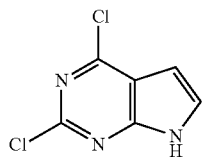

22a with t-butyldimethylsilyl chloride and MeMgBr in the presence of a Grignard catalyst to generate a compound of formula 23a:

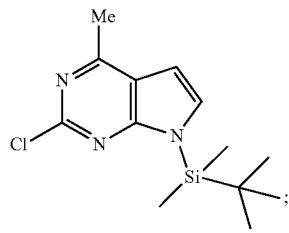

23a reacting the compound of formula 23a with hydrogen and palladium on carbon to generate a compound of formula 1a or a salt thereof.

In some embodiments, the process of preparing itacitinib, or a salt thereof, comprises reacting a salt of formula 2c:

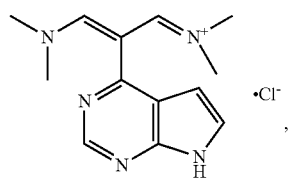

2c with a compound of formula 3:

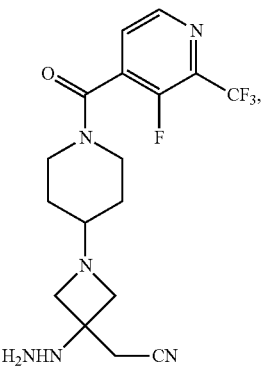

3 or a salt thereof, to form the itacitinib, or the salt thereof.
In some embodiments, the process of preparing itacitinib, or a salt thereof, comprises reacting a salt of formula 2c:

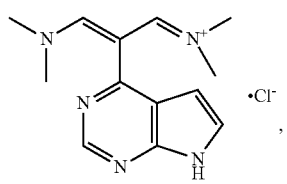

with a compound of formula 50:

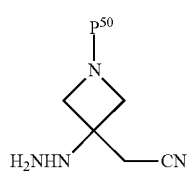

or a salt thereof, to form a compound of formula 51:

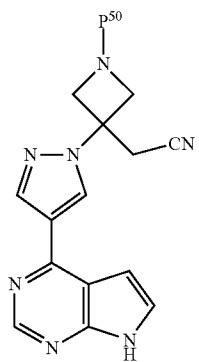

or a salt thereof, wherein $P^{50}$ is an amino protecting group;

deprotecting the compound of formula 51 to form a compound of formula 52:

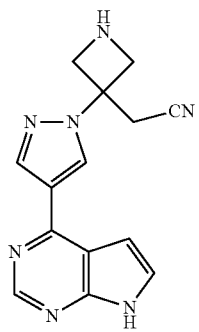

or a salt thereof; and reacting the compound of formula 52, or a salt thereof, with a compound of formula 53:

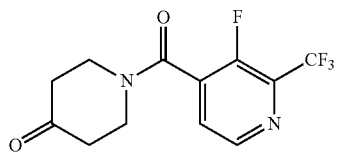

in the presence of coupling agent and a base to form itacitinib, or a salt thereof.

In some embodiments, the salt of formula 2c is prepared by a process comprising reacting a salt of formula 2d:

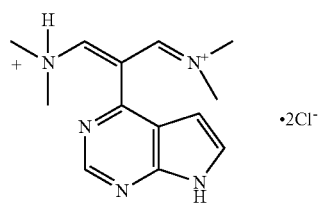

with a base to form the salt of formula 2c.

In some embodiments, the salt of formula 2d is prepared by a process comprising:

reacting a compound of formula 2P:

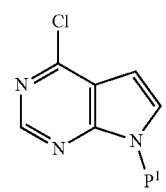

with MeMgBr in the presence of a Grignard catalyst to form a compound of formula 1aP:

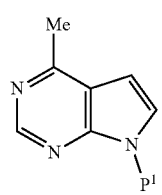

deprotecting the compound of formula 1aP to form a compound of formula 1a:

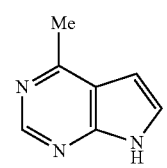

or a salt thereof; and reacting the compound of formula 1a, or the salt thereof, with a Vilsmeier reagent formed from dimethylformamide and a chlorinating agent to form the salt of formula 2d;

wherein $P^1$ is an amino protecting group.

In some embodiments, the salt of formula 2d is prepared by a process comprising:

reacting a compound of formula 22P:

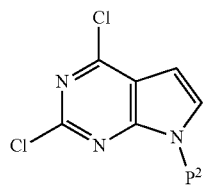

22P with MeMgBr in the presence of a Grignard catalyst to form a compound of formula 23P:

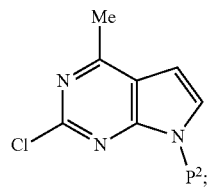

23P reducing the compound of formula 23P to form a compound of formula 1a:

1a or a salt thereof; and reacting the compound of formula 1a, or the salt thereof, with a Vilsmeier reagent formed from dimethylformamide and a chlorinating agent to form the salt of formula 2d;

wherein $P^2$ is an amino protecting group.

The present application further provides itacitinib, or a salt thereof, which is prepared according to a process provided herein.

The present application further provides a salt of itacitinib, which is prepared according to a process provided herein.

The present application further provides itacitinib, which is prepared according to a process provided herein.

The present application further provides itacitinib, or a pharmaceutically acceptable salt thereof, which is prepared according to a process provided herein.

The present application further provides a pharmaceutically acceptable salt of itacitinib, which is prepared according to a process provided herein.

The present application further provides itacitinib adipate, which is prepared according to a process provided herein.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

In some embodiments, the reagents or solvent components may be referred by by number (e.g., solvent component S1 or base B1). These numbers are present merely to further the antecedent basis for later dependent claim and therefore, in some embodiments, may be removed.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

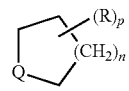

then it is understood that substituent R can occur p number of times on the ring, and R can be a different moiety at each occurrence. It is understood that each R group may replace any hydrogen atom attached to a ring atom, including one or both of the $(CH_2)_n$ hydrogen atoms. Further, in the above example, should the variable Q be defined to include hydrogens, such as when Q is the to be $CH_2$, NH, etc., any floating substituent such as R in the above example, can replace a hydrogen of the Q variable as well as a hydrogen in any other non-variable component of the ring.

As used herein, the term "alkyl", employed alone or in combination with other terms, refers to a saturated hydrocarbon group that may be straight-chain or branched. In some embodiments, the alkyl group contains 1 to 12, 1 to 8, or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl. In some embodiments, the alkyl moiety is methyl.

As used herein, the terms "halo" and "halogen", employed alone or in combination with other terms, refer to fluoro, chloro, bromo, and iodo.

As used herein, the term "4-10 membered heterocycloalkyl ether" refers to a non-aromatic ring or ring system, which optionally contain one or more alkenylene groups as part of the ring structure, which has at least one oxygen heteroatom ring member and 4-10 ring members. Included within the term "heterocycloalkyl" are monocyclic 4-, 5-, 6- and 7-membered heterocycloalkyl groups. Examples of 4-10 membered heterocycloalkyl ether include tetrahydrofuran, tetrahydropyran, dioxane, and the like.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, or spectrophotometry (e.g., UV-visible); or by chromatography such as high performance liquid chromatography (HPLC) or thin layer chromatography (TLC) or other related techniques.

As used herein, the terms "reacting" and "contacting" are used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

The compounds of the present invention also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof, and the like.

Suitable solvents can include ether solvents such as: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof, and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, mixtures thereof, and the like.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, hexamethylphosphoramide, mixtures thereof, and the like.

Suitable hydrocarbon solvents include benzene, cyclohexane, pentane, hexane, toluene, cycloheptane, methylcyclohexane, heptane (e.g., n-heptane), ethylbenzene, m-, o-, or p-xylene, octane, indane, nonane, naphthalene, mixtures thereof, and the like.

Supercritical carbon dioxide and ionic liquids can also be used as solvents.

The reactions of the processes described herein can be carried out at appropriate temperatures which can be readily determined by the skilled artisan. Reaction temperatures will depend on, for example, the melting and boiling points of the reagents and solvent, if present; thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to affect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid, and decanoic acid.

Example bases include alkali metal hydroxides (e.g., lithium hydroxide, sodium hydroxide, and potassium hydroxide), and alkali metal carbonate (e.g., lithium carbonate, sodium carbonate, and potassium carbonate). Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl, and cyclohexyl substituted amides.

The present invention also includes salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents. Lists of suitable salts are found in Remington's Pharmaceutical Sciences, 17th ed., Mack Publishing Company, Easton, Pa., 1985, p. 1418, the disclosure of which is hereby incorporated by reference in its entirety.

Upon carrying out preparation of compounds according to the processes described herein, the usual isolation and purification operations such as concentration, filtration, extraction, solid-phase extraction, recrystallization, chromatography, and the like may be used, to isolate the desired products.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

In some embodiments, itacitinib, intermediates for preparing itacitinib reagents, and salts thereof can include both anhydrous forms of that substance and solvated/hydrated forms of that substance. Different forms of the same substance have different bulk properties relating to, for example, hygroscopicity, solubility, stability, and the like. Forms with high melting points often have good thermodynamic stability which is advantageous in prolonging shelf-life drug formulations comprising the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage.

In some embodiments, the solid form of Compound 1, intermediates for preparing Compound 1, and salts thereof are crystalline. In some embodiments, a Compound 1 salt (e.g., Compound 1 phosphate) provided herein is crystalline. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

The different solid forms and salt forms thereof can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

Generally, the term "about" means±10%. In some embodiments, the term "about" means±5%.

In some embodiments, the solid forms and salt forms are substantially isolated. By "substantially isolated" is meant that the solid form, salt form or crystalline form thereof is at least partially or substantially separated from the environment in which it was formed or detected. Partial separation can include, for example, a composition enriched in the solid forms and salt forms. Substantial separation can include compositions containing at least about 50%, at least about 60%, at least about 70%, at least about 80%, at least about 90%, at least about 95%, at least about 97%, or at least about 99% by weight of the solid forms and salt forms. Methods for isolating solid forms and salt forms thereof are routine in the art.

In some embodiments, the solid forms and salt forms described herein can be found together with other substances such as water and solvents (e.g., hydrates and solvates) or can be isolated.

The phrase "pharmaceutically acceptable" is employed herein to refer to those salts, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The salt forming reactions described herein can be carried out at appropriate temperatures which can be readily determined by the skilled artisan. Reaction temperatures will depend on, for example, the melting and boiling points of the reagents and solvent, if present; thermodynamics of the reaction (e.g., vigorously exothermic reactions may need to be carried out at reduced temperatures); and the kinetics of the reaction (e.g., a high activation energy barrier may need elevated temperatures).

The expressions, "ambient temperature" and "room temperature" or "rt" as used herein, are understood in the art, and refer generally to a temperature, e.g., a reaction temperature, that is about the temperature of the room in which the reaction is carried out, for example, a temperature from about 20° C. to about 30° C.

The protecting groups (e.g., $P^1$ or $P^2$) described herein include, but are not limited to, the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. Examples of protecting group as described herein include $CH_2OC(=O)C(CH_3)_3$, $CH_2OCH_2CH_2Si(CH_3)_3$, benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), 2-tetrahydropyranyl (THP), tri($C_{1-4}$ alkyl)silyl (e.g., tri(isopropyl)silyl or t-butyldimethylsilyl), 1,1-diethoxymethyl, 2-(trimethylsilyl)ethoxymethyl (SEM), N-pivaloyloxymethyl (POM), p-nitrophenylsulfonyl, p-toluenesulfonyl, phenyl sulfonyl, methanesulfonyl, and the like. In some embodiments, the protecting group is tri($C_{1-4}$ alkyl) silyl (e.g., tri(isopropyl)silyl or t-butyldimethylsilyl). In some embodiments, the protecting group is t-butyldimethylsilyl. In some embodiments, the protecting group is p-toluenesulfonyl.

In some embodiments, one or more constituent atoms of the compounds (products or synthetic intermediates) presented herein can be replaced or substituted with isotopes of the atoms in natural or non-natural abundance. In some embodiments, the compound includes at least one deuterium atom. For example, in some embodiments one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1-2, 1-3, 1-4, 1-5, 1-6, 1-7, or 1-8 deuterium atoms.

In some embodiments, one or more hydrogen atoms of the itacitinib, or the salt thereof, are replaced by deuterium atoms.

In some embodiments, one or more hydrogen atoms of the compound of formula 3, or the salt thereof, are replaced by deuterium atoms.

In some embodiments, one or more hydrogen atoms of the compound of formula 50, or the salt thereof, are replaced by deuterium atoms.

In some embodiments, one or more hydrogen atoms of the compound of formula 51, or the salt thereof, are replaced by deuterium atoms.

Embodiments

1. A process of preparing itacitinib, or a salt thereof, comprising:

reacting a compound of formula 3:

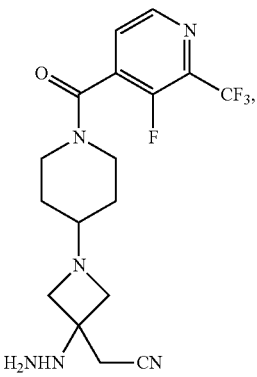

3 or a salt thereof, with a reagent selected from (i) a salt of formula 2a, and (ii) a compound of formula 2b:

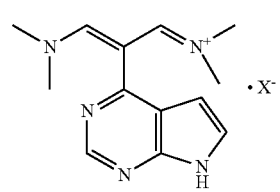

2a

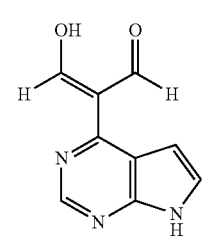

2b wherein $X^-$ is a counter anion.

2. The process of embodiment 1, wherein from about 1 to about 1.5 molar equivalents of the compound of formula 3, or the salt thereof, is utilized relative to the reagent.

3. The process of embodiment 1, wherein from about 1.2 to about 1.4 molar equivalents of the compound of formula 3, or the salt thereof, is utilized relative to the reagent.

4. The process of embodiment 1, wherein about 1.3 molar equivalents of the compound of formula 3, or the salt thereof, is utilized relative to the reagent.
5. The process of any one of embodiments 1 to 4, wherein the reacting of the reagent with the compound of formula 3, or the salt thereof, is carried out in a solvent component S1.
6. The process of embodiment 5, wherein the solvent component S1 comprises a polar protic solvent or a polar aprotic solvent.
7. The process of embodiment 5 or 6, wherein the solvent component S1 comprises an alcohol.
8. The process of any one of embodiments 5 to 7, wherein the solvent component S1 comprises formula $C_{1-6}$ alkyl-OH.
9. The process of any one of embodiments 5 to 8, wherein the solvent component S1 comprises ethanol.
10. The process of any one of embodiments 5 to 9, wherein the reacting of the compound of formula 3, or a salt thereof, with the reagent is conducted at a temperature of from about 20° C. to about 30° C.
11. The process of any one of embodiments 5 to 9, wherein the reacting of the compound of formula 3, or a salt thereof, with the reagent is conducted at an ambient temperature.
12. A process of preparing itacitinib, or a salt thereof, comprising: reacting a compound of formula 50:

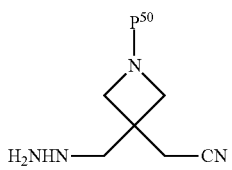

50 or a salt thereof, with a reagent selected from (i) a salt of formula 2a, and (ii) a compound of formula 2b:

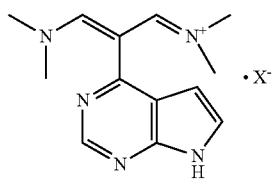

2a

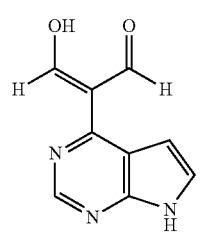

2b to form a compound of formula 51:

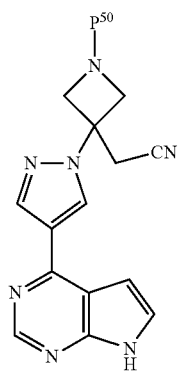

51 wherein $X^-$ is a counter anion; and $P^{50}$ is an amino protecting group.
13. The process of embodiment 12, wherein $P^{50}$ is selected from $R^{50}$—O—C(O)—, wherein $R^{50}$ is $C_{1-6}$ alkyl.
14. The process of embodiment 13, wherein $R^{50}$ is methyl, ethyl, propyl, isopropyl, butyl or t-butyl.
15. The process of embodiment 12, wherein $P^{50}$ is t-butyl-O—C(O)—.
16. The process of any one of embodiments 12 to 15, wherein from about 1 to about 1.5 molar equivalents of the compound of formula 50, or the salt thereof, is utilized relative to the reagent.
17. The process of any one of embodiments 12 to 15, wherein from about 1.2 to about 1.4 molar equivalents of the compound of formula 50, or the salt thereof, is utilized relative to the reagent.
18. The process of any one of embodiments 12 to 15, wherein about 1.3 molar equivalents of the compound of formula 50, or the salt thereof, is utilized relative to the reagent.
19. The process of any one of embodiments 12 to 18, wherein the reacting of the reagent with the compound of formula 50, or the salt thereof, is carried out in a solvent component S50.
20. The process of embodiment 19, wherein the solvent component S50 comprises a polar protic solvent or a polar aprotic solvent.
21. The process of embodiment 19 or 20, wherein the solvent component S50 comprises an alcohol.
22. The process of any one of embodiments 19 to 21, wherein the solvent component S50 comprises formula $C_{1-6}$ alkyl-OH.
23. The process of any one of embodiments 19 to 22, wherein the solvent component S50 comprises ethanol.
24. The process of any one of embodiments 12 to 23, wherein the reacting of the compound of formula 50, or a salt thereof, with the reagent is conducted at a temperature of from about 20° C. to about 30° C.
25. The process of any one of embodiments 12 to 23, wherein the reacting of the compound of formula 50, or a salt thereof, with the reagent is conducted at an ambient temperature.
26. The process of any one of embodiments 12 to 25, further comprising deprotecting the compound of formula 51 to form a compound of formula 52:

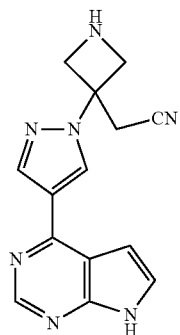

or a salt thereof.

27. The process of embodiment 26, wherein the deprotecting of the compound of formula 51 comprises treating the compound of formula 51 with a strong acid A51.
28. The process of embodiment 27, wherein the strong acid A51 is HCl.
29. The process of embodiment 28, wherein from about 5 to 10 molar equivalents of HCl are used relative to the compound of formula 51.
30. The process of embodiment 28, wherein from about 6 to 8 molar equivalents of HCl are used relative to the compound of formula 51.
31. The process of any one of embodiments 26 to 30, wherein the treating is conducted in a solvent component S51.
32. The process of embodiment 31, wherein the solvent component S51 comprises a polar protic solvent and an organic solvent.
33. The process of embodiment 31 or 32, wherein the solvent component S51 comprises, water, alcohol and halogenated hydrocarbon.
34. The process of any one of embodiments 31 to 33, wherein the alcohol of solvent component S50 comprises formula $C_{1-6}$ alkyl-OH.
35. The process of any one of embodiments 31 to 34, wherein the solvent component S51 comprises water, isopropanol, and dichloromethane.
36. The process of any one of embodiments 26 to 35, wherein the treating of the compound of formula 51 with a strong acid A51 is conducted at a reflux temperature.
37. The process of any one of embodiments 26 to 35, wherein the treating of the compound of formula 51 with a strong acid A51 is conducted at a temperature of from about 30° C. to about 60° C.
38. The process of any one of embodiments 26 to 35, wherein the treating of the compound of formula 51 with a strong acid A51 is conducted at a temperature of from about 35° C. to about 50° C.
39. The process of any one of embodiments 26 to 35, wherein the treating of the compound of formula 51 with a strong acid A51 is conducted at a temperature of from about 40° C. to about 45° C.
40. The process of any one of embodiments 26 to 39, wherein the compound of formula 52, or salt thereof, is the dihydrochloride salt of the compound of formula 52.
41. The process of any one of embodiments 26 to 40, further comprising reacting the compound of formula 52, or a salt thereof, with a compound of formula 53:

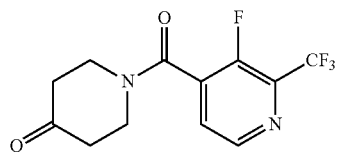

in the presence of coupling agent to form itacitinib.

42. The process of embodiment 41, wherein the coupling agent is sodium triacetoxyborohydride.
43. The process of embodiment 41 or 42, wherein the reacting of the compound of formula 52, or a salt thereof, with a compound of formula 53 is conducted in the presence of a base B53.
44. The process of embodiment 43, wherein the base B53 is a tertiary amine.
45. The process of embodiment 43 or 44, wherein the base B53 is a tri-($C_{1-6}$ alkyl)amine.
46. The process of any one of embodiments 43 to 45, wherein the base B53 is triethylamine.
47. The process of any one of embodiments 41 to 46, wherein from about 1 to about 1.5 molar equivalents of the compound of formula 53 are utilized relative to the compound of formula 52, or the salt thereof.
48. The process of any one of embodiments 41 to 46, wherein from about 1 to about 1.1 molar equivalents of the compound of formula 53 are utilized relative to the compound of formula 52, or the salt thereof.
49. The process of any one of embodiments 41 to 48, wherein from about 1 to about 3 molar equivalents of the coupling agent are utilized relative to the compound of formula 52, or the salt thereof.
50. The process of any one of embodiments 41 to 48, wherein about 2 molar equivalents of the coupling agent are utilized relative to the compound of formula 52, or the salt thereof.
51. The process of any one of embodiments 43 to 50, wherein from about 1 to about 3 molar equivalents of base B53 are utilized relative to the compound of formula 52, or the salt thereof.
52. The process of any one of embodiments 43 to 50, wherein about 2 molar equivalents of the base B53 are utilized relative to the compound of formula 52, or the salt thereof.
53. The process of any one of embodiments 41 to 52, wherein the reacting of the compound of formula 52, or a salt thereof, with a compound of formula 53 is conducted in a solvent component S52.
54. The process of embodiment 53, wherein the solvent component S52 comprises an organic solvent.
55. The process of embodiment 53 or 54, wherein the solvent component S52 comprises dichloromethane.
56. The process of any one of embodiments 41 to 55, wherein the reacting of the compound of formula 52, or a salt thereof, with a compound of formula 53 is conducted at a temperature of from about 20° C. to about 30° C.
57. The process of any one of embodiments 41 to 55, wherein the reacting of the compound of formula 52, or a salt thereof, with a compound of formula 53 is conducted at an ambient temperature.
58. The process of any one of embodiments 1 to 11 and 41 to 57, further comprising reacting itacitinib with at least one equivalent of adipic acid to form itacitinib adipate.

59. The process of any one of embodiments 1 to 58, wherein the reagent is the salt of formula 2a.
60. The process of any one of embodiments 1 to 59, wherein X⁻ is selected from Cl⁻, Br⁻, I⁻, BF₄⁻, PF₆⁻, AsF₆⁻, SbF₆⁻, and ClO₄⁻.
61. The process of any one of embodiments 1 to 59, wherein X⁻ is selected from Cl⁻, BF₄⁻, PF₆⁻, AsF₆⁻, SbF₆⁻, and ClO₄⁻.
62. The process of any one of embodiments 1 to 59, wherein X⁻ is BF₄⁻.
63. The process of any one of embodiments 1 to 59, wherein X⁻ is PF₆⁻.
64. The process of any one of embodiments 1 to 59, wherein X⁻ is AsF₆⁻.
65. The process of any one of embodiments 1 to 59, wherein X⁻ is SbF₆⁻.
66. The process of any one of embodiments 1 to 59, wherein X⁻ is ClO₄⁻.
67. The process of any one of embodiments 1 to 59, wherein X⁻ is Cl⁻.
68. The process of any one of embodiments 1 to 58, wherein the reagent is the compound of formula 2b.
69. The process of any one of embodiments 1 to 58 and 68, wherein the compound of formula 2b is prepared by a process comprising reacting the salt of formula 2a with a base B1.
70. The process of embodiment 69, wherein the reacting of the salt of formula 2a with the base B1 is conducted in a solvent component S2 comprising water.
71. The process of embodiment 69 or 70, wherein the base B1 is a strong base.
72. The process of any one of embodiments 69 to 71, wherein the base B1 is a hydroxide.
73. The process of any one of embodiments 69 to 72, wherein the base B1 is an alkali metal hydroxide.
74. The process of any one of embodiments 69 to 73, wherein the base B1 is sodium hydroxide.
75. The process of any one of embodiments 69 to 74, wherein from about 10 to about 15 molar equivalents of the base B1 is utilized relative to the salt of formula 2a, or salt thereof.
76. The process of any one of embodiments 69 to 74, wherein from about 12 molar equivalents of the base B1 is utilized relative to the salt of formula 2a, or salt thereof.
77. The process of any one of embodiments 69 to 76, wherein the reacting of the salt of formula 2a with the base B1 is conducted at a temperature of from about −10° C. to about 60° C.
78. The process of any one of embodiments 1 to 77, wherein the salt of formula 2a or the compound of formula 2b is prepared by a process comprising:
reacting the compound of formula 1a:

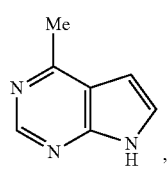

or a salt thereof, with a Vilsmeier reagent formed from dimethylformamide.

79. The process of any one of embodiments 1 to 77, wherein the salt of formula 2a or the compound of formula 2b is prepared by a process comprising:
reacting the compound of formula 5a:

or a salt thereof, with a Vilsmeier reagent formed from dimethylformamide.
80. The process of embodiment 79, wherein the compound of formula 5a, or the salt thereof, is a salt.
81. The process of embodiment 79 or 80, wherein the compound of formula 5a, or the salt thereof, is the sodium salt.
82. The process of any one of embodiments 78 to 81, wherein the reacting with the Vilsmeier reagent produces a compound of formula 2c:

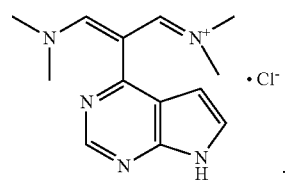

83. The process of embodiment 82, wherein after the reacting with a Vilsmeier reagent, the compound of formula 2c is reacted with a salt of formula M⁺X⁻, wherein M⁺ is a counter cation.
84. The process of any one of embodiments 78 to 83, wherein the Vilsmeier reagent is prepared by a process comprising reacting dimethylformamide with a chlorinating agent.
85. The process of embodiment 84, wherein the chlorinating agent is selected from oxalyl chloride, phosphorus oxychloride, triphosgene, thionyl chloride, sulfuryl chloride, and phosphorus pentachloride.
86. The process of embodiment 84, wherein the chlorinating agent is selected from oxalyl chloride, phosphorus oxychloride, and triphosgene.
87. The process of embodiment 84, wherein the chlorinating agent is oxalyl chloride.
88. The process of embodiment 84, wherein the chlorinating agent is phosphorus oxychloride.
89. The process of embodiment 84, wherein the chlorinating agent is triphosgene.
90. The process of any one of embodiments 84 to 89, wherein from about 1 to about 5 molar equivalents of the chlorinating agent are utilized relative to the compound of formula 1a or 5a, or the salt thereof.
91. The process of any one of embodiments 84 to 89, wherein from about 1 to about 4 molar equivalents of the chlorinating agent are utilized relative to the compound of formula 1a or 5a, or the salt thereof.
92. The process of any one of embodiments 84 to 89, wherein from about 1 to about 3 molar equivalents of the chlorinating agent are utilized relative to the compound of formula 1a or 5a, or the salt thereof.

93. The process of any one of embodiments 78 to 92, wherein from about 10 to about 25 molar equivalents of dimethylformamide are utilized relative to the compound of formula 1a or 5a, or the salt thereof.

94. The process of any one of embodiments 78 to 92, wherein from about 10 to about 20 molar equivalents of dimethylformamide are utilized relative to the compound of formula 1a or 5a, or the salt thereof.

95. The process of any one of embodiments 78 to 92, wherein from about 10 to about 15 molar equivalents of dimethylformamide are utilized relative to the compound of formula 1a or 5a, or the salt thereof.

96. The process of any one of embodiments 78 to 92, wherein from about 11 to about 14 molar equivalents of dimethylformamide are utilized relative to the compound of formula 1a or 5a, or the salt thereof.

97. The process of any one of embodiments 78 to 92, wherein from about 11 to about 13 molar equivalents of dimethylformamide are utilized relative to the compound of formula 1a or 5a, or the salt thereof.

98. The process of any one of embodiments 78 to 97, wherein the preparation of the Vilsmeier reagent is carried out in a solvent component S3.

99. The process of embodiment 98, wherein the solvent component S3 comprises an organic solvent.

100. The process of embodiment 98 or 99, wherein the solvent component S3 comprises a polar aprotic solvent.

101. The process of any one of embodiments 98 to 100, wherein the solvent component S3 comprises acetonitrile, dimethylformamide, or a combination thereof.

102. The process of any one of embodiments 78 to 101, wherein the Vilsmeier reagent is prepared at a temperature between from about −10° C. to about 60° C.

103. The process of any one of embodiments 78 to 101, wherein the Vilsmeier reagent is prepared at a temperature between from about −10° C. to about 30° C.

104. The process of any one of embodiments 78 to 101, wherein the Vilsmeier reagent is prepared at a temperature between from about room temperature to about 60° C.

105. The process of any one of embodiments 78 to 101, wherein the reacting of the compound of formula 1a or 5a, or the salt thereof, with the Vilsmeier reagent is carried out at a temperature of from about 40° C. to about 100° C.

106. The process of any one of embodiments 78 to 101, wherein the reacting of the compound of formula 1a or 5a, or the salt thereof, with the Vilsmeier reagent is carried out at a temperature of from about 70° C. to about 100° C.

107. The process of any one of embodiments 78 to 101, wherein the reacting of the compound of formula 1a or 5a, or the salt thereof, with the Vilsmeier reagent is carried out at a temperature of from about 40° C. to about 60° C.

108. The process of any one of embodiments 78 to 107, wherein the product of the reacting with the Vilsmeier reagent has formula 2d:

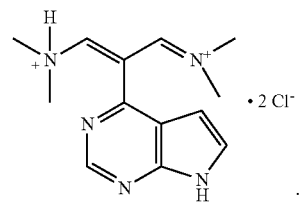

109. The process of any one of embodiments 1 to 77, wherein the salt of formula 2a is formed by a process comprising:
reacting the salt of formula 2c:

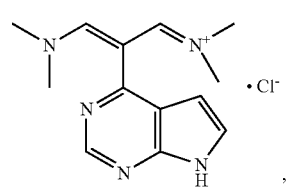

with a salt of formula M⁺X⁻, wherein:
M⁺ is a counter cation; and
X⁻ is a counter anion other than Cl⁻.

110. The process of embodiment 109, wherein M⁺ is an alkali metal counter cation.

111. The process of embodiment 109 or 110, wherein M⁺ is Li⁺, Na⁺ or K⁺.

112. The process of embodiment 109 or 110, wherein M⁺ is Na⁺.

113. The process of any one of embodiments 109 to 112, wherein X⁻ is selected from Br⁻, I⁻, BF$_4^-$, PF$_6^-$, AsF$_6^-$, SbF$_6^-$, or ClO$_4^-$.

114. The process of any one of embodiments 109 to 113, wherein the salt of formula 2c is produced by a process comprising:
reacting a salt of formula 2d:

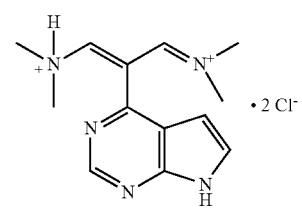

with a base.

115. The process of embodiment 114, wherein the compound of formula 2b is prepared by a process comprising reacting a salt of formula 2d with a base B2.

116. The process of embodiment 115, wherein (i) the reacting of the salt of formula 2d with a base B2 and (ii) the reacting of the salt of formula 2a with the compound of formula 3 are conducted in a single pot.

117. The process of embodiment 115 or 116, wherein the reacting of the salt of formula 2d with a base B2 is conducted in a solvent component comprising water.

118. The process of any one of embodiments 115 to 117, wherein the base B2 is a strong base.

119. The process of any one of embodiments 115 to 118, wherein the base B2 is a hydroxide base.
120. The process of any one of embodiments 115 to 119, wherein the base B2 is an alkali metal hydroxide.
121. The process of any one of embodiments 115 to 120, wherein the base B2 is sodium hydroxide.
122. The process of any one of embodiments 115 to 121, wherein the reacting of the salt of formula 2d with a base B2 is conducted at a temperature of from about −10° C. to about 15° C.
123. The process of any one of embodiments 78 and 84 to 122, wherein the compound of formula 1a, or the salt thereof, is the hydrochloride salt.
124. The process of any one of embodiments 78 and 84 to 123, wherein the compound of formula 1a, or the salt thereof, is prepared by a process comprising:
deprotecting a compound of formula 1aP:

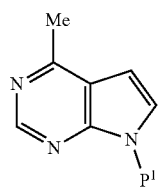

wherein $P^1$ is an amino protecting group.
125. The process of embodiment 124, wherein $P^1$ is selected from $(R^1)_3Si$, wherein $R^1$ is $C_{1-6}$ alkyl.
126. The process of embodiment 125, wherein $R^1$ is methyl, ethyl, propyl, isopropyl, butyl or t-butyl.
127. The process of embodiment 124, wherein $P^1$ is t-butyldimethylsilyl.
128. The process of any one of embodiments 124 to 127, wherein the deprotecting is carried out by reacting the compound of formula 1aP with a base B3.
129. The process of embodiment 128, wherein the base B3 is a hydroxide base.
130. The process of embodiment 128 or 129, where the base B3 is ammonium hydroxide.
131. The process of any one of embodiments 128 to 130, wherein the deprotecting is carried out in a solvent component S4.
132. The process of embodiment 131, wherein the solvent component S4 comprises a polar protic solvent.
133. The process of embodiment 131 or 132, wherein the solvent component S4 comprises an alcohol.
134. The process of any one of embodiments 131 to 133, wherein the solvent component S4 comprises formula $C_{1-6}$ alkyl-OH.
135. The process of any one of embodiments 131 to 134, wherein the solvent component S4 comprises methanol.
136. The process of any one of embodiments 124 to 135, wherein the compound of formula 1aP is prepared by a process comprising:
reacting a compound of formula 2P:

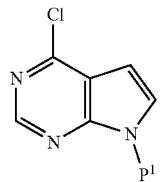

with MeMgBr in the presence of a Grignard catalyst, wherein $P^1$ is an amino protecting group.
137. The process of embodiment 136, wherein the catalyst is an iron catalyst.
138. The process of embodiment 137, wherein the iron catalyst is iron(III) acetylacetonate.
139. The process of any one of embodiments 136 to 138, wherein from about 1 to about 2 molar equivalents of MeMgCl are utilized relative to the compound of formula 2P.
140. The process of any one of embodiments 136 to 139, wherein from about 1% to about 10% molar equivalents of the catalyst are utilized relative to the compound of formula 2P.
141. The process of any one of embodiments 136 to 140, wherein the reacting of the compound formula 2P with MeMgCl is carried out in a solvent component S5.
142. The process of embodiment 141, wherein the solvent component S5 comprises a di-$C_{1-6}$ alkyl ether or a 4-10 membered heterocycloalkyl ether.
143. The process of embodiment 141 or 142, wherein the solvent component S5 comprises a tetrahydrofuran.
144. The process of any one of embodiments 136 to 143, wherein the reacting of the compound formula 2P with MeMgCl is carried out at a temperature of from about −10° C. to about 30° C.
145. The process of any one of embodiments 136 to 144, wherein the compound of formula 2P is prepared by a process comprising:
protecting a compound of formula 12a:

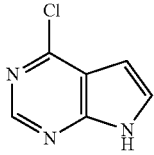

to form the compound of formula 2P.
146. The process of embodiment 145, wherein the protecting comprise reacting the compound of formula 12a with an alkali metal hydride and $P^1$—Y, wherein Y is halo.
147. The process of embodiment 146, wherein $P^1$—Y is $(R^1)_3Si$—Y, wherein Y is halo and $R^1$ is $C_{1-6}$ alkyl.
148. The process of embodiment 147, wherein $P^1$ is $(R^1)_3Si$, wherein $R^1$ is $C_{1-6}$ alkyl.
149. The process of embodiment 147 or 148, wherein $R^1$ is methyl, ethyl, propyl, isopropyl, butyl or t-butyl.
150. The process of embodiment 146, wherein $P^1$ is t-butyldimethylsilyl.
151. The process of any one of embodiments 146 to 150, wherein the alkali metal hydride is sodium hydride.

152. The process of any one of embodiments 146 to 151, wherein from about 1 to about 2 molar equivalents of the alkali metal hydride is utilized relative to the compound of formula 12a.

153. The process of any one of embodiments 146 to 152, wherein from about 1 to about 2 molar equivalents of $P^1$—Y is utilized relative to the compound of formula 12a.

154. The process of any one of embodiments 146 to 153, wherein the reacting of the compound of formula 12a with the alkali metal hydride and $P^1$—Y is carried out at a temperature of about −10° C. to about 20° C.

155. The process of any one of embodiments 146 to 154, wherein the reacting of the compound of formula 12a with the alkali metal hydride and $P^1$—Y is carried out in a solvent component S6, wherein the solvent component S6 comprises an organic solvent.

156. The process of embodiment 155, wherein the solvent component S6 comprises a di-$C_{1-6}$ alkyl ether or a 4-10 membered heterocycloalkyl ether.

157. The process of embodiment 155 or 156, wherein the solvent component S6 comprises a tetrahydrofuran.

158. The process of any one of embodiments 78 and 84 to 123, wherein the compound of formula 1a, or the salt thereof, is prepared by a process comprising:
reducing a compound of formula 23P:

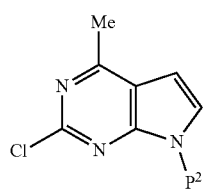

wherein $P^2$ is an amino protecting group.

159. The process of embodiment 158, wherein the reducing of the compound of formula 23P is accomplished by a process comprising reacting the compound of formula 23P with hydrogen gas in the presence of a catalyst.

160. The process of embodiment 159, wherein the catalyst is $Pd^0$ on carbon.

161. The process of embodiment 159 or 160, wherein the amount of the catalyst relative to the compound of formula 23P is about 5% to about 15% by weight.

162. The process of any one of embodiments 159 to 161, wherein the reacting of the compound of formula 23P with hydrogen and the catalyst is carried out at a temperature of about 40° C. to about 70° C.

163. The process of any one of embodiments 159 to 162, wherein the reacting of the compound of formula 23aP with hydrogen and the catalyst is carried out in a solvent component S7.

164. The process of embodiment 163, wherein the solvent component S7 comprises a polar protic solvent.

165. The process of embodiment 163 or 164, wherein the solvent component S7 comprises an alcohol.

166. The process of any one of embodiments 163 to 165, wherein the solvent component S7 comprises formula $C_{1-6}$ alkyl-OH.

167. The process of any one of embodiments 163 to 166, wherein the solvent component S7 comprises methanol.

168. The process of any one of embodiments 158 to 167, wherein the compound of formula 23P is prepared by a process comprising:
reacting a compound of formula 22P:

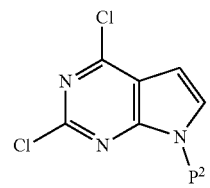

with MeMgBr in the presence of a Grignard catalyst, wherein $P^2$ is an amino protecting group.

169. The process of embodiment 168, wherein the catalyst is an iron catalyst.

170. The process of embodiment 169, wherein the iron catalyst is iron(III) acetylacetonate.

171. The process of any one of embodiments 168 to 170, wherein from about 1 to about 2 molar equivalents of MeMgCl is utilized relative to the compound of formula 22P.

172. The process of any one of embodiments 168 to 171, wherein from about 1% to about 10% molar equivalents of the catalyst are utilized relative to the compound of formula 22P.

173. The process of any one of embodiments 168 to 172, wherein the reacting of the compound formula 22P with MeMgCl is carried out in a solvent component S8.

174. The process of embodiment 173, wherein the solvent component S8 comprises a di-$C_{1-6}$ alkyl ether or a 4-10 membered heterocycloalkyl ether.

175. The process of embodiment 173 or 174, wherein the solvent component S8 comprises a tetrahydrofuran.

176. The process of any one of embodiments 168 to 175, wherein the reacting of the compound formula 2P with MeMgCl is carried out at a temperature of from about −10° C. to about 30° C.

177. The process of any one of embodiments 168 to 176, wherein the compound of formula 22P is prepared by a process comprising:
protecting a compound of formula 22a:

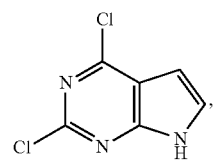

to form the compound of formula 22P.

178. The process of embodiment 177, wherein the protecting comprise reacting the compound of formula 22a with an alkali metal hydride and $P^2$—Y, wherein Y is halo.

179. The process of embodiment 178, wherein $P^2$ is $(R^1)_3Si$, wherein $R^1$ is $C_{1-6}$ alkyl.

180. The process of embodiment 179, wherein $R^1$ is methyl, ethyl, propyl, isopropyl, butyl or t-butyl.

181. The process of embodiment 178, wherein $P^2$ is t-butyldimethylsilyl.

182. The process of any one of embodiments 178 to 181, wherein the alkali metal hydride is sodium hydride.
183. The process of any one of embodiments 178 to 182, wherein from about 1 to about 2 molar equivalents of the alkali metal hydride is utilized relative to the compound of formula 22a.
184. The process of any one of embodiments 178 to 183, wherein from about 1 to about 2 molar equivalents of P$^2$—Y is utilized relative to the compound of formula 22a.
185. The process of any one of embodiments 178 to 184, wherein the reacting of the compound of formula 22a with the alkali metal hydride and P$^2$—Y is carried out at a temperature of about −10° C. to about 20° C.
186. The process of any one of embodiments 178 to 185, wherein the reacting of the compound of formula 22a with the alkali metal hydride and P$^2$—Y is carried out in a solvent component S9, wherein the solvent component S9 comprises an organic solvent.
187. The process of embodiment 186, wherein the solvent component S9 comprises a di-C$_{1-6}$ alkyl ether or a 4-10 membered heterocycloalkyl ether.
188. The process of embodiment 186 or 187, wherein the solvent component S9 comprises a tetrahydrofuran.
189. The process of any one of embodiments 78 and 84 to 123, wherein the compound of formula 1a, or the salt thereof, is prepared by a process comprising:
reacting a compound of formula 18a:

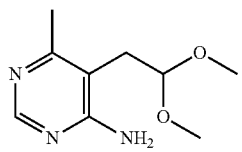

18a with an acid A1 to form the compound of formula 1a.
190. The process of embodiment 189, wherein the acid A1 is a strong acid.
191. The process of embodiment 189 or 190, wherein the acid A1 is hydrochloric acid.
192. The process of any one of embodiments 189 to 191, wherein the reacting of the compound of formula 18a with the acid A1 is carried out in a solvent component S10, wherein the solvent component S10 comprises a polar protic solvent.
193. The process of embodiment 192, wherein the solvent component S10 comprises an alcohol.
194. The process of embodiment 192 or 193, wherein the solvent component S10 comprises formula C$_{1-6}$ alkyl-OH.
195. The process of any one of embodiments 192 to 194, wherein the solvent component S10 comprises isopropyl alcohol.
196. The process of any one of embodiments 189 to 195, wherein the compound of formula 18a, or a salt thereof, is prepared by a process comprising:
reacting a compound of formula 17a:

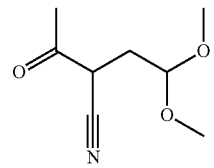

17a with formamidine acetate and triethyl orthoformate to form the compound of formula 17a.
197. The process of embodiment 196, wherein from about 10 to about 15 molar equivalents of formamidine acetate is utilized relative to the compound of formula 17a is about 10 to about 15.
198. The process of embodiment 196 or 197, wherein from about 6 to about 10 molar equivalents of triethyl orthoformate is utilized relative to the compound of formula 17a.
199. The process of any one of embodiments 196 to 198, wherein the reacting of the compound of formula 17a with formamidine acetate and triethyl orthoformate is carried out at a temperature of about 100° C. to about 150° C.
200. The process of any one of embodiments 196 to 199, wherein the reacting of the compound of formula 17a with formamidine acetate and triethyl orthoformate is carried out in a solvent component S11, wherein the solvent component S11 comprises a polar protic solvent.
201. The process of embodiment 200, wherein the solvent component S11 comprises an alcohol.
202. The process of embodiment 200 or 201, wherein the solvent component S11 comprises formula C$_{1-6}$ alkyl-OH.
203. The process of any one of embodiments 200 to 202, wherein the solvent component S11 comprises 1-butanol.
204. The process of any one of embodiments 196 to 203, wherein the compound of formula 17a, or a salt thereof, is prepared by a process comprising:
reacting a compound of formula 20a:

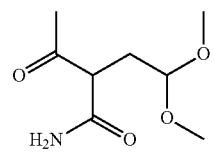

20a with a compound of formula 21a:

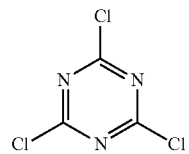

21a to form the compound of formula 17a.
205. The process of embodiment 204, wherein from about 0.4 to about 1 molar equivalents of the compound of formula 21a is utilized relative to the compound of formula 20a.

206. The process of embodiment 204 or 205, wherein the reacting of the compound of formula 20a with the compound of formula 21a is carried out at room temperature.
207. The process of any one of embodiments 204 to 206, wherein the reacting of the compound of formula 20a with the compound of formula 21a is carried out in a solvent component S12, wherein the solvent component S12 comprises a polar aprotic solvent.
208. The process of embodiment 207, wherein the solvent component S12 comprises dimethylformamide.
209. The process of any one of embodiments 204 to 208, wherein the compound of formula 20a, or a salt thereof, is prepared by a process comprising:
reacting a compound of formula 19a:

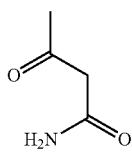

19a with bromo-1,1-dimethoxyethane and a base B4 to form the compound of formula 20a.
210. The process of embodiment 209, wherein the base B4 is an alkali metal carbonate.
211. The process of embodiment 209 or 210, wherein the base B4 is cesium carbonate.
212. The process of any one of embodiments 209 to 211, wherein from about 1 to about 2 molar equivalents of the base B4 is utilized relative to the compound of formula 19a.
213. The process of any one of embodiments 209 to 212, wherein from about 1 to about 2 molar equivalents of bromo-1,1-dimethoxyethane is utilized relative to the compound of formula 19a.
214. The process of any one of embodiments 209 to 213, wherein the reacting of the compound of formula 19a with bromo-1,1-dimethoxyethane is carried out at a temperature of about 70° C. to about 100° C.
215. The process of any one of embodiments 209 to 214, wherein the reacting of the compound of formula 19a with bromo-1,1-dimethoxyethane is carried out in a solvent component S13, wherein the solvent component S13 comprises a polar aprotic solvent.
216. The process of embodiment 215, wherein the solvent component S13 is dimethylformamide.
217. The process of any one of embodiments 209 to 216, wherein the compound of formula 17a, or a salt thereof, is prepared by a process comprising:
reacting a compound of formula 16a:

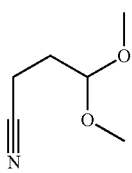

16a with ethyl acetate and a base B5 to form the compound of formula 17a.

218. The process of embodiment 217, wherein the base B5 is an alkali metal alkoxide.
219. The process of embodiment 217 or 218, wherein the base B5 is potassium tert-butoxide.
220. The process of any one of embodiments 217 to 219, wherein from about 1 to about 3 molar equivalents of the base B5 is utilized relative to the compound of formula 16a.
221. The process of any one of embodiments 217 to 220, wherein from about 1 to about 2 molar equivalents of ethyl acetate is utilized relative to the compound of formula 16a.
222. The process of any one of embodiments 217 to 221, wherein the reacting of the compound of formula 17a with ethyl acetate and a base B5 is carried out at room temperature.
223. The process of any one of embodiments 217 to 222, wherein the reacting of the compound of formula 17a with ethyl acetate and a base B5 is carried out in a solvent component S14, wherein the solvent component S14 comprises an organic solvent.
224. The process of embodiment 223, wherein the solvent component S14 comprises a di-$C_{1-6}$ alkyl ether or a 4-10 membered heterocycloalkyl ether.
225. The process of embodiment 223 or 224, wherein the solvent component S14 comprises a tetrahydrofuran.
226. The process of any one of embodiments 79 to 123, wherein the compound of formula 5a, or the salt thereof, is prepared by a process comprising:
hydrolyzing a compound of formula 27a:

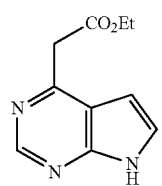

27a in water in the presence of a base B6.
227. The process of embodiment 226, wherein the base B6 is an alkali metal hydroxide.
228. The process of embodiment 227, wherein the base B6 is sodium hydroxide.
229. The process of any one of embodiments 226 to 228, wherein from about 1 to about 2 molar equivalents of the base B6 is utilized relative to the compound of formula 27a.
230. The process of any one of embodiments 226 to 229, wherein the hydrolyzing of the compound of formula 27a is carried out at room temperature.
231. The process of any one of embodiments 226 to 230, wherein the hydrolyzing of the compound of formula 27a is carried out in a solvent component S15, wherein the solvent component S15 comprises an organic solvent.
232. The process of embodiment 231, wherein the solvent component S15 comprises tetrahydrofuran, acetone, or a combination thereof.
233. The process of any one of embodiments 79 to 90, 98 to 104, 108, and 226 to 232, wherein the compound of formula 5a, or the salt thereof, is the sodium salt of the compound of formula 5a.

234. The process of any one of embodiments 79 to 90, 98 to 104, 108, and 226 to 233, wherein the compound of formula 5a, or the salt thereof, is the compound of formula 5a.
235. The process of embodiment 234, wherein the compound of formula 5a is prepared by a process comprising reacting the sodium salt of the compound of formula 5a with a strong acid A2.
236. The process of embodiment 235, wherein the strong acid A2 is hydrochloric acid.
237. The process of embodiment 235 or 236, wherein (a) the reacting of the sodium salt of compound of formula 5a with a strong acid A2 and (b) the hydrolyzing of the sodium salt of the compound of formula 27a is carried out in a single pot.
238. The process of any one of embodiments 226 to 237, wherein the compound of formula 27a is prepared by a process comprising:
reacting a compound of formula 26P:

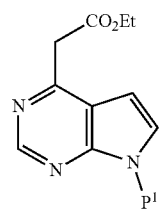

26P with a strong acid A3, wherein $P^1$ is an amino protecting group.
239. The process of embodiment 238, wherein $P^1$ is p-toluenesulfonyl 240. The process of embodiment 238 or 239, wherein A3 is hydrochloric acid.
241. The process of any one of embodiments 238 to 240, wherein the reacting of the compound of formula 26P with a strong acid A3 is carried out at room temperature.
242. The process of any one of embodiments 238 to 241, wherein the reacting of the compound of formula 26P with a strong acid A3 is carried out in a solvent component S16.
243. The process of embodiment 242, wherein the solvent component S16 comprises formula $C_{1-6}$ alkyl-OH.
244. The process of embodiment 242 or 243, wherein the solvent component S16 comprises ethanol.
245. The process of any one of embodiments 238 to 244, wherein the compound of formula 26P is prepared by a process comprising:
reacting a compound of formula 25P:

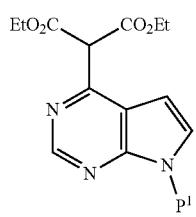

25P with alkali metal alkoxide B8 to form the compound of formula 26P, wherein $P^1$ is an amino protecting group.

246. The process of embodiment 245, wherein about 0.1 molar equivalents of alkali metal alkoxide B8 is utilized relative to the compound of formula 25P.
247. The process of embodiments 245 or 246, wherein the reacting of the compound of formula 25P with alkali metal alkoxide B8 is carried out at room temperature.
248. The process of any one of embodiments 245 to 247, wherein the reacting of the compound of formula 25P with alkali metal alkoxide B8 is carried out in a solvent component S17, wherein the solvent component S17 comprises a polar protic solvent.
249. The process of any one of embodiments 245 to 248, wherein the alkali metal alkoxide B8 is sodium ethoxide.
250. The process of embodiment 248 or 249, wherein the solvent component S17 comprises an alcohol.
251. The process of any one of embodiments 248 to 250, wherein the solvent component S17 comprises formula $C_{1-6}$ alkyl-OH.
252. The process of any one of embodiments 248 to 250, wherein the solvent component S17 comprises ethanol.
253. The process of any one of embodiments 226 to 237, wherein the compound of formula 27a is prepared by a process comprising:
reacting a compound of formula 25P:

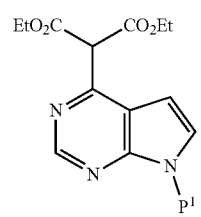

25P with an alkali metal alkoxide B9 to form the compound of formula 27a.
254. The process of embodiment 253, wherein from about 1 to about 2 molar equivalents of alkali metal alkoxide B9 is utilized relative to the compound of formula 25P.
255. The process of embodiment 253, wherein about 1 molar equivalent of alkali metal alkoxide B9 is utilized relative to the compound of formula 25P.
256. The process of any one of embodiments 253 to 255, wherein the reacting of the compound of formula 25P with an alkali metal alkoxide B9 is carried out at a temperature of about 50° C. to about 80° C.
257. The process of any one of embodiments 253 to 256, wherein the reacting of the compound of formula 25P with an alkali metal alkoxide B9 is carried out in a solvent component S18, wherein the solvent component S18 comprises formula $C_{1-6}$ alkyl-OH.
258. The process of embodiment 257, wherein the solvent component S18 comprises ethanol.
259. The process of any one of embodiments 253 to 258, wherein the compound of formula 25P is prepared by a process comprising:

reacting a compound of formula 2P:

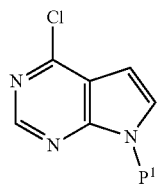

with diethyl malonate and a base B10, wherein $P^1$ is an amino protecting group.
260. The process of embodiment 259, wherein the base B10 is an alkali metal carbonate.
261. The process of embodiment 259 or 260, wherein the base B10 is cesium carbonate.
262. The process of any one of embodiments 259 to 261, wherein the reacting of the compound of formula 2P with a base B10 is carried out at a temperature of about 40° C. to about 70° C.
263. The process of any one of embodiments 259 to 262, wherein the reacting of the compound of formula 2P with a base B10 is carried out in a solvent component S19, wherein the solvent component S19 comprises a polar aprotic solvent.
264. The process of embodiment 263, wherein the solvent component S19 comprises dimethylformamide.
265. The process of any one of embodiments 259 to 264, wherein the compound of formula 2P is prepared by a process comprising protecting a compound of formula 12a to form the compound of formula 2P.
266. The process of embodiment 265, wherein the protecting comprise reacting the compound of formula 12a with a base B11 and $P^1$—Y, wherein Y is halo.
267. The process of embodiment 266, wherein $P^1$ is p-toluenesulfonyl.
268. The process of embodiment 266 or 267, wherein the base B11 is an alkali metal hydroxide.
269. The process of any one of embodiments 266 to 268, wherein the base B11 is sodium hydroxide.
270. The process of any one of embodiments 266 to 268, wherein the protecting comprise reacting the compound of formula 12a with a base B11 is carried out in a solvent component S20, wherein the solvent component S20 comprises a polar aprotic solvent.
271. The process of embodiment 270, wherein the solvent component S20 comprises acetone.
272. The process of any one of embodiments 145 to 271, wherein the compound of formula 12a is prepared by a process comprising:
reacting a compound of formula 11a:

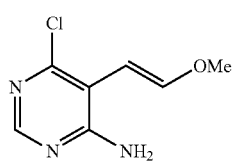

or a salt thereof, with a strong acid A4.
273. The process of embodiment 272, wherein the strong acid A4 is hydrochloric acid.
274. The process of embodiment 272 or 273, wherein the reacting of the compound of formula 11a, or the salt thereof, with a strong acid A4 is carried out in a solvent component S21, wherein the solvent component S21 comprises a polar aprotic solvent.
275. The process of embodiment 274, wherein the solvent component S21 comprises a di-$C_{1-6}$ alkyl ether or a 4-10 membered heterocycloalkyl ether.
276. The process of embodiment 274 or 275, wherein the solvent component S21 comprises tetrahydrofuran.
277. The process of any one of embodiments 272 to 276, wherein the reacting of the compound of formula 11a, or the salt thereof, with a strong acid A4 is carried out at the refluxing temperature of tetrahydrofuran.
278. The process of any one of embodiments 272 to 277, wherein the compound of formula 11a, or the salt thereof, is prepared by a process comprising:
reacting a compound of formula 10a:

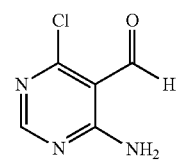

or a salt thereof, with (methoxymethyl)triphenylphosphonium chloride and a base B12.
279. The process of embodiment 278, wherein the base B12 is an alkali metal alkoxide.
280. The process of embodiment 278 or 279, wherein the base B12 is potassium t-butoxide.
281. The process of any one of embodiments 278 to 280, wherein the reacting of the compound of formula 11a, or the salt thereof, with (methoxymethyl)triphenylphosphonium chloride and a base B12 is carried out at a temperature of about 10° C. to about 30° C.
282. The process of any one of embodiments 278 to 281, wherein the reacting of the compound of formula 11a, or the salt thereof, with (methoxymethyl)triphenylphosphonium chloride and a base B12 is carried out in a solvent component S22, wherein the solvent component S22 comprises a polar aprotic solvent.
283. The process of embodiment 282, wherein the solvent component S22 comprises a di-$C_{1-6}$ alkyl ether or a 4-10 membered heterocycloalkyl ether.
284. The process of embodiment 282 or 283, wherein the solvent component S22 comprises tetrahydrofuran.
285. The process of any one of embodiments 278 to 284, wherein the compound of formula 10a, or the salt thereof, is prepared by a process comprising:
reacting a compound of formula 9a:

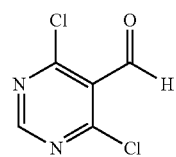

with ammonia.
286. The process of embodiment 285, wherein the reacting of the compound of formula 9a with ammonia is carried out at a temperature of about 40° C. to about 70° C.

287. The process of embodiment 285 or 286, wherein the reacting of the compound of formula 9a with ammonia is carried out in a solvent component S23, wherein the solvent component S23 comprises organic solvent.
288. The process of embodiment 287, wherein the solvent component S23 comprises toluene.
289. The process of any one of embodiments 285 to 288, wherein the compound of formula 9a is prepared by a process comprising:
reacting a compound of formula 8a:

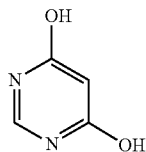

with a Vilsmeier reagent formed from dimethylformamide.
290. The process of embodiment 289, wherein the Vilsmeier reagent is prepared by a process comprising reacting dimethylformamide with a chlorinating agent.
291. The process of embodiment 290, wherein the chlorinating agent is selected from oxalyl chloride, phosphorus oxychloride, triphosgene, thionyl chloride, sulfuryl chloride, and phosphorus pentachloride.
292. The process of embodiment 290, wherein the chlorinating agent is phosphorus oxychloride.
293. The process of any one of embodiments 289 to 292, wherein the compound of formula 12a is prepared by a process comprising:
reacting a compound of formula 15a:

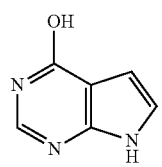

with a chlorinating agent.
294. The process of embodiment 293, wherein the chlorinating agent is selected from oxalyl chloride, phosphorus oxychloride, triphosgene, thionyl chloride, sulfuryl chloride, and phosphorus pentachloride.
295. The process of embodiment 294, wherein the chlorinating agent is phosphorus oxychloride.
296. The process of any one of embodiments 293 to 295, wherein the reacting of the compound of formula 15a with a chlorinating agent is carried out at a temperature of about 50° C. to about 100° C.
297. The process of any one of embodiments 293 to 296, wherein the reacting of the compound of formula 15a with ammonia is carried out in a solvent component S24, wherein the solvent component S24 comprises an organic solvent.
298. The process of embodiment 297, wherein the solvent component S24 comprises toluene.
299. The process of any one of embodiments 293 to 298, wherein the compound of formula 15a is prepared by a process comprising:

(i) reacting a compound of formula 14a:

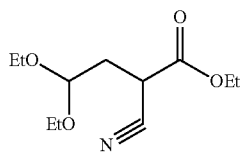

with formamidine acetate and an alkali metal hydroxide to generate a compound of formula 14aa:

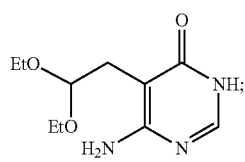

and
(ii) reacting the compound of formula 14aa with a strong acid A4.
300. The process of embodiment 299, wherein the alkali metal hydroxide is sodium ethoxide.
301. The process of embodiment 299 or 300, wherein the reacting of the compound of formula 14a with formamidine acetate and an alkali metal hydroxide is carried out at a temperature of about 50° C. to about 100° C.
302. The process of any one of embodiments 299 to 301, wherein the reacting of the compound of formula 14a with formamidine acetate and an alkali metal hydroxide is carried out in a solvent component S25, wherein the solvent component S25 comprises a polar protic solvent.
303. The process of embodiment 302, wherein the solvent component S25 comprises an alcohol.
304. The process of embodiment 302 or 303, wherein the solvent component S25 comprises formula $C_{1-6}$ alkyl-OH.
305. The process of any one of embodiments 302 to 304, wherein the solvent component S25 comprises ethanol.
306. The process of any one of embodiments 299 to 305, wherein the strong acid A4 is hydrochloric acid.
307. The process of any one of embodiments 299 to 306, wherein the compound of formula 14a is prepared by a process comprising:
reacting a compound of formula 13a:

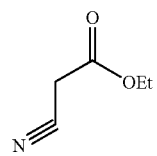

with bromoacetaldehyde diethyl acetal and sodium tert-amyloxide.
308. The process of embodiment 307, wherein the reacting of the compound of formula 13a with bromoacetaldehyde diethyl acetal and sodium tert-amyloxide is carried out at a temperature of about 80° C. to about 100° C.

309. The process of embodiment 307 or 308, wherein the reacting of the compound of formula 13a with bromoacetaldehyde diethyl acetal and sodium tert-amyloxide is carried out in a solvent component S26, wherein the solvent component S26 comprises a polar aprotic solvent.

310. The process of embodiment 309, wherein the solvent component S26 comprises dimethylsulfoxide.

311. The process of any one of embodiments 1 to 310, wherein the compound of formula 3, or the salt thereof, is formed by a process comprising:
reacting a compound of formula A1:

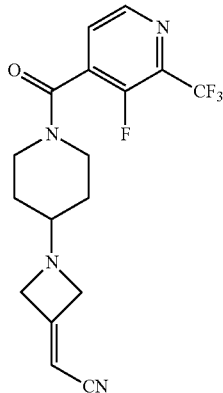

with hydrazine.

312. The process of embodiment 311, wherein the hydrazine is hydrazine hydrate.

313. The process of embodiment 311 or 312, wherein from about 1 to about 3 molar equivalents of hydrazine are utilized relative to the compound of formula A1.

314. The process of embodiment 311 or 312, wherein from about 1.5 to about 2.5 molar equivalents of hydrazine are utilized relative to the compound of formula A1.

315. The process of embodiment 311 or 312, wherein from about 2 to about 2.2 molar equivalents of hydrazine are utilized relative to the compound of formula A1.

316. The process of embodiment 311 or 312, wherein about 2.1 molar equivalents of hydrazine are utilized relative to the compound of formula A1.

317. The process of any one of embodiments 311 to 316, wherein the reacting of the compound of formula A1 is conducted in a solvent component S27.

318. The process of embodiment 317, wherein the solvent component S27 comprises an organic solvent.

319. The process of embodiment 317 or 318, wherein the solvent component S27 comprises an aprotic organic solvent.

320. The process of any one of embodiments 317 to 319, wherein the solvent component S27 comprises acetonitrile.

321. The process of any one of embodiments 311 to 320, wherein the reacting of the compound of formula A1 with hydrazine is conducted at a temperature of from about 20° C. to about 30° C.

322. The process of any one of embodiments 311 to 320, wherein the reacting of the compound of formula A1 with hydrazine is conducted at an ambient temperature.

323. The process of any one of embodiments 311 to 322, wherein the compound of formula 50, or the salt thereof, is prepared by a process comprising:
reacting a compound of formula 54:

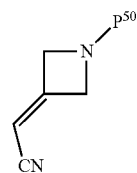

with hydrazine to form the compound of formula 50, or the salt thereof.

324. The process of embodiment 323, wherein the hydrazine is hydrazine hydrate.

325. The process of embodiment 323 or 324, wherein from about 1 to about 3 molar equivalents of hydrazine are utilized relative to the compound of formula 54.

326. The process of embodiment 323 or 324, wherein from about 1.5 to about 2.5 molar equivalents of hydrazine are utilized relative to the compound of formula 54.

327. The process of embodiment 323 or 324, wherein from about 2 to about 2.2 molar equivalents of hydrazine are utilized relative to the compound of formula 54.

328. The process of embodiment 323 or 324, wherein about 2.1 molar equivalents of hydrazine are utilized relative to the compound of formula 54.

329. The process of any one of embodiments 323 to 328, wherein the reacting of the compound of formula 54 is conducted in a solvent component S54.

330. The process of embodiment 329, wherein the solvent component S54 comprises an organic solvent.

331. The process of embodiment 329 or 330, wherein the solvent component S54 comprises an aprotic organic solvent.

332. The process of any one of embodiments 329 to 331, wherein the solvent component S54 comprises acetonitrile.

333. The process of any one of embodiments 323 to 332, wherein the reacting of the compound of formula 54 with hydrazine is conducted at a temperature of from about 20° C. to about 30° C.

334. The process of any one of embodiments 323 to 332, wherein the reacting of the compound of formula 54 with hydrazine is conducted at an ambient temperature.

335. A compound of formula 50, having the formula:

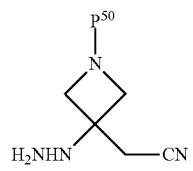

or a salt thereof, wherein $P^{50}$ is an amino protecting group.

336. The compound of embodiment 335, having the formula:

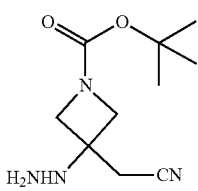

or a salt thereof.

337. A compound of formula 3, having the formula:

3

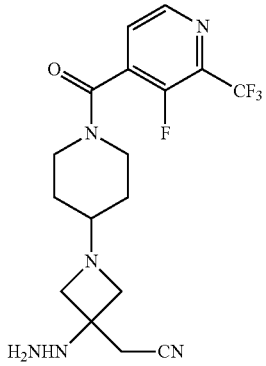

or a salt thereof.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES 2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile and its adipic acid salt were prepared according to the schemes below.

Scheme 1a.

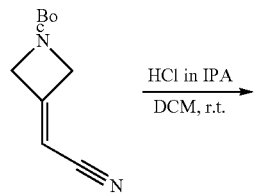

-continued

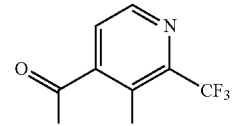
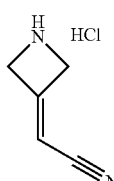
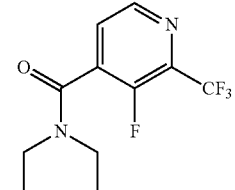
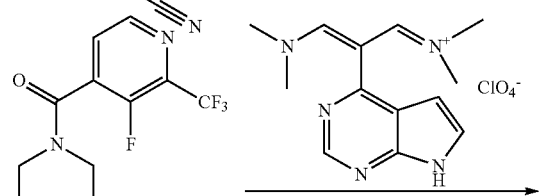
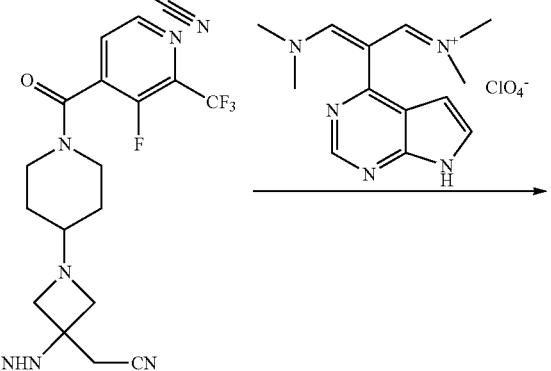
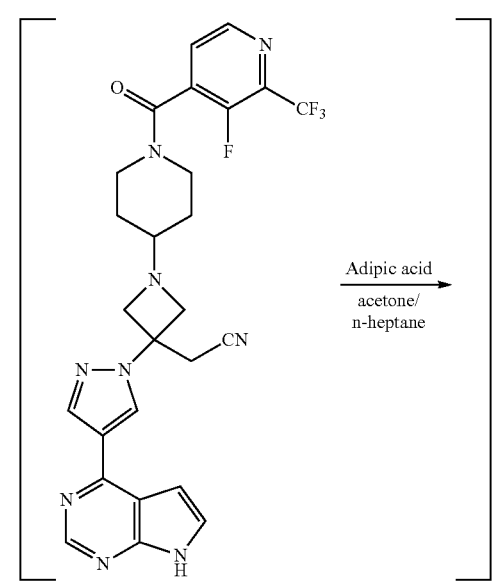
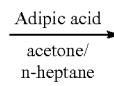

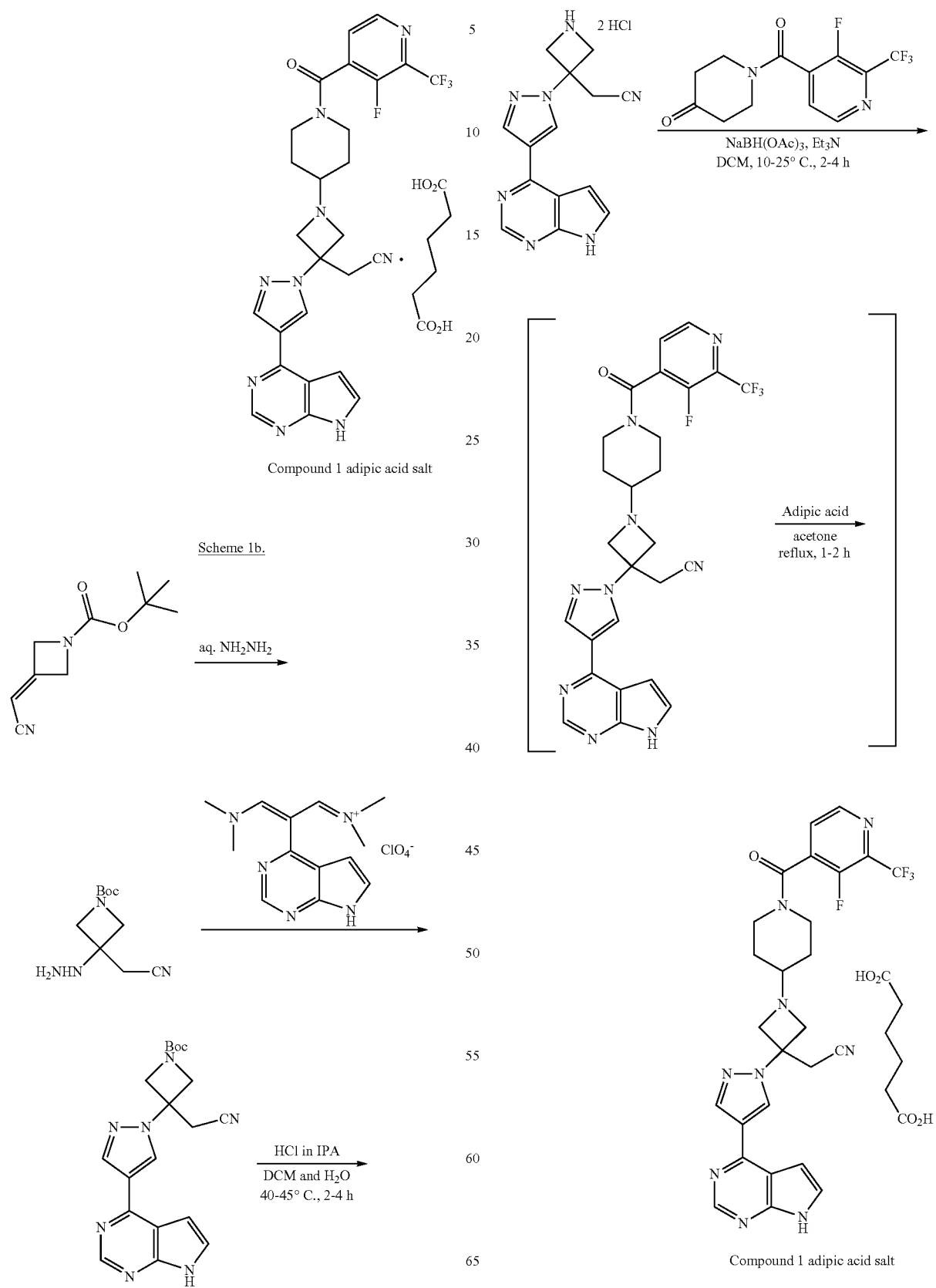

Example 1. Preparation of (E)-N-(3-(Dimethyl-amino)-2-(7H-pyrrolo[2,3-d]pyrimidin-4-yl)ally-lidene)-N-methylmethanaminium Chloride Hydrochloride (Compound 2 Chloride Hydrochloride)

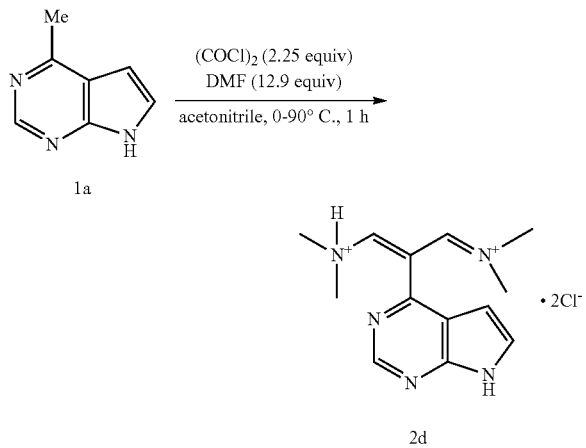

A solution of oxalyl chloride (21.88 g, 15.1 mL, 169 mmol, 2.25 equiv) in anhydrous acetonitrile (65 mL) was cooled to 0-5° C. in an ice bath. Anhydrous DMF (70.8 g, 75.0 mL, 969 mmol, 12.9 equiv) was added dropwise into the solution to form the corresponding Vilsmeier reagent. During addition of DMF, the internal temperature was controlled to below 10° C. The ice batch was removed and the reaction mixture was gradually warmed to ambient temperature over 40 minutes. Methyl-7H-pyrrolo[2,3-d]pyrimidine (1a, 10.0 g, 75.1 mmol) was charged into the in-situ generated Vilsmeier reagent as a solid in one portion at ambient temperature and the resulting slurry was agitated at ambient temperature for 5-10 minutes to ensure complete mixing before being warmed to 85-90° C. The reaction mixture was agitated at 85-90° C. for one hour before being gradually cooled to ambient temperature. Anhydrous tetrahydrofuran (THF, 100 mL) was charged and the resulting slurry was agitated at ambient temperature for two hours followed by at 0-5° C. for two hours. The solids were collected by filtration, washed with a one to one mixture of THF and MTBE (2×100 mL), and dried under vacuum to constant weight to afford the desired product, (E)-N-(3-(Dimethylamino)-2-(7H-pyrrolo[2,3-d]pyrimidin-4-yl)ally-lidene)-N-methylmethanaminium chloride hydrochloride (2d, 24.38 g, 23.72 g theoretical, 98.9% by HPLC area %, 90.2 wt % by NMR, 92.6% yield), as a yellow to brown crystalline solid (Form I), which contained 6-7% of DMF and acetonitrile and 1-2% of water and was used in the subsequent reaction without further purification. For Compound 2d: $^1$H NMR (500 MHz, DMSO-$d_6$) δ 13.65 (s, 1H), 8.99 (s, 1H), 8.48 (s, 2H), 7.99-7.94 (m, 1H), 6.84 (dd, J=3.6, 1.6 Hz, 1H), 3.48 (s, 6H), 2.82 (s, 6H) ppm; $^{13}$C NMR (DMSO-$d_6$, 125 MHz) δ 163.8, 151.3, 147.6, 145.0, 132.1, 117.5, 102.9, 91.6, 48.9, 42.1 ppm; $C_{13}H_{19}Cl_2N_5$ (MW, 279.77 for Compound 2c and 244.32 for Compound 2 without anion) LCMS (EI) m/e 244.2 (M$^+$, base peak).

Crystalline Form I of Compound 2d was characterized by XRPD, DSC and TGA.

X-Ray Powder Diffraction (XRPD): The X-Ray Powder Diffraction (XRPD) was obtained from Bruker D8 Advance ECO X-ray Powder Diffractometer (XRPD) instrument. The general experimental procedures for XRPD were: (1) X-ray radiation from copper at 1.5418 Å and LYNXEYE™ detector; (2) X-ray power at 40 kV, 25 mA; and (3) the sample powder was dispersed on a zero-background sample holder. The general measurement conditions for XRPD were: Start Angle 3 degrees; Stop Angle 30 degrees; Sampling 0.015 degrees; and Scan speed 2 degree/min.

Form I of Compound 2d was confirmed to be crystalline solid according to XRPD analysis. The XRPD pattern of Compound 2d crystalline Form I is shown in FIG. 1 and the peak data is given in Table 1.

TABLE 1

| XRPD Peak Data for Compound 2d Form I | |
|---|---|
| 2-Theta (°) | Relative Intensity (%) |
| 7.4 | 14.9 |
| 9.2 | 1.9 |
| 11.0 | 3.4 |
| 11.5 | 0.8 |
| 12.5 | 40.1 |
| 13.1 | 11.4 |
| 14.1 | 28.9 |
| 14.6 | 34.0 |
| 15.0 | 10.2 |
| 15.5 | 1.0 |
| 15.9 | 17.3 |
| 17.3 | 2.8 |
| 17.7 | 18.4 |
| 18.5 | 57.3 |
| 19.0 | 10.2 |
| 19.5 | 0.6 |
| 20.5 | 19.1 |
| 20.8 | 42.2 |
| 21.1 | 3.2 |
| 21.3 | 1.8 |
| 22.2 | 53.8 |
| 23.0 | 15.9 |
| 23.1 | 3.6 |
| 24.1 | 11.5 |
| 24.3 | 26.7 |
| 24.9 | 3.2 |
| 25.3 | 18.9 |
| 25.5 | 16.9 |
| 26.0 | 22.4 |
| 26.3 | 100 |
| 27.2 | 1.9 |
| 27.9 | 81.5 |
| 28.2 | 6.3 |
| 28.8 | 11.7 |
| 29.2 | 19.8 |
| 29.5 | 3.9 |

Figure 2:
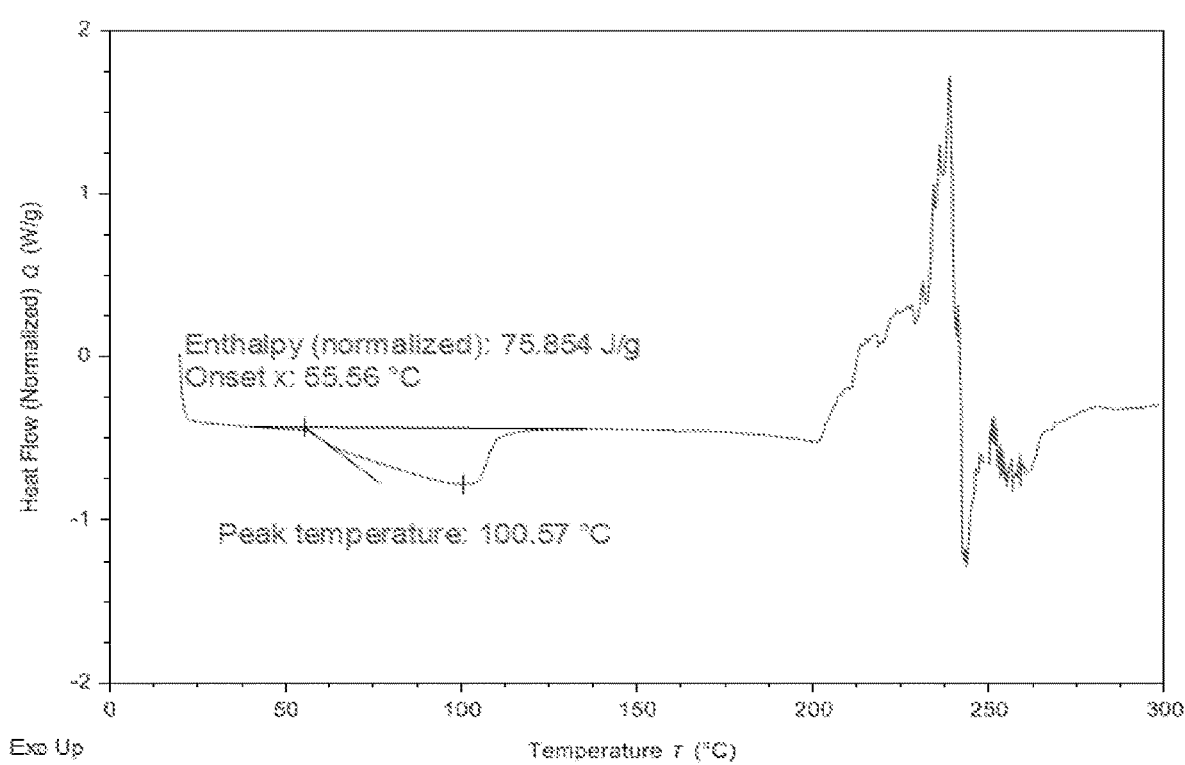
FIG. 2 is a differential scanning calorimetry (DSC) thermogram of Compound 2d Form I.

Differential Scanning calorimetry (DSC): The DSC was obtained from TA Instruments Differential Scanning calorimetry, Discovery DSC2500 with autosampler. The DSC instrument conditions were as follows: 20-300° C. at 10° C./min; Tzero aluminum sample pan and lid; and nitrogen gas flow at 50 mL/min. DSC analysis of Compound 2d crystalline Form I revealed one endothermic peak with an onset temperature of 55.6° C. and a maximum at 100.6° C. The DSC thermogram of Compound 2d crystalline Form I is provided in FIG. 2.

Figure 3:
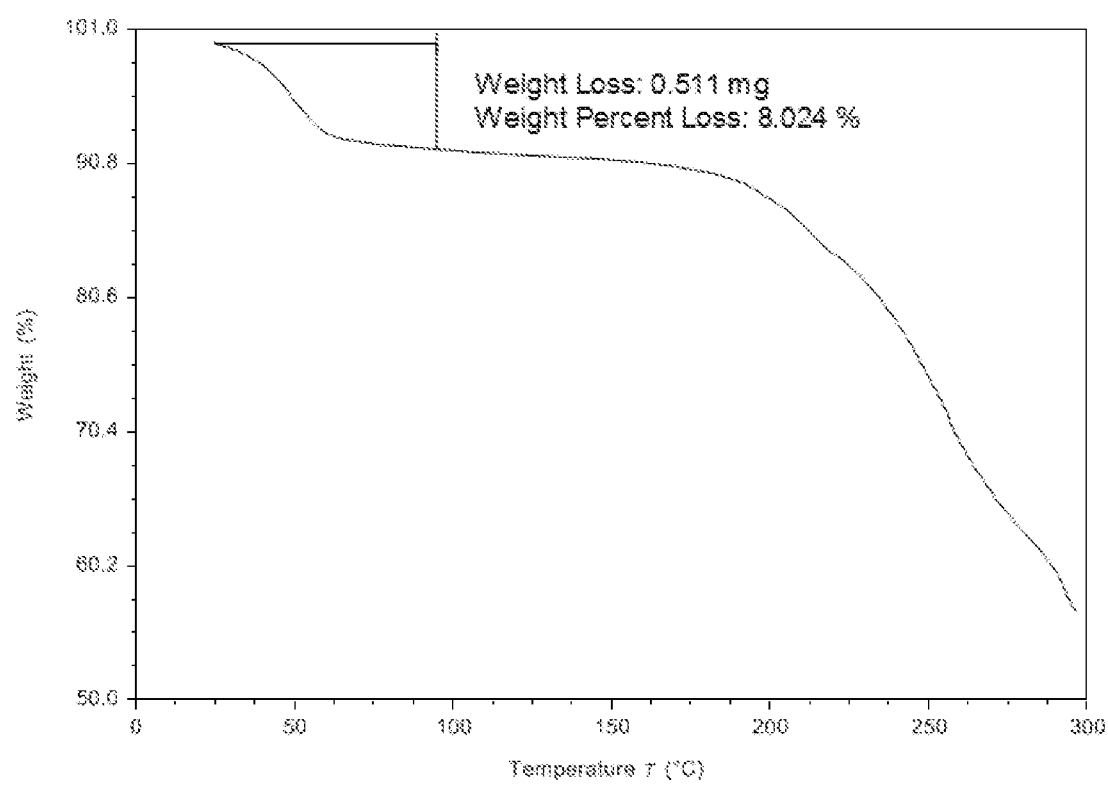
FIG. 3 is a thermogravimetric analysis (TGA) thermogram of Compound 2d Form I.

Thermogravimetric Analysis (TGA): The TGA was obtained from TA Instruments Thermogravimetric Analyzer, Discovery TGA5500 with autosampler. The general experimental conditions for TGA were: ramp from 25° C. to 300° C. at 10° C./min; nitrogen purge gas flow at 25 mL/min; platinum sample holder. TGA analysis of Compound 2d crystalline Form I revealed 8.0% weight loss below 100° C. and significant weight loss above 175° C. due to decomposition. The TGA thermogram of Compound 2d crystalline Form I is provided in FIG. 3.

Example 2: Alternative Preparation of (E)-N-(3-(Dimethylamino)-2-(7H-pyrrolo[2,3-d]pyrimidin-4-yl)allylidene)-N-methylmethanaminium Chloride Hydrochloride (Compound 2d)

A solution of oxalyl chloride (43.76 g, 30.2 mL, 338 mmol, 2.25 equiv) in anhydrous acetonitrile (130 mL) was cooled to 0-5° C. in an ice bath. Anhydrous DMF (141.6 g, 140.0 mL, 1938 mmol, 12.9 equiv) was added dropwise into the solution to form the corresponding Vilsmeier reagent. During addition of DMF, the internal temperature was controlled to below 10° C. The ice bath was removed and the reaction mixture was gradually warmed to ambient temperature over 40 minutes. Methyl-7H-pyrrolo[2,3-d]pyrimidine hydrochloride (Compound 1a hydrochloride 25.44 g, 150 mmol) was charged into the in-situ generated Vilsmeier reagent as a solid in one portion at ambient temperature and the resulting slurry was agitated at ambient temperature for 5-10 minutes to ensure complete mixing before being warmed to 85-90° C. The reaction mixture was agitated at 85-90° C. for one hour before being gradually cooled to ambient temperature. Anhydrous tetrahydrofuran (THF, 200 mL) was charged and the resulting slurry was agitated at ambient temperature for 48 hours followed by at 0-5° C. for 2 hours. The solids were collected by filtration, washed with a one to one mixture of THF and MTBE (2×200 mL), and dried under vacuum to constant weight to afford the desired product, (E)-N-(3-(Dimethylamino)-2-(7H-pyrrolo[2,3-d]pyrimidin-4-yl)allylidene)-N-methylmethanaminium chloride hydrochloride (Compound 2d), 46.17 g, 47.43 g theoretical, 99.5% by HPLC area %, 95.2 wt % by NMR, 92.7% yield), as a yellow to brown crystalline solid (Form II), which contained 2.3% of DMF and acetonitrile and 0.8% of water and was used in the subsequent reaction without further purification. For Compound 2d: $^1$H NMR (500 MHz, DMSO-$d_6$) δ 13.65 (s, 1H), 8.99 (s, 1H), 8.48 (s, 2H), 7.99-7.94 (m, 1H), 6.84 (dd, J=3.6, 1.6 Hz, 1H), 3.48 (s, 6H), 2.82 (s, 6H) ppm; $^{13}$C NMR (DMSO-$d_6$, 125 MHz) δ 163.8, 151.3, 147.6, 145.0, 132.1, 117.5, 102.9, 91.6, 48.9, 42.1 ppm; $C_{13}H_{19}Cl_2N_5$ (MW, 279.77 for Compound 2c and 244.32 for Compound 2 without anion) LCMS (EI) m/e 244.2 (M$^+$, base peak).

Crystalline Form II of Compound 2d was characterized by XRPD, DSC and TGA.

X-Ray Powder Diffraction (XRPD): The X-Ray Powder Diffraction (XRPD) was obtained from Bruker D8 Advance ECO X-ray Powder Diffractometer (XRPD) instrument. The general experimental procedures for XRPD were: (1) X-ray radiation from copper at 1.5418 Å and LYNXEYE™ detector; (2) X-ray power at 40 kV, 25 mA; and (3) the sample powder was dispersed on a zero-background sample holder. The general measurement conditions for XRPD were: Start Angle 3 degrees; Stop Angle 30 degrees; Sampling 0.015 degrees; and Scan speed 2 degree/min.

Figure 4:
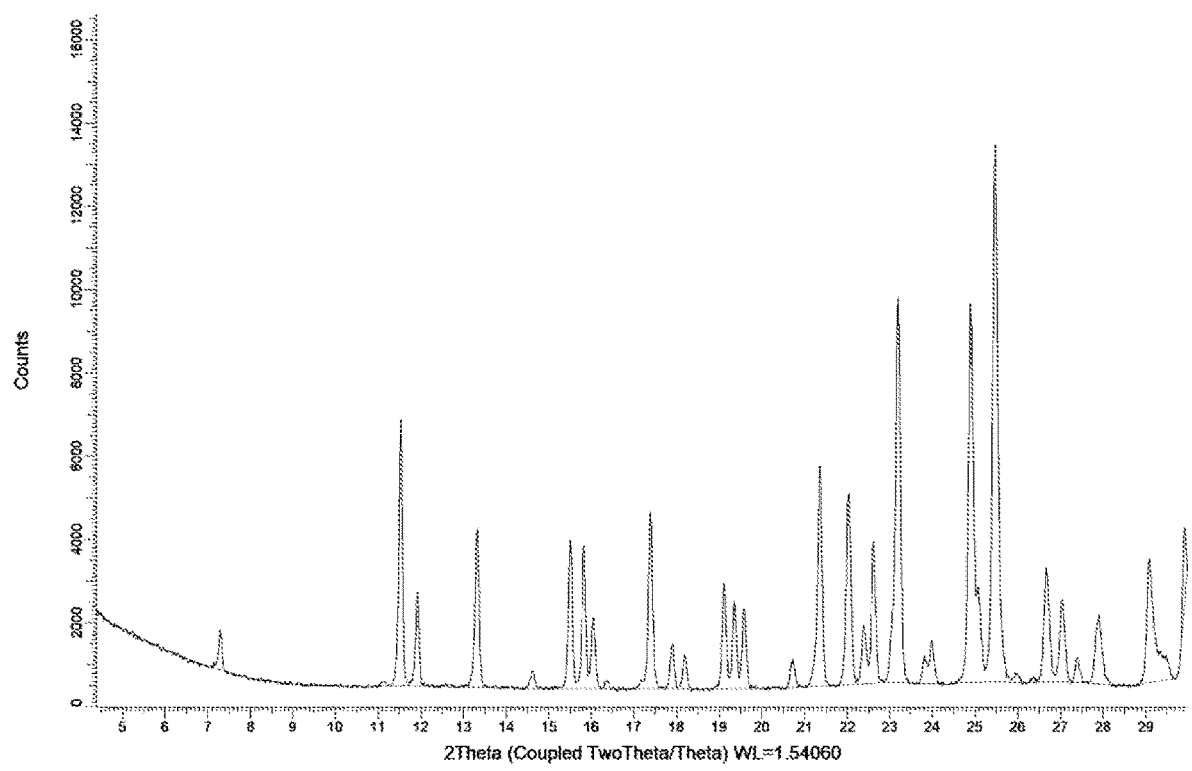
FIG. 4 is an XRPD pattern of Compound 2d Form II.

Crystalline Form II of Compound 2d was confirmed to be crystalline solid according to XRPD analysis. The XRPD pattern of Compound 2d crystalline Form II is shown in FIG. 4 and the peak data is given in Table 2.

TABLE 2

| XRPD Peak Data for Compound 2d Form II | |
|---|---|
| 2-Theta (°) | Relative Intensity (%) |
| 7.3 | 7.3 |
| 11.1 | 0.9 |
| 11.5 | 49.6 |
| 11.9 | 17.0 |
| 13.3 | 29.2 |
| 14.6 | 3.3 |
| 15.5 | 27.3 |
| 15.8 | 26.5 |
| 16.1 | 13.1 |
| 16.4 | 1.5 |
| 17.4 | 32.8 |
| 17.9 | 8.1 |
| 18.2 | 6.4 |
| 19.1 | 19.5 |
| 19.4 | 16.2 |
| 19.6 | 14.9 |
| 20.7 | 5.3 |
| 21.4 | 40.8 |
| 22.0 | 35.6 |
| 22.4 | 10.8 |
| 22.6 | 26.2 |
| 23.2 | 71.6 |
| 23.8 | 4.9 |
| 24.0 | 8.0 |
| 24.9 | 70.7 |
| 25.5 | 100 |
| 26.0 | 1.7 |
| 26.4 | 0.9 |
| 26.7 | 21.1 |
| 27.0 | 15.3 |
| 27.4 | 4.6 |
| 27.9 | 12.6 |
| 29.1 | 23.1 |
| 29.5 | 4.2 |

Figure 5:
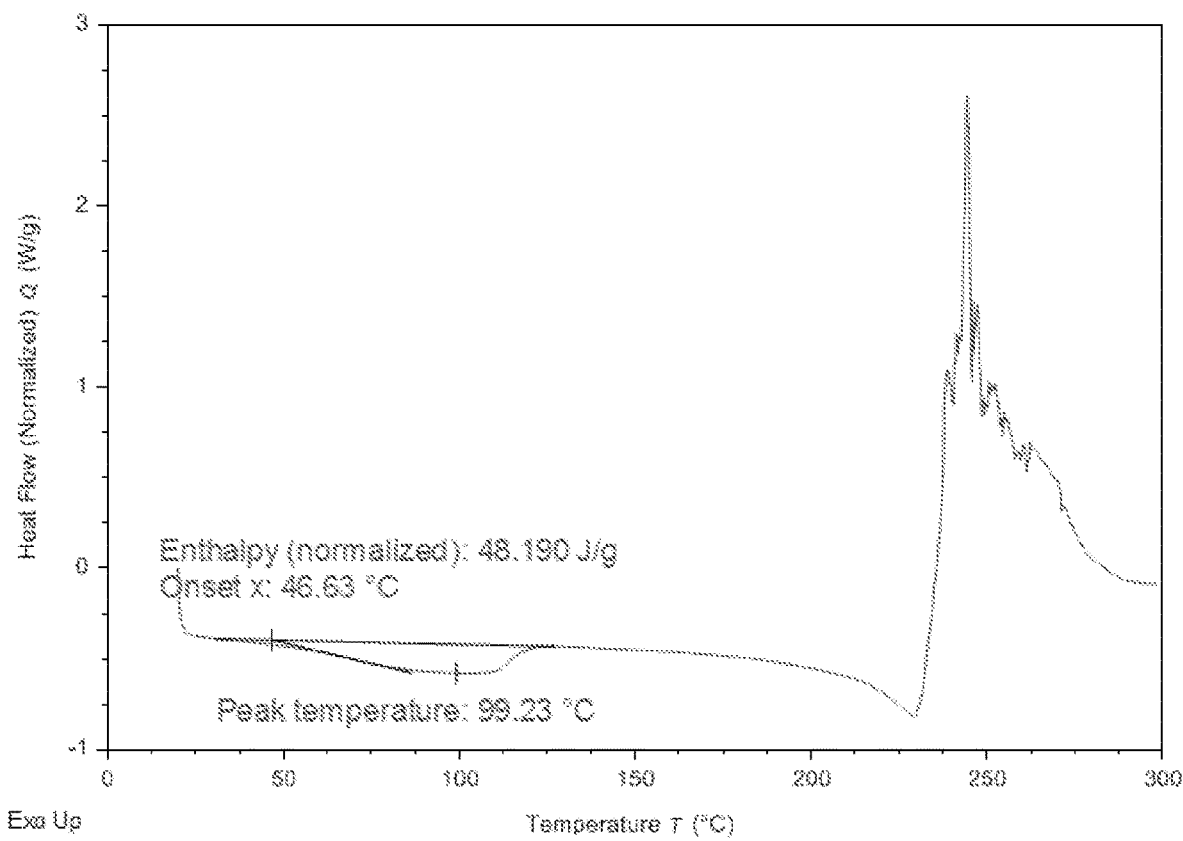
FIG. 5 is a DSC thermogram of Compound 2d Form II.

Differential Scanning calorimetry (DSC): The DSC was obtained from TA Instruments Differential Scanning calorimetry, Discovery DSC2500 with autosampler. The DSC instrument conditions were as follows: 20-300° C. at 10° C./min; Tzero aluminum sample pan and lid; and nitrogen gas flow at 50 mL/min. DSC analysis of Compound 2d crystalline Form II revealed one endothermic peak with an onset temperature of 46.6° C. and a maximum at 99.2° C. The DSC thermogram of Compound 2d crystalline Form II is provided in FIG. 5.

Figure 6:
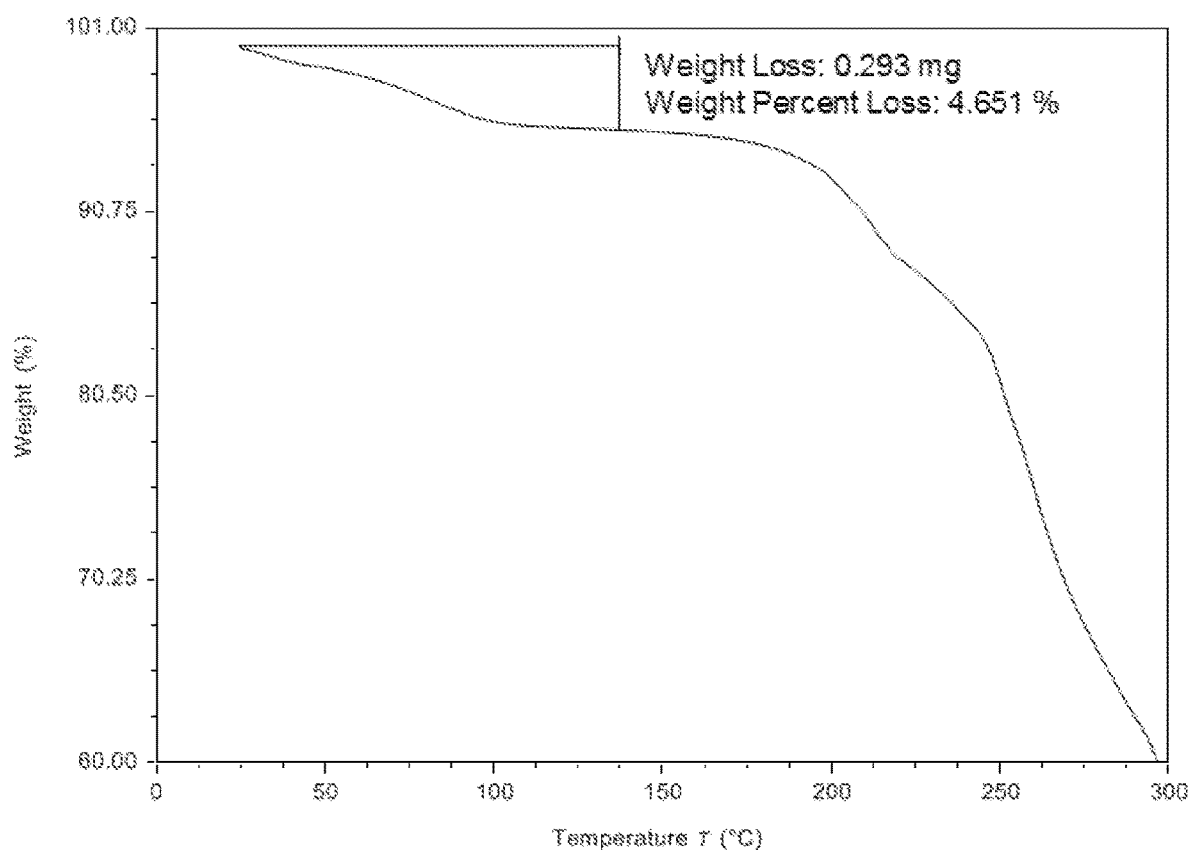
FIG. 6 is a TGA thermogram of Compound 2d Form II.

Thermogravimetric Analysis (TGA): The TGA was obtained from TA Instruments Thermogravimetric Analyzer, Discovery TGA5500 with autosampler. The general experimental conditions for TGA were: ramp from 25° C. to 300° C. at 10° C./min; nitrogen purge gas flow at 25 mL/min; platinum sample holder. TGA analysis of Compound 2d crystalline Form II revealed 4.7% weight loss below 150° C. and significant weight loss above 175° C. due to decomposition. The TGA thermogram of Compound 2d crystalline Form II is provided in FIG. 6.

Example 3: Alternative Preparation of (E)-N-(3-(Dimethylamino)-2-(7H-pyrrolo[2,3-d]pyrimidin-4-yl)allylidene)-N-methylmethanaminium Chloride Hydrochloride (2d)

Example 4: Preparation of (E)-N-(3-(Dimethylamino)-2-(7H-pyrrolo[2,3-d]pyrimidin-4-yl)allylidene)-N-methylmethanaminium Chloride (Compound 2 Chloride) Using POCl₃

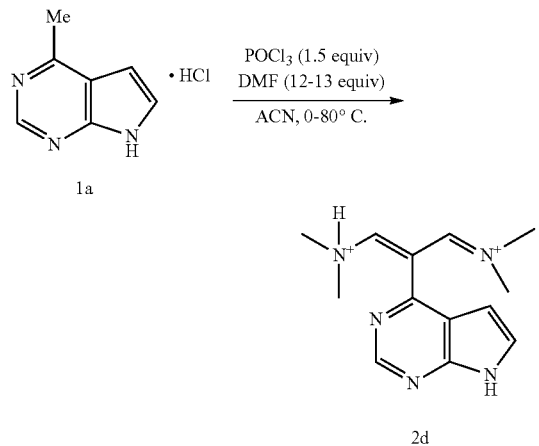

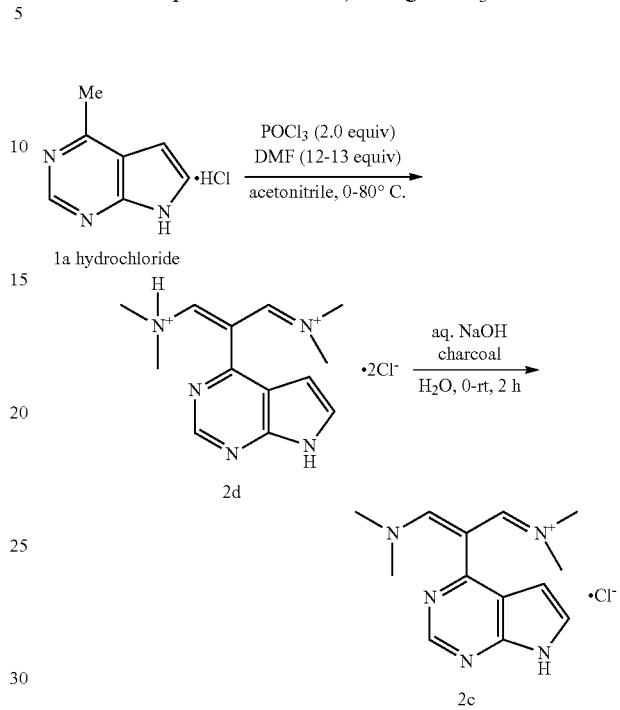

A solution of phosphorus oxochloride (POCl₃, 17.25 g, 10.5 mL, 112.5 mmol, 1.5 equiv) in anhydrous acetonitrile (65 mL) was cooled to 0-5° C. in an ice bath. Anhydrous DMF (70.8 g, 70.0 mL, 968 mmol, 12.9 equiv) was added dropwise into the solution to form the corresponding Vilsmeier reagent. During addition of DMF, the internal temperature was controlled to below 10° C. The ice batch was removed and the reaction mixture was gradually warmed to ambient temperature. Methyl-7H-pyrrolo[2,3-d]pyrimidine hydrochloride (Compound 1a hydrochloride, 12.72 g, 75.0 mmol) was charged into the in-situ generated Vilsmeier reagent as a solid in one portion at ambient temperature and the resulting slurry was agitated at ambient temperature for 5-10 minutes to ensure complete mixing before being warmed to 75-80° C. The reaction mixture was agitated at 75-80° C. for one hour before being gradually cooled to ambient temperature. Anhydrous tetrahydrofuran (THF, 100 mL) was charged and the resulting slurry was agitated at ambient temperature for two hours followed by at 0-5° C. for two hours. The solids were collected by filtration and washed with a one to one mixture of THF and MTBE (2×100 mL) to afford the desired product, (E)-N-(3-(Dimethylamino)-2-(7H-pyrrolo[2,3-d]pyrimidin-4-yl)allylidene)-N-methylmethanaminium chloride hydrochloride (Compound 2d, 27.83 g, 23.72 g theoretical, 96.1% by HPLC area %, 69.0 wt % by NMR, 81.0% yield), as a yellow to brown crystalline (Form I) solid, which contained 11.49% of DMF and acetonitrile and 1.38% of water and was used in the subsequent reaction without further purification. For Compound 2d: $^1$H NMR (500 MHz, DMSO-$d_6$) δ 13.65 (s, 1H), 8.99 (s, 1H), 8.48 (s, 2H), 7.99-7.94 (m, 1H), 6.84 (dd, J=3.6, 1.6 Hz, 1H), 3.48 (s, 6H), 2.82 (s, 6H) ppm; $^{13}$C NMR (DMSO-$d_6$, 125 MHz) δ 163.8, 151.3, 147.6, 145.0, 132.1, 117.5, 102.9, 91.6, 48.9, 42.1 ppm; $C_{13}H_{19}Cl_2N_5$ (MW, 279.77 for Compound 2c and 244.32 for Compound 2 without anion) LCMS (EI) m/e 244.2 (M⁺, base peak).

A solution of phosphorus oxochloride (POCl₃, 23.0 g, 14.0 mL, 150 mmol, 2.0 equiv) in anhydrous acetonitrile (65 mL) was cooled to 0-5° C. in an ice bath. Anhydrous DMF (70.8 g, 70.0 mL, 968 mmol, 12.9 equiv) was added dropwise into the solution to form the corresponding Vilsmeier reagent. During addition of DMF, the internal temperature was controlled to below 10° C. The ice batch was removed and the reaction mixture was gradually warmed to ambient temperature. Methyl-7H-pyrrolo[2,3-d]pyrimidine hydrochloride (Compound 1a hydrochloride, 12.72 g, 75.0 mmol) was charged into the in-situ generated Vilsmeier reagent as a solid in one portion at ambient temperature and the resulting slurry was agitated at ambient temperature for 5-10 minutes to ensure complete mixing before being warmed to 75-80° C. The reaction mixture was agitated at 75-80° C. for one hour before being gradually cooled to ambient temperature. Anhydrous tetrahydrofuran (100 mL) was charged and the resulting slurry was agitated at ambient temperature for two hours followed by at 0-5° C. for two hours. The solids were collected by filtration and washed with a one to one mixture of THF and MTBE (2×100 mL) to afford the desired product, (E)-N-(3-(Dimethylamino)-2-(7H-pyrrolo[2,3-d]pyrimidin-4-yl)allylidene)-N-methylmethanaminium chloride hydrochloride (Compound 2d), as a yellow to brown wet cake. The wet cake was then dissolved in water (120 mL), and the pH of the resulting aqueous solution was adjusted to 7-8 by treating with a 50% aqueous solution of sodium hydroxide (NaOH, 19.06 g) at 0-5° C. The neutralized aqueous solution was then treated with charcoal (5.5 g) and agitated at ambient temperature for 12 hours. The charcoal was removed by filtration through a Celite bed and the Celite bed was washed with water (50 mL). The resulting aqueous solution, which contained the desired product, (E)-N-(3-(Dimethylamino)-2-(7H-pyrrolo[2,3-d]pyrimidin- 4-yl)allylidene)-N-methylmethanaminium chloride (Compound 2c, >99.0% pure by HPLC area %), was used for the subsequent reactions without further treatment.

Example 5: Synthesis of (E)-N-(3-(Dimethylamino)-2-(7H-pyrrolo[2,3-d]pyrimidin-4-yl)allylidene)-N-methylmethanaminium Chloride (Compound 2c) Using Triphosgene

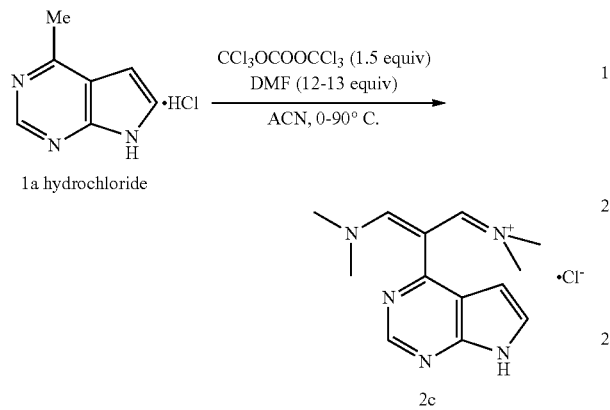

A solution of triphosgene ($(CCl_3O)_2CO$, 37.4 g, 126 mmol, 1.5 equiv) in anhydrous acetonitrile (73 mL) was cooled to 0-5° C. in an ice bath. Anhydrous DMF (79.0 g, 84 mL, 1083 mmol, 12.9 equiv) was added dropwise into the solution to form the corresponding Vilsmeier reagent. During addition of DMF, the internal temperature was controlled to below 10° C. The ice batch was removed and the reaction mixture was gradually warmed to ambient temperature over 40 minutes. Methyl-7H-pyrrolo[2,3-d]pyrimidine hydrochloride (Compound 1a hydrochloride, 14.25 g, 84.0 mmol) was charged into the in-situ generated Vilsmeier reagent as a solid in one portion at ambient temperature and the resulting slurry was agitated at ambient temperature for 5-10 minutes to ensure complete mixing before being warmed to 80-90° C. The reaction mixture was agitated at 80-90° C. for one hour before being gradually cooled to ambient temperature. Anhydrous tetrahydrofuran (THF, 112 mL) was charged and the resulting slurry was agitated at ambient temperature for 12 hours followed by at 0-5° C. for 2 hours. The solids were collected by filtration, washed with a one to one mixture of THF and MTBE (2×200 mL), and dried under vacuum to constant weight to afford the desired product, (E)-N-(3-(Dimethylamino)-2-(7H-pyrrolo[2,3-d]pyrimidin-4-yl)allylidene)-N-methylmethanaminium chloride (Compound 2c), 28.3 g, 23.5 g theoretical, 98.8% by HPLC area %, 64.9 wt % by HPLC, 78.2% yield), as a yellow to brown amorphous solid, which contained 19.7% of DMF and 0.8% of water and was used in the subsequent reaction without further purification. For Compound 2c: $^1$H NMR (500 MHz, DMSO-$d_6$) δ 13.65 (s, 1H), 8.99 (s, 1H), 8.48 (s, 2H), 7.99-7.94 (m, 1H), 6.84 (dd, J=3.6, 1.6 Hz, 1H), 3.48 (s, 6H), 2.82 (s, 6H) ppm; $^{13}$C NMR (DMSO-$d_6$, 125 MHz) δ 163.8, 151.3, 147.6, 145.0, 132.1, 117.5, 102.9, 91.6, 48.9, 42.1 ppm; $C_{13}H_{19}Cl_2N_5$ (MW, 279.77 for Compound 2c and 244.32 for Compound 2 without anion) LCMS (EI) m/e 244.2 (M$^+$, base peak).

Example 6: Preparation of (E)-N-(3-(dimethylamino)-2-(7H-pyrrolo[2,3-d]pyrimidin-4-yl)allylidene)-N-methylmethanaminium Salts

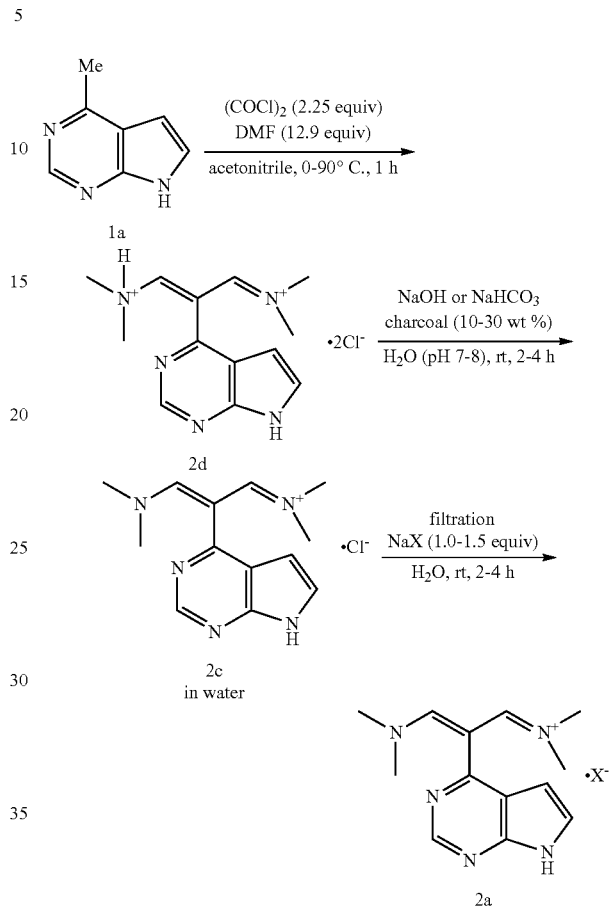

2a
2 perchlorate: X = $ClO_4^-$
2 tetrafluoroborate: X = $BF_4^-$
2 hexafluorophosphate: X = $PF_6^-$
2 hexafluoroarsenate: X = $AsF_6^-$
2-hexafluoroantimonate: X = $SbF_6^-$ (E)-N-(3-(dimethylamino)-2-(7H-pyrrolo[2,3-d]pyrimidin-4-yl)allylidene)-N-methylmethanaminium Perchlorate (Compound 2 Perchlorate)

To a solution of (E)-N-(3-(dimethylamino)-2-(7H-pyrrolo[2,3-d]pyrimidin-4-yl)allylidene)-N-methylmethanaminium chloride (Compound 2c2.94 g, 10.525 mmol) in water (8.06 mL) was added sodium perchlorate (NaClO$_4$, 1.933 g, 15.79 mmol, 1.50 equiv) at ambient temperature. After stirred at 20-25° C. for 12 hour, the slurry was cooled in an ice bath for 2 hours. The solids was filtered, washed with cold H$_2$O (3×2 mL) and dried under vacuum to afford the crude desired product, (E)-N-(3-(dimethylamino)-2-(7H-pyrrolo[2,3-d]pyrimidin-4-yl)allylidene)-N-methylmethanaminium perchlorate (Compound 2 perchlorate), as white solids, which were used in the subsequent reaction without further purification. $^1$H NMR (400 MHz, DMSO-$d_6$) δ 12.50-12.17 (s, 1H), 8.94-8.73 (s, 1H), 8.08-7.87 (s, 2H), 7.77-7.57 (dd, J=3.4, 2.3 Hz, 1H), 6.56-6.31 (dd, J=3.5, 1.7 Hz, 1H), 3.54-3.04 (s, 6H), 2.45-2.17 (s, 6H) ppm; $C_{13}H_{18}ClN_5O_4$ (MW, 343.77 for Compound 2 perchlorate and 244.32 for Compound 2 without anion) LCMS (EI) m/e 244.2 (M+, base peak).

(E)-N-(3-(dimethylamino)-2-(7H-pyrrolo[2,3-d]pyrimidin-4-yl)allylidene)-N-methylmethanaminium tetrafluoroborate (Compound 2 tetrafluoroborate) To a solution of (E)-N-(3-(dimethylamino)-2-(7H-pyrrolo[2,3-d]pyrimidin-4-yl)allylidene)-N-methylmethanaminium chloride (Compound 2c, 2.94 g, 10.525 mmol) in water (8.06 mL) was added sodium tetrafluoroborate (NaBF$_4$, 1.733 g, 15.79 mmol, 1.50 equiv) at ambient temperature. After stirring at 20-25° C. for 12 hours, the slurry was cooled in an ice bath for 2 hours. The solids was filtered, washed with cold H$_2$O (3×2 mL) and dried under vacuum to afford the crude desired product, (E)-N-(3-(dimethylamino)-2-(7H-pyrrolo[2,3-d]pyrimidin-4-yl)allylidene)-N-methylmethanaminium tetrafluoroborate (Compound 2 tetrafluoroborate, 1.80 g, 3.49 g theoretical, 51.6% yield), as a white solid, which was used in the subsequent reaction without further purification. $^1$H NMR (400 MHz, DMSO-d$_6$) δ 12.39-12.34 (s, 1H), 8.85-8.80 (s, 1H), 7.99-7.94 (s, 2H), 7.71-7.65 (dd, J=3.4, 2.2 Hz, 1H), 6.52-6.46 (dd, J=3.5, 1.7 Hz, 1H), 3.34-3.29 (s, 6H), 2.38-2.33 (s, 6H) ppm; $^{11}$B NMR (DMSO-d$_6$, 128 MHz) δ −1.27 ppm; $^{19}$F NMR (DMSO-d$_6$, 376.5 MHz) δ −148.23 and −148.28 ppm; C$_{13}$H$_{18}$BF$_4$N$_5$ (MW, 331.13 for Compound 2 tetrafluoroborate and 244.32 for Compound 2 without anion) LCMS (EI) m/e 244.2 (M+, base peak).

(E)-N-(3-(dimethylamino)-2-(7H-pyrrolo[2,3-d]pyrimidin-4-yl)allylidene)-N-methylmethanaminium Hexafluorophosphate (Compound 2 Hexafluorophosphate)

To a solution of crude (E)-N-(3-(dimethylamino)-2-(7H-pyrrolo[2,3-d]pyrimidin-4-yl)allylidene)-N-methylmethanaminium chloride hydrochloride (Compound 2d, 25.61 g, 91.6 mmol) in water (80 mL), generated from 4-methyl-7H-pyrrolo[2,3-d]pyrimidine (12.19 g, 91.6 mmol) via the corresponding Vilsmeier reaction as described in Example 1, was added an aqueous solution of sodium hydroxide (NaOH) at 0-5° C. to adjust the solution pH to 7-8. The resulting aqueous solution was added charcoal (7.69 g) and the mixture was agitated at ambient temperature for 2-4 hours. Charcoal was removed by filtration through a Celite bed and the wet charcoal cake was washed with water (15 mL). The combined aqueous solution was then added sodium hexafluorophosphate (NaPF$_6$, 20.08 g, 120 mmol, 1.31 equiv) at ambient temperature. After stirring at 20-25° C. for 1 hour, the slurry was cooled in an ice bath for 30 minutes. The solids was filtered, washed with cold H$_2$O (2×25 mL) and dried under vacuum to afford the crude desired product, (E)-N-(3-(dimethylamino)-2-(7H-pyrrolo[2,3-d]pyrimidin-4-yl)allylidene)-N-methylmethanaminium hexafluorophosphate (Compound 2 hexafluorophosphate, 24.30 g, 35.81 g theoretical, 67.9% yield, 98.7% by HPLC area %), as white crystalline solids, which were used in the subsequent reaction without further purification. The crude Compound 2 hexafluorophosphate can be purified by recrystallization from water to generate pure product as white crystalline solids. For Compound 2 hexafluorophosphate: $^1$H NMR (500 MHz, DMSO-d$_6$) δ 12.36 (s, 1H), 8.83 (s, 1H), 7.97 (br s, 2H), 7.68 (dd, J=3.2, 2.6 Hz, 1H), 6.48 (dd, J=3.4, 1.8 Hz, 1H), 3.32 (s, 6H), 2.36 (br s, 6H) ppm; $^{13}$C NMR (125 MHz, DMSO-d$_6$) δ 163.7, 152.9, 151.4, 151.0, 128.9, 120.7, 101.5, 99.8, 48.9, 40.0 ppm; $^{19}$F NMR (DMSO-d$_6$, 470.6 MHz) δ −70.2 (d, $^1$J(PF)=711.1 Hz) ppm; $^{31}$P NMR (DMSO-d$_6$, 162 MHz) δ −144.19 (septet, $^1$J(PF)=711 Hz) ppm. C$_{13}$H$_{18}$F$_6$N$_5$P (MW, 389.29 for Compound 2 hexafluorophosphate and 244.32 for Compound 2 without anion) LCMS (EI) m/e 244.2 (M+, base peak). The crystallinity of Compound 2 hexafluorophosphate was characterized by XRPD, DSC and TGA.

Figure 7:
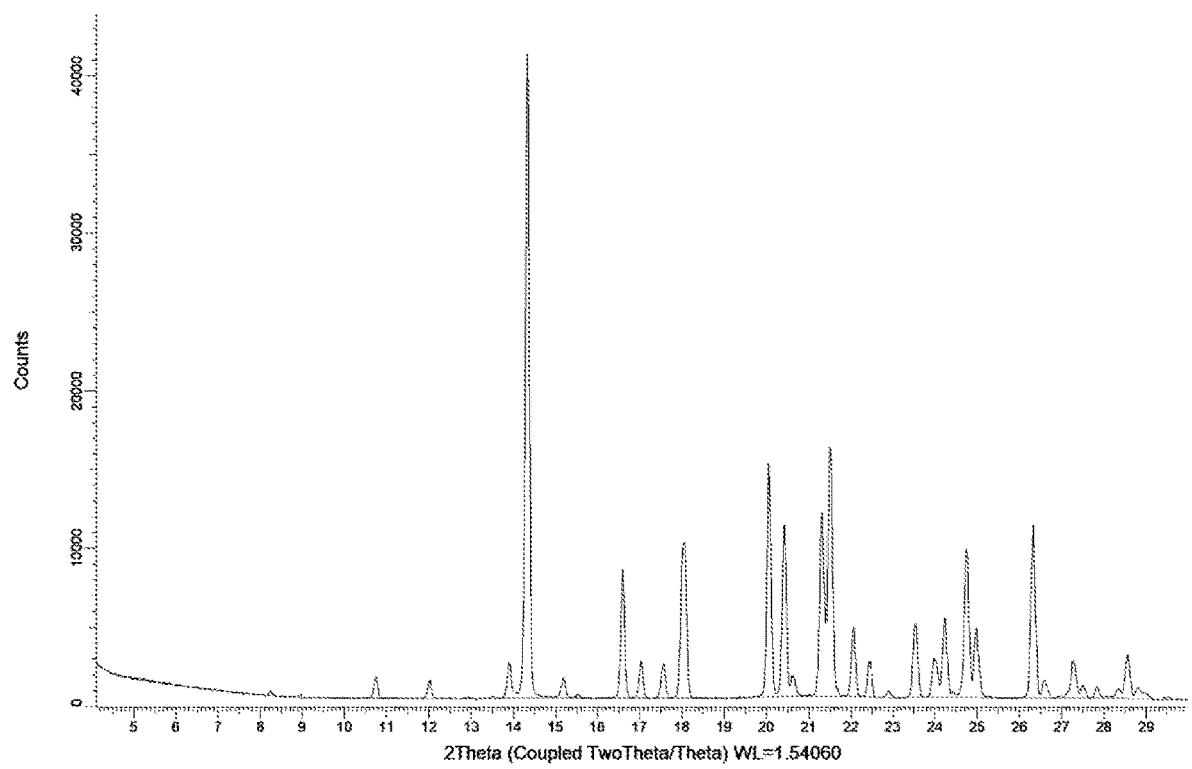
FIG. 7 is an XRPD pattern of Compound 2 hexafluorophosphate.

X-Ray Powder Diffraction (XRPD): The X-Ray Powder Diffraction (XRPD) was obtained from Bruker D8 Advance ECO X-ray Powder Diffractometer (XRPD) instrument. The general experimental procedures for XRPD were: (1) X-ray radiation from copper at 1.5418 Å and LYNXEYE™ detector; (2) X-ray power at 40 kV, 25 mA; and (3) the sample powder was dispersed on a zero-background sample holder. The general measurement conditions for XRPD were: Start Angle 3 degrees; Stop Angle 30 degrees; Sampling 0.015 degrees; and Scan speed 2 degree/min. Compound 2 hexafluorophosphate was confirmed to be crystalline solid according to XRPD analysis. The XRPD pattern of Compound 2 hexafluorophosphate is shown in FIG. 7 and the peak data is given in Table 3.

TABLE 3

XRPD Peak Data for Compound 2 hexafluorophosphate

| 2-Theta (°) | Relative Intensity (%) |
| --- | --- |
| 8.2 | 0.7 |
| 8.9 | 0.4 |
| 10.8 | 3.2 |
| 12.0 | 2.9 |
| 12.9 | 0.3 |
| 13.5 | 0.3 |
| 13.9 | 5.5 |
| 14.3 | 100 |
| 15.2 | 3.0 |
| 15.5 | 0.5 |
| 16.6 | 19.9 |
| 17.0 | 5.7 |
| 17.6 | 5.4 |
| 18.1 | 24.1 |
| 19.4 | 0.2 |
| 20.1 | 36.3 |
| 20.4 | 26.7 |
| 20.6 | 3.3 |
| 21.3 | 28.2 |
| 21.5 | 38.7 |
| 22.1 | 10.7 |
| 22.4 | 5.6 |
| 22.9 | 1.1 |
| 23.5 | 11.5 |
| 24.0 | 6.1 |
| 24.2 | 12.3 |
| 24.7 | 23.1 |
| 25.0 | 10.7 |
| 26.3 | 26.8 |
| 26.6 | 2.6 |
| 26.9 | 0.3 |
| 27.3 | 5.8 |
| 27.5 | 1.9 |
| 27.8 | 1.7 |
| 28.1 | 0.3 |
| 28.3 | 1.5 |
| 28.6 | 6.7 |
| 28.8 | 1.8 |
| 29.0 | 0.9 |
| 29.5 | 0.4 |

Figure 8:
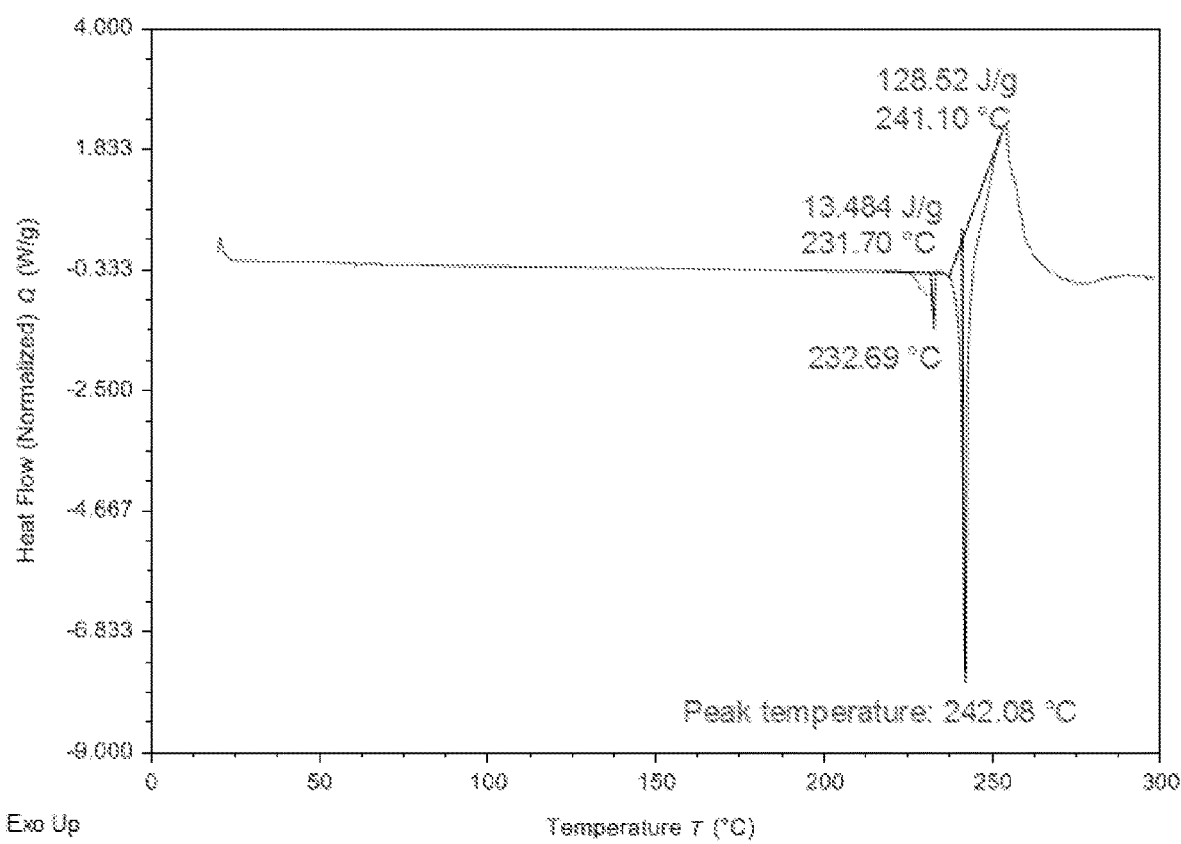
FIG. 8 is a DSC thermogram of Compound 2 hexafluorophosphate.

Differential Scanning calorimetry (DSC): The DSC was obtained from TA Instruments Differential Scanning calorimetry, Discovery DSC2500 with autosampler. The DSC instrument conditions were as follows: 20-300° C. at 10° C./min; Tzero aluminum sample pan and lid; and nitrogen gas flow at 50 mL/min. DSC analysis of Compound 2 hexafluorophosphate crystalline sample revealed one endothermic peak with an onset temperature of 231.7° C. and a maximum at 232.7° C. due to melting and second endothermic peak with an onset temperature of 241.1° C. and a maximum at 242.1° C. due to decomposition. The DSC thermogram of Compound 2 hexafluorophosphate is provided in FIG. 8.

Figure 9:
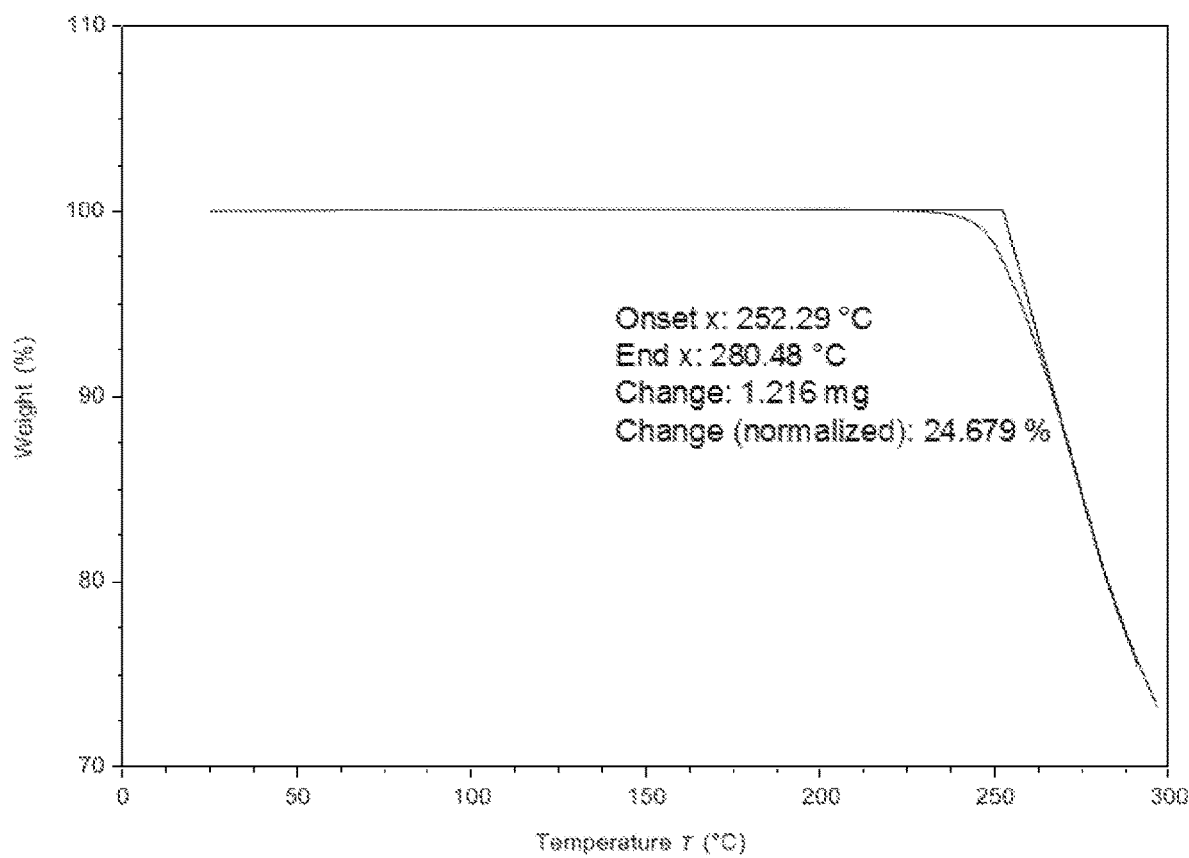
FIG. 9 is a TGA thermogram Compound 2 hexafluorophosphate.

Thermogravimetric Analysis (TGA): The TGA was obtained from TA Instruments Thermogravimetric Analyzer, Discovery TGA5500 with autosampler. The general experimental conditions for TGA were: ramp from 25° C. to 300° C. at 10° C./min; nitrogen purge gas flow at 25 mL/min; platinum sample holder. TGA analysis of Compound 2 hexafluorophosphate crystalline sample revealed significant weight loss above 250° C. due to decomposition. The TGA thermogram of Compound 2 hexafluorophosphate is provided in FIG. 9.

(E)-N-(3-(dimethylamino)-2-(7H-pyrrolo[2,3-d]pyrimidin-4-yl)allylidene)-N-methylmethanaminium Hexafluoroarsenate (Compound 2 Hexafluoroarsenate)

To a solution of (E)-N-(3-(dimethylamino)-2-(7H-pyrrolo[2,3-d]pyrimidin-4-yl)allylidene)-N-methylmethanaminium chloride (Compound 2c, 2.94 g, 10.525 mmol) in water (8.06 mL) was added sodium hexafluoroarsenate (NaAsF$_6$, 3.35 g, 15.79 mmol, 1.50 equiv) at ambient temperature. After stirred at 20-25° C. for 12 hour, the slurry was cooled in an ice bath for 2 hours. The solids was filtered, washed with cold H$_2$O (3×2 mL) and dried under vacuum to afford the crude desired product, (E)-N-(3-(dimethylamino)-2-(7H-pyrrolo[2,3-d]pyrimidin-4-yl)allylidene)-N-methylmethanaminium hexafluoroarsenate (Compound 2 hexafluoroarsenate, 4.51 g, 4.56 g theoretical, 99% yield), as white solids, which were used in the subsequent reaction without further purification. For Compound 2 hexafluoroarsenate: $^1$H NMR (400 MHz, DMSO-d$_6$) δ 12.38 (s, 1H), 8.83 (s, 1H), 7.97 (s, 2H), 7.76-7.57 (t, J=2.9 Hz, 1H), 6.59-6.36 (dd, J=3.2, 1.8 Hz, 1H), 3.32 (s, 6H), 2.35 (s, 6H) ppm; $^{19}$F NMR (DMSO-d$_6$, 376.5 MHz) δ −62.16 (quartet, $^1$J(AsF)=937.5 Hz) ppm; C$_{13}$H$_{18}$F$_6$N$_5$As (MW, 433.23 for Compound 2 hexafluoroarsenate and 244.32 for Compound 2 without anion) LCMS (EI) m/e 244.2 (M$^+$, base peak).

(E)-N-(3-(dimethylamino)-2-(7H-pyrrolo[2,3-d]pyrimidin-4-yl)allylidene)-N-methylmethanaminium Hexafluoroantimonate (Compound 2 Hexafluoroantimonate)

To a solution of (E)-N-(3-(dimethyl amino)-2-(7H-pyrrolo[2,3-d]pyrimidin-4-yl)allylidene)-N-methylmethanaminium chloride (Compound 2c, 2.94 g, 10.525 mmol) in water (8.06 mL) was added sodium hexafluoroantimonate (NaSbF$_6$, 4.08 g, 15.79 mmol, 1.50 equiv) at ambient temperature. After stirred at 20-25° C. for 12 hour, the slurry was cooled in an ice bath for 2 hours. The solids was filtered, washed with cold H$_2$O (3×2 mL) and dried under vacuum to afford the crude desired product, (E)-N-(3-(dimethylamino)-2-(7H-pyrrolo[2,3-d]pyrimidin-4-yl)allylidene)-N-methylmethanaminium hexafluoroantimonate (Compound 2 hexafluoroantimonate, 2.61 g, 5.05 g theoretical, 51.7% yield), as white solids, which were used in the subsequent reaction without further purification. For Compound 2 hexafluoroantimonate: $^1$H NMR (400 MHz, DMSO-d$_6$) δ 12.37 (s, 1H), 8.83 (s, 1H), 7.98 (s, 2H), 7.68 (s, 1H), 6.49 (s, 1H), 3.32 (s, 6H), 2.35 (s, 6H) ppm; $^{19}$F NMR (DMSO-d$_6$, 376.5 MHz) δ −166.86 ppm; C$_{13}$H$_{18}$F$_6$N$_5$Sb (MW, 480.07 for Compound 2 hexafluoroantimonate and 244.32 for Compound 2 without anion) LCMS (EI) m/e 244.2 (M$^+$, base peak).

Example 7: Alternative Preparation of (E)-N-(3-(dimethylamino)-2-(7H-pyrrolo[2,3-d]pyrimidin-4-yl)allylidene)-N-methylmethanaminium Perchlorate (Compound 2 Perchlorate)

Method 1

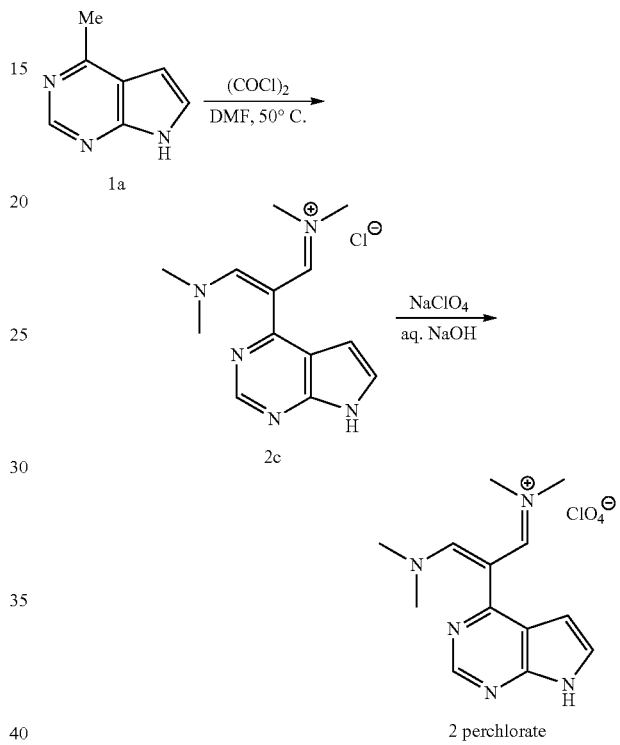

Oxalyl chloride (20.0 mL, 228 mmol, 3.04 equiv) was slowly charged to DMF (107 mL, 1378 mmol, 18.4 equiv) over 15 minutes while keeping the internal temperature at below 50° C. After addition, the resulting slurry was cooled to ambient temperature and stirred at ambient temperature for 2 hours. 4-Methyl-7H-pyrrolo[2,3-d]pyrimidine (Compound 1a, 10.0 g, 75 mmol) was added to the slurry at ambient temperature and the resulting reaction mixture was stirred at ambient temperature for 16 hours and then at 50° C. for 5.5 hours. The reaction mixture was cooled to ambient temperature and quenched with ice (60 g). The quenched reaction mixture was concentrated under vacuum to a residue, which was then dissolved in water (50 mL). Sodium perchlorate (NaClO$_4$, 20.23 g, 165 mmol, 2.2 equiv) was then added to the aqueous solution at ambient temperature. The resulting mixture was cooled in an ice bath before sodium hydroxide (NaOH, 7.5 g, 188 mmol, 2.5 equiv) was added slowly. The solids were collected by filtration, washed with water (30 mL), and dried under vacuum to give the crude desired product, (E)-N-(3-(dimethylamino)-2-(7H-pyrrolo[2,3-d]pyrimidin-4-yl)allylidene)-N-methylmethanaminium perchlorate (Compound 2 perchlorate, 18.7 g, 25.78 g theoretical, 72.5% yield), as grey solids, which were used for the subsequent reaction without further purification. $^1$H NMR (400 MHz, DMSO-d$_6$) δ 12.50-12.17 (s, 1H), 8.94-8.73 (s, 1H), 8.08-7.87 (s, 2H), 7.77-7.57 (dd, J=3.4, 2.3 Hz, 1H), 6.56-6.31 (dd, J=3.5, 1.7 Hz, 1H), 3.54-3.04 (s, 6H), 2.45-2.17 (s, 6H) ppm; $C_{13}H_{18}ClN_5O_4$ (MW, 343.77 for Compound 2 perchlorate and 244.32 for Compound 2 without anion) LCMS (EI) m/e 244.2 (M$^+$, base peak).

Method 2

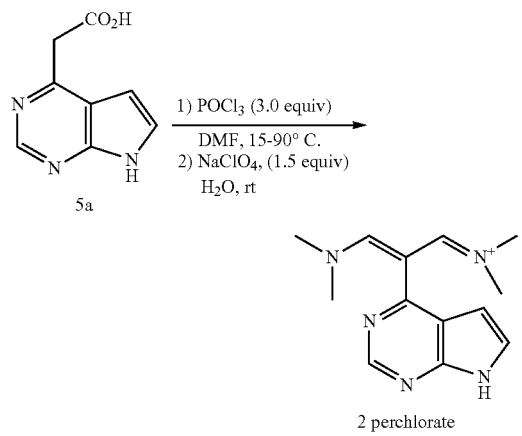

To a solution of 2-(7H-pyrrolo[2,3-d]pyrimidin-4-yl)acetic acid (Compound 5a, 354 mg, 2.0 mmol) in anhydrous DMF (2.92 g, 3.1 mL, 40 mmol, 20 equiv) was added phosphorus oxychloride (POCl$_3$, 920 mg, 0.56 mL, 6.0 mmol, 3.0 equiv) at ambient temperature. The resulting reaction mixture was then warmed to 80-90° C. and agitated at 80-90° C. for 30 minutes. When the reaction was complete, the reaction mixture was cooled down to ambient temperature. The cooled reaction mixture was quenched by pouring into ice (10 g). The solution was then concentrated under reduced pressure and the resulting residue was treated with water (3 mL). The aqueous solution was neutralized with an aqueous solution of NaOH to pH 7-8 before being treated with activated charcoal (50 mg). The mixture was agitated at ambient temperature for 30 minutes before being filtered through a Celite bed. The Celite bed was washed with water (2 mL). The combined filtrate and the wash solution was then treated with solid sodium perchlorate (NaClO$_4$, 367 mg, 3.0 mmol, 1.5 equiv) at ambient temperature. The mixture was stirred at ambient temperature for 1 hour followed by at 0-5° C. for 1 hour. The solids were then collected by filtration, washed with water (2×2 mL), dried under vacuum to give the crude desired product, (E)-N-(3-(dimethylamino)-2-(7H-pyrrolo[2,3-d]pyrimidin-4-yl)allylidene)-N-methylmethanaminium perchlorate (Compound 2 perchlorate), 330 mg, 688 mg theoretical, 48% yield), as grey solids, which were used for the subsequent reaction without further purification. For Compound 2 perchlorate: $^1$H NMR (400 MHz, DMSO-d$_6$) δ 12.50-12.17 (s, 1H), 8.94-8.73 (s, 1H), 8.08-7.87 (s, 2H), 7.77-7.57 (dd, J=3.4, 2.3 Hz, 1H), 6.56-6.31 (dd, J=3.5, 1.7 Hz, 1H), 3.54-3.04 (s, 6H), 2.45-2.17 (s, 6H) ppm; $C_{13}H_{18}ClN_5O_4$ (MW, 343.77 for Compound 2 perchlorate and 244.32 for Compound 2 without anion) LCMS (EI) m/e 244.2 (M$^+$, base peak).

Method 3

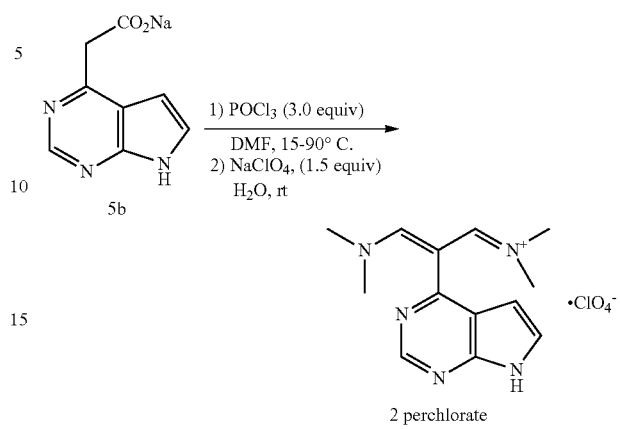

To a solution of sodium 2-(7H-pyrrolo[2,3-d]pyrimidin-4-yl)acetate (Compound 5b, 1.70 g, 8.54 mmol) in anhydrous DMF (12.48 g, 13.2 mL, 171 mmol, 20 equiv) was added phosphorus oxychloride (POCl$_3$, 3.93 g, 2.4 mL, 25.6 mmol, 3.0 equiv) at ambient temperature. The resulting reaction mixture was then warmed to 80-90° C. and agitated at 80-90° C. for 30 minutes. When the reaction was complete, the reaction mixture was cooled down to ambient temperature. The cooled reaction mixture was quenched by pouring into ice (40 g). The solution was then concentrated under reduced pressure and the resulting residue was treated with water (10 mL). The aqueous solution was neutralized with an aqueous solution of NaOH to pH 7-8 before being treated with activated charcoal (200 mg). The mixture was agitated at ambient temperature for 30 minutes before being filtered through a Celite bed. The Celite bed was washed with water (5 mL). The combined filtrate and the wash solution was then treated with solid sodium perchlorate (NaClO$_4$, 1.57 g, 12.8 mmol, 1.5 equiv) at ambient temperature. The mixture was stirred at ambient temperature for 1 hour followed by at 0-5° C. for 1 hour. The solids were then collected by filtration, washed with water (2×5 mL), dried under vacuum to give the desired product, (E)-N-(3-(dimethylamino)-2-(7H-pyrrolo[2,3-d]pyrimidin-4-yl)allylidene)-N-methylmethanaminium perchlorate (Compound 2 perchlorate, 1.3 g, 2.94 g theoretical, 44.3% yield), as off-white solids, which were used for the subsequent reaction without further purification. $^1$H NMR (400 MHz, DMSO-d$_6$) δ 12.50-12.17 (s, 1H), 8.94-8.73 (s, 1H), 8.08-7.87 (s, 2H), 7.77-7.57 (dd, J=3.4, 2.3 Hz, 1H), 6.56-6.31 (dd, J=3.5, 1.7 Hz, 1H), 3.54-3.04 (s, 6H), 2.45-2.17 (s, 6H) ppm; $C_{13}H_{18}ClN_5O_4$ (MW, 343.77 for Compound 2 perchlorate and 244.32 for Compound 2 without an anion) LCMS (EI) m/e 244.2 (M$^+$, base peak).

Example 8: Preparation of 2-(7H-Pyrrolo[2,3-d]pyrimidin-4-yl)malonaldehyde ((E)-3-hydroxy-2-(7H-pyrrolo[2,3-d]pyrimidin-4-yl)acrylaldehyde (Compound 2b)

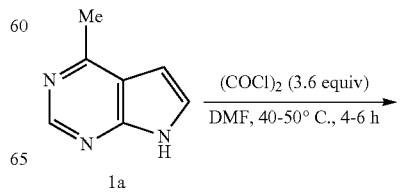

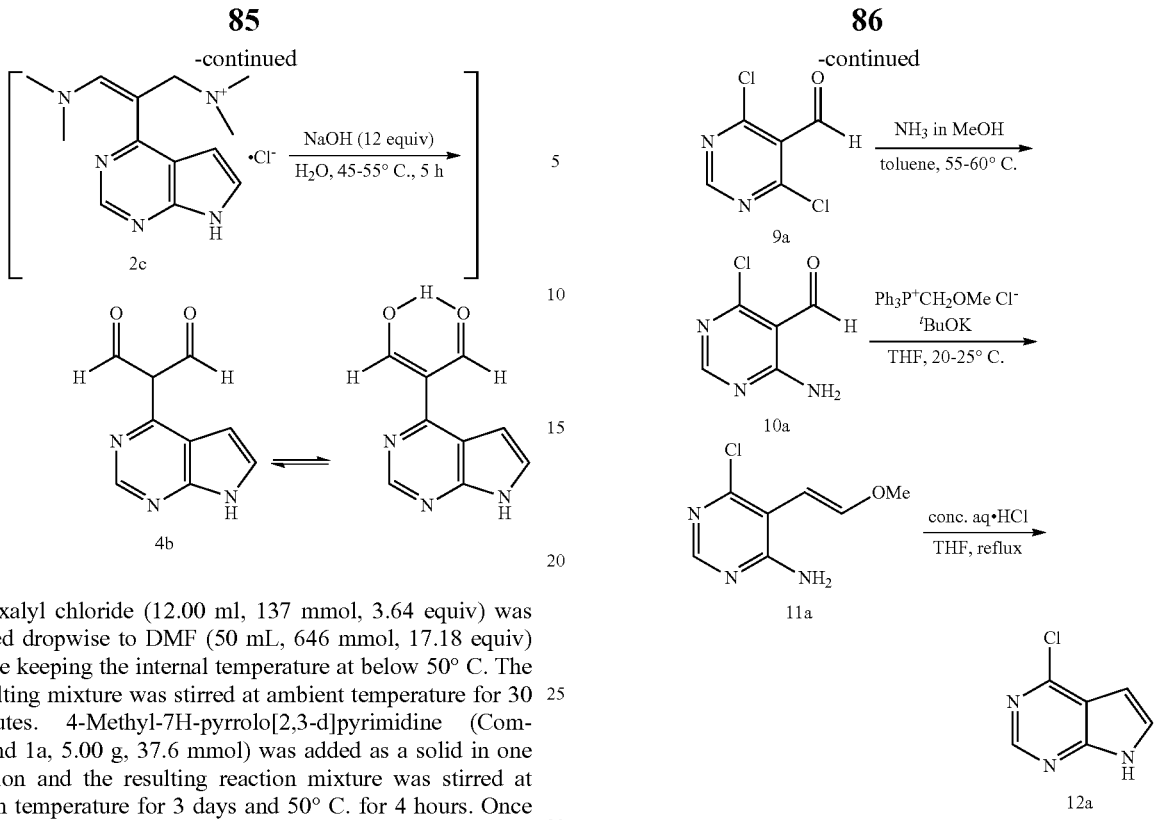

Oxalyl chloride (12.00 ml, 137 mmol, 3.64 equiv) was added dropwise to DMF (50 mL, 646 mmol, 17.18 equiv) while keeping the internal temperature at below 50° C. The resulting mixture was stirred at ambient temperature for 30 minutes. 4-Methyl-7H-pyrrolo[2,3-d]pyrimidine (Compound 1a, 5.00 g, 37.6 mmol) was added as a solid in one portion and the resulting reaction mixture was stirred at room temperature for 3 days and 50° C. for 4 hours. Once the reaction was complete, the reaction mixture was cooled to room temperature and quenched with ice (30 g). Sodium hydroxide (NaOH, 16.1 g, 403 mmol, 10.72 equiv) was added to the quenched reaction mixture and the mixture was stirred at room temperature for 26 hours. Additional sodium hydroxide (NaOH, 2.2 g, 55.0 mmol, 1.46 equiv) was added and the mixture was stirred at 40° C. for 4 hours. Once the hydrolysis reaction was complete, the mixture was cooled to 0-5° C. in an ice batch before the concentrated HCl solution was added to adjust pH to 5-6. The mixture was gradually warmed to ambient temperature and agitated at ambient temperature for 2 hours. Solids were collected by filtration, washed with cold water, and dried under vacuum to give the crude desired product, 2-(7H-pyrrolo[2,3-d]pyrimidin-4-yl)malonaldehyde ((E)-3-hydroxy-2-(7H-pyrrolo[2,3-d]pyrimidin-4-yl)acrylaldehyde, (Compound 2b, 6.33 g, 7.113 g theoretical, 89% yield), as a grey powder, which was used directly in the subsequent reaction without further purification. For Compound 2b: $^1$H NMR (400 MHz, DMSO-$d_6$) δ 13.74 (br s, 2H), 9.52 (s, 2H), 8.73 (s, 1H), 7.53 (dd, J=3.4, 2.3 Hz, 1H), 7.46 (dd, J=3.5, 1.7 Hz, 1H) ppm; $C_9H_7N_3O_2$ (MW, 189.17) LCMS (EI) m/e 190.1 (M$^+$, base peak).

Example 9: Preparation of 4-Chloro-7H-pyrrolo[2,3-d]pyrimidine (Compound 12a)

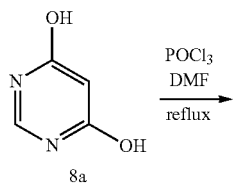

Step 1. 4, 6-Dichloropyrimidine-5-carbaldehyde (Compound 9a)

In a 5 L 4-neck flask equipped with a mechanical stirrer, an addition funnel, a condenser, a thermocouple, and a $N_2$ sweep into an aqueous NaOH scrubbing solution, phosphorous oxychloride (POCl$_3$, 1 L, 10.572 mol, 4.82 equiv) was charged and cooled in an ice/salt bath. N,N-Dimethylformamide (DMF, 320 mL, 4.138 mol, 1.85 equiv) was then added dropwise to the flask at 0±2° C. After addition of approximately 100 mL of DMF over approximately 0.5 h, crystallization occurred and the reaction temperature was increased from 0 to 10° C. Addition was stopped and the mixture was allowed to re-cool to approximately 2° C. The remaining DMF was added over 2.5 h at below 8° C. The suspension became very thick making stirring difficult. When addition of DMF was complete, the mixture was stirred at 3-5° C. for 0.5 h. 4,6-Dihydroxypyrimidine (Compound 8a, 250 g, 2.232 mol) was added portion wise as a solid. After about one third of 4,6-dihydroxypyrimidine was added, the reaction mixture became more mobile and a slow exothermic phenomena occurred with the reaction temperature increasing to approximately 12° C. over 0.5 h. The remaining 4,6-dihydroxypyrimidine was added portion wise over 0.25 h with the reaction temperature increasing from 12 to 27° C. The reaction temperature was maintained at 25-27° C. with intermittent cooling during which time the yellow suspension became thinner, then thicker once again. After the exothermic phenomenon subsided in about 1 h, the reaction mixture was heated slowly. At about 55° C. the reaction mixture became extremely thick and the second mild exothermic phenomenon was occurred. The heating mantle was removed while the reaction temperature continued to increase to about 63° C. and remained at this temperature for several minutes before dropping. Heating of the mixture was resumed until gentle reflux (about 100° C.) was attained. At about 95° C. a steady, fairly rapid evolution of HCl gas began and the reaction mixture gradually thinned and darkened. After about 0.5 h, a clear brown solution developed with the reflux temperature slowly increasing to 115° C. over 1.25 h. After a total of 2.5 h at reflux, the reaction mixture was cooled to ambient temperature and stirred overnight at ambient temperature. Excess amount of $POCl_3$ (as much as possible) was removed under reduced pressure (bath temperature 45-50° C.). The thick residual brown oil was poured very slowly into cold $H_2O$ (5 L) in a 20 L separation funnel, adding ice as needed to maintain the aqueous mixture near room temperature. The aqueous mixture was extracted with EtOAc (2×3 L followed by 1×2 L). The combined EtOAc extracts were washed with $H_2O$ (2×2.5 L), saturated $NaHCO_3$ aqueous solution (1 L), brine (1 L), dried over $Na_2SO_4$, filtered, and concentrated under reduced pressure (bath temperature at 35° C.) to afford the crude 4,6-dichloropyrimidine-5-carbaldehyde (Compound 9a, 270 g, 395 g theoretical, 68.4%) as yellow-orange solids. A 20 g portion of this crude material was purified by Kugelrohr distillation (oven temperature at 90-100° C., 225 mTorr) to give 15.3 g of pure 4,6-dichloropyrimidine-5-carbaldehyde (Compound 9a) as white solids that turned yellow on standing at room temperature. For 4,6-Dichloropyrimidine-5-carbaldehyde: $^1$H NMR (300 MHz, $CDCl_3$) δ 10.46 (s, 1H), 8.89 (s, 1H) ppm.

Step 2.
4-Amino-6-chloropyrimidine-5-carbaldehyde
(Compound 10a)

A solution of 7 M $NH_3$ in MeOH (265 mL, 1.855 mol, 2.0 equiv) was added over 1.25 h to a solution of 4,6-dichloropyrimidine-5-carbaldehyde (Compound 9a, 163.7 g, 0.9301 mol) in toluene (3 L) at ambient temperature. The reaction temperature slowly increased from 20 to 26° C. and a yellow suspension formed. Mild cooling was applied to maintain the reaction temperature at below 26° C. The suspension was stirred at ambient temperature for 3.5 h before the solids were collected by filtration. The solids were washed with EtOAc (1 L). The filtrate was concentrated under reduced pressure, and the solids were triturated with toluene and n-heptane (2:1 v/v, 600 mL), filtered and dried to give 71.1 g of 4-amino-6-chloropyrimidine-5-carbaldehyde as a yellow solid. The original solid filtered from the reaction mixture contained additional amount of 4-amino-6-chloropyrimidine-5-carbaldehyde. The product was extracted from the filtered solid by stirring in EtOAc (1.25 L) for 1.5 h, filtering, then stirring in THF (750 mL) for 1 h and filtering. Both EtOAc and THF filtrates were concentrated under reduced pressure, and the resulting solids were triturated with toluene and n-heptane (2:1 v/v, 450 mL), filtered and dried to give an additional 44.1 g of 4-amino-6-chloropyrimidine-5-carbaldehyde as yellow solids. The combined yield of 4-amino-6-chloropyrimidine-5-carbaldehyde (115.2 g, 146.5 g theoretical) was 78.6%. For 4-Amino-6-chloropyrimidine-5-carbaldehyde: $^1$HNMR (300 MHz, DMSO-$d_6$) δ 10.23 (s, 1H), 8.71 (bs, 1H), 8.55 (bs, 1H), 8.39 (s, 1H) ppm; $C_5H_4ClN_3O$ (MW, 157.56), LCMS (EI) m/e 158 ($M^+$+H).

Step 3.
6-Chloro-5-(2-methoxyvinyl)pyrimidin-4-ylamine
(Compound 11a)

A suspension of (methoxymethyl)triphenylphosphonium chloride (276.0 g, 0.807 mol, 1.1 equiv) in THF (1.5 L) was cooled in an ice/salt bath to −2° C. and 1 M potassium tert-butoxide (KO$^t$Bu) in THF (807 mL, 0.807 mol, 1.1 equiv) was added over 1.5 hour at −2 to −3° C. The deep red-orange mixture was stirred at −2 to −3° C. for 1 h. 4-Amino-6-chloropyrimidine-5-carbaldehyde (Compound 10a, 115.2 g, 0.7338 mol, 1.0 equiv) was then added portion wise to the reaction mixture as a solid form using THF (200 mL) to rinse the container and funnel. During the addition the reaction temperature increased from −3 to 13° C. and a brown color developed. When the reaction temperature dropped to 10° C., the cooling bath was removed and the reaction mixture was allowed to warm to ambient temperature and stirred at ambient temperature for 42 h. The reaction mixture was cooled to −2° C. before being quenched by the slow addition of saturated $NH_4Cl$ aqueous solution (750 mL). The mixture was concentrated under reduced pressure to remove most of the THF. The residue was partitioned between EtOAc (3 L) and $H_2O$ (1 L). The organic phase was filtered to remove insoluble material at the interface, then extracted with 2 N HCl (4×250 mL) followed by 3 N HCl (2×250 mL). The combined HCl extracts were back-extracted with EtOAc (500 mL) then filtered through Celite to remove insoluble material. The filtrate was cooled in an ice/brine bath, adjusted to pH 8 with a 6 N aqueous NaOH solution and extracted with EtOAc (3×1 L). The combined EtOAc extracts were washed with brine (1 L), dried over $Na_2SO_4$, stirred with charcoal (10 g) and silica gel (10 g) for 1 h. The mixture was filtered through Celite, washing the Celite pad with EtOAc (1 L). The filtrate was concentrated, co-evaporating residual EtOAc with n-heptane (500 mL). The resulting tan solid was pumped under high vacuum for 2 h to afford crude 6-chloro-5-(2-methoxyvinyl)pyrimidin-4-ylamine (Compound 11a, 72.3 g, 136.2 g theoretical, 53.1%). The crude desired product Compound 11a was used in the following reaction without further purification. A sample of crude product Compound 11a (2.3 g) was purified by silica gel column chromatography on, eluting with 0-35% EtOAc/n-heptane to give 1.7 g of pure 6-chloro-5-(2-methoxyvinyl)pyrimidin-4-ylamine (Compound 11a) as white solids, which was found to be a 1 to 2 mixture of E/Z isomers. For 6-Chloro-5-(2-methoxyvinyl)pyrimidin-4-ylamine: $^1$H NMR (300 MHz, DMSO-$d_6$) for E-isomer: δ 8.02 (s, 1H), 7.08 (bs, 2H), 6.92 (d, 1H, J=13.1), 5.35 (d, 1H, J=13.0 Hz), 3.68 (s, 3H) ppm and for Z-isomer: δ 8.06 (s, 1H), 7.08 (bs, 2H), 6.37 (d, 1H, J=6.8 Hz), 5.02 (d, 1H, J=6.7 Hz), 3.69 (s, 3H) ppm; $C_7H_8ClN_3O$ (MW, 185.61), LCMS (EI) m/e 186/188 ($M^+$+H).

Step 4. 4-Chloro-7H-pyrrolo[2,3-d]pyrimidine
(Compound 12a)

Concentrated aqueous hydrochloric acid (HCl, 5 mL) was added to a solution of crude 6-chloro-5-(2-methoxyvinyl)pyrimidin-4-ylamine (Compound 11a, 70.0 g, 0.3784 mol) in THF (700 mL) and the resulting reaction mixture was heated to reflux for 7.5 h. On warming a light suspension was formed that gradually re-dissolved. When the reaction was deemed complete as monitored by HPLC, the reaction mixture was cooled to ambient temperature and stirred at ambient temperature for overnight. Solid $NaHCO_3$ (15 g) was added to the reaction mixture and the resulting mixture was stirred at ambient temperature for 1 h. Charcoal (7 g), silica gel (7 g) and $Na_2SO_4$ (20 g) were added and the mixture was heated to 40° C. for 1 h. The mixture was then cooled to ambient temperature and filtered through Celite, washing the Celite pad with THF (1 L). The filtrate was concentrated under reduced pressure and the resulting solid was dried under reduced pressure to afford crude 4-chloro-7H-pyrrolo[2,3-d]pyrimidine (Compound 12a, 58.1 g, 58.1 g theoretical, 100%) as yellow-brown solids. This crude desired product Compound 12 was dissolved in EtOAc (1.0 L) at 50-55° C. and treated with activated charcoal (3 g). The mixture was filtered while warm through Celite and the Celite pad was washed with warm EtOAc (250 mL). The filtrate was concentrated to about 500 mL and the suspension was allowed to stand at ambient temperature for overnight. The suspension was subsequently cooled to 0-5° C. for 2 h before the solids were collected by filtration. The solids were dried to afford pure 4-chloro-7H-[pyrrolo[2,3-d]pyrimidine (Compound 12a, 54.5 g, 58.1 g theoretical, 94%) as yellow-brown crystals. For Compound 12a: $^1$H NMR (400 MHz, DMSO-$d_6$) δ 12.58 (bs, 1H), 8.58 (s, 1H), 7.69 (d, 1H, J=3.5 Hz), 6.59 (d, 1H, J=3.5 Hz) ppm; LCMS (EI) m/e 154/156 (M$^+$+H).

Example 10: Alternative Preparation of 4-Chloro-7H-pyrrolo[2,3-d]pyrimidine (Compound 12a)

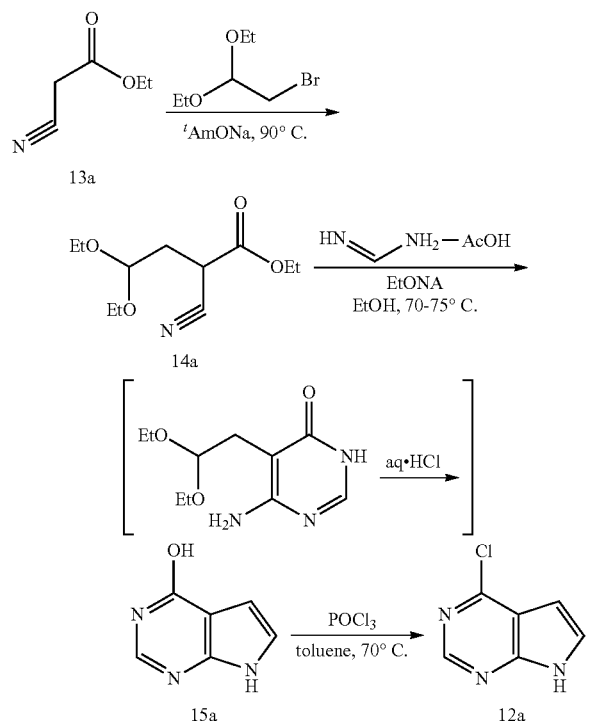

Step 1. Ethyl 2-cyano-4,4-diethoxybutanoate (Compound 14a)

To a mixture of ethyl cyanoacetate (Compound 13a, 182 Kg, 1609 moles) and DMSO (325 Kg) was added portionwise sodium tert-amyloxide ($^t$AmONa, 158.8 Kg) at 5° C. The mixture was then warmed to 70-75° C. and ethyl cyanoacetate (191 Kg, 1689 moles; total 3298 moles, 5.0 equiv) was charged. The mixture was stirred at 70-75° C. for 30 minutes before bromoacetaldehyde diethyl acetal (130.4 Kg, 665.2 moles) was added. The resulting reaction mixture was then heated to 90° C. and agitated at 90° C. until the reaction was complete. The reaction mixture was cooled to 5° C. and a 16% aqueous solution of ammonium chloride (NH$_4$Cl) was added. The mixture was agitated for 30 minutes before ethyl acetate (490 Kg) was charged. The organic phase was separated and washed with water (695 Kg). The aqueous phase was extracted with ethyl acetate (455 Kg). The combined organic phase was washed with a 17% aqueous solution of sodium chloride (NaCl, 318 Kg) and brine (325 Kg). The organic solution was dried over sodium sulfate (Na$_2$SO$_4$) and filtered. The filtrate was concentrated under reduced pressure. The residue was dissolved in petroleum ether (390 Kg) and treated with charcoal at 60° C. The mixture was filtered and the filtrate was concentrated to dryness to afford the crude ethyl 2-cyano-4,4-diethoxybutanoate (Compound 14a, 146.6 Kg, 152.5 Kg theoretical, 96.1%) as a yellow to brown oil, which was directly utilized in the subsequent reaction without further purification.

Step 2. 7H-Pyrrolo[2, 3-d]pyrimidin-4-ol (Compound 15a)

To a reactor was charged a solution of 18% sodium ethoxide (EtONa) in ethanol (1558 Kg) and formamidine acetate (153.5 Kg, 1474.4 moles). The mixture was agitated at ambient temperature for 1 hour before ethyl 2-cyano-4, 4-diethoxybutanoate (Compound 14a, 269.8 Kg, 1176.7 moles, 1.25 equiv) was charged. The reaction mixture was heated to 75° C. and agitated at 75° C. until no unreacted ethyl 2-cyano-4,4-diethoxybutanoate (Compound 14) was detected. The mixture was cooled to 0° C. and an aqueous solution of 21% ammonium chloride (NH$_4$Cl, 783 Kg) was charged. The resulting mixture was agitated at 0° C. for 30 minutes and concentrated under the reduced pressure. The residual solution was cooled to 20-30° C. and filtered. The cake was reslurried with water (493 Kg) and filtered. The solids were suspended in water (474 Kg) and the concentrated hydrochloric acid (HCl, 89.2 Kg) was added. The mixture was agitated at 20° C. for 1 hour and then warmed to 30° C. until the cyclization reaction was complete. The mixture was then cooled to 5° C. and an aqueous solution of ammonium hydroxide (NH$_4$OH, 72 Kg) was added. After addition, the mixture was agitated at 5° C. for 1 h and then filtered. The wet cake was washed with water and dried in a vacuum oven to afford 7H-Pyrrolo[2,3-d]pyrimidin-4-ol (Compound 15a, 99.6 Kg, 159 Kg theoretical, 62.6%) as off-white to yellow solids, which was used in the subsequent reaction without further purification.

Step 3. 4-Chloro-7H-pyrrolo[2,3-d]pyrimidine (Compound 12a)

7H-Pyrrolo[2,3-d]pyrimidin-4-ol (Compound 15a, 99.6 Kg, 737 moles) was added to a solution of DIEA (128.4 Kg, 99.53 moles, 1.35 equiv) in toluene (500 Kg) at ambient temperature and the resulting mixture was cooled to 0° C. POCl$_3$ (338 Kg, 2202 moles, 3.0 equiv) was then added to the mixture at 0° C. and the resulting reaction mixture was heated to 70° C. and agitated at 70° C. until the reaction was complete. The reaction mixture was cooled to 30° C. and added water (3500 Kg), sodium carbonate (Na$_2$CO$_3$, 700 Kg) and 2-methyltetrahydrofuran (MeTHF, 1200 Kg). The resulting mixture was then filtered. The organic phase of the filtrate was separated and washed with brine (424 Kg), dried over sodium sulfate (Na$_2$SO$_4$), and filtered. The filtrate was concentrated to remove approximately 1000 Kg of MeTHF. The remaining solution was treated with charcoal (28 Kg) at 60° C. for 1 hour and filtered. The filtrate was concentrated to a thick slurry, cooled to 0° C., and filtered. The cake was dried under reduced pressure to afford pure 4-chloro-7H-pyrrolo[2,3-d]pyrimidine (Compound 12a, 71.9 Kg, 113.2 Kg theoretical, 63.5%) as yellow to brown crystals. 4-Chloro-7H-pyrrolo[2,3-d]pyrimidine (Compound 12a) manufactured by this synthetic method is identical in every comparable aspect with the compound obtained by Example 9. $^1$H NMR (400 MHz, DMSO-$d_6$) δ 12.58 (bs, 1H), 8.58 (s, 1H), 7.69 (d, 1H, J=3.5 Hz), 6.59 (d, 1H, J=3.5 Hz) ppm; LCMS (EI) m/e 154/156 (M$^+$+H).

Example 11. Preparation of 4-Methyl-7H-pyrrolo[2,3-d]pyrimidine (Compound 1a)

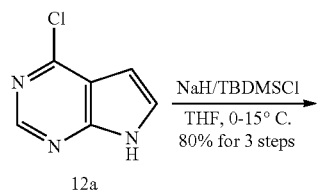

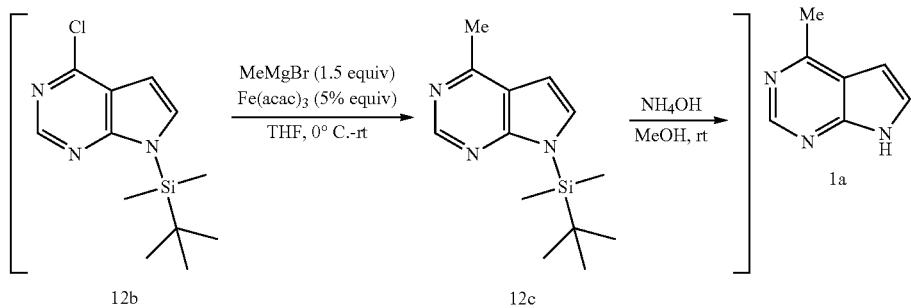

A suspension of sodium hydride (NaH, 60% suspension in mineral oil, 309, 7726 mmol, 1.211 equiv) in THF (4.0 L) was cooled to 0-5° C. in an ice bath before 4-chloro-7H-pyrrolo[2,3-d]pyrimidine (Compound 12a, 980.0 g, 6381 mmol) was charged. The mixture was agitated at 0-15° C. for 30 minutes before a solution of TBDMS-Cl (1165 g, 7728 mmol, 1.211 equiv) in THF was charged at 0-15° C. The resulting mixture was agitated at 0-15° C. for 1-2 hours. The mixture was cooled to −10° C. and Iron(III) acetylacetonate (Fe(acac)$_3$, 113 g, 319 mmol, 0.05 equiv) was charged. A solution of methylmagnesium bromide in THF (3260 mL, 9780 mmol, 1.53 equiv) was the slowly charged to the mixture and the internal temperature was controlled to below 15° C. The resulting reaction mixture was agitated at 15-30° C. for 2 hours. Once the coupling reaction was complete, an aqueous solution of ammonium chloride (NH$_4$Cl, 8.0 L) was charged to quench the reaction mixture and the internal temperature was controlled to below 10° C. during quenching. Methyl tert-butyl ether (MTBE, 5.0 L) was charged into the quenched reaction mixture and the resulting mixture was filtered through a Celite bed. The Celite bed was washed with MTBE (2×500 mL). The two phases of the combined filtrate and wash solution were separated and the aqueous phase was extracted with MTBE (2×5.0 L). The combined organic extracts were concentrated under the reduced pressure and the residue was dissolved in methanol (MeOH, 5.0 L). The solution was then treated with an aqueous solution of 26-28% ammonium hydroxide (NH$_4$OH, 1.0 L) and the resulting mixture was agitated at 15-40° C. for 16 hours. When the N-TBDMS-deprotection reaction was complete, the reaction mixture was concentrated under reduced pressure and n-heptane (2×4.0 L) was charged to remove water under the azeotropic conditions. The residue was then treated with n-heptane (8.0 L) and the resulting mixture was agitated at ambient temperature for at least one hour. The solids were collected by filtration and washed with n-heptane (2×1.0 L) to afford the crude desired product, 4-methyl-7H-pyrrolo[2,3-d]pyrimidine (Compound 1a, 840 g, 849.6 g theoretical, 98.9%), as brown powders, which was purified by recrystallization in a mixture of ethyl acetate and n-heptane.

A solution of crude methyl-7H-pyrrolo[2,3-d]pyrimidine (Compound 1a, 1640 g) in methanol (MeOH, 8.0 L) was treated with charcoal (2.0 Kg) and the resulting mixture was agitated at ambient temperature for 16 hours. The mixture was filtered through a Celite bed and the Celite bed was washed with MeOH (2×8.0 L). The combined methanol solution was concentrated under the reduced pressure and the residue was added ethyl acetate (8.0 L). The resulting solution was concentrated under the reduced pressure to remove most of ethyl acetate (approximately 6.0 L) before n-heptane (8.0 L) was introduced. The resulting mixture was agitated at ambient temperature for 14 hours. The solids were collected by filtration, washed by a mixture of ethyl acetate and n-heptane followed by n-heptane, and dried to constant weight to afford the purified methyl-7H-pyrrolo[2,3-d]pyrimidine (Compound 1a, 1325 g, 1640 g theoretical, 80.8% for purification by recrystallization and 80% for overall) as yellow to light brown crystalline powders. For Compound 1a: $^1$H NMR (DMSO-$d_6$, 500 MHz) δ 12.10 (br s, 1H), 8.61 (s, 1H), 7.47 (dd, J=3.3, 2.5 Hz, 1H), 6.62 (s, dd, J=3.5, 1.7 Hz, 1H), 2.64 (s, 3H) ppm; $^{13}$C NMR (DMSO-$d_6$, 125 MHz) δ 158.7, 151.3, 151.2, 126.5, 117.6, 99.6, 21.3 ppm; C$_7$H$_7$N$_3$ (MW, 133.15) LCMS (EI) m/e 134.1 (M$^+$+H, base peak).

Example 12. Alternative Preparation of 4-Methyl-7H-pyrrolo[2,3-d]pyrimidine (Compound 1a)

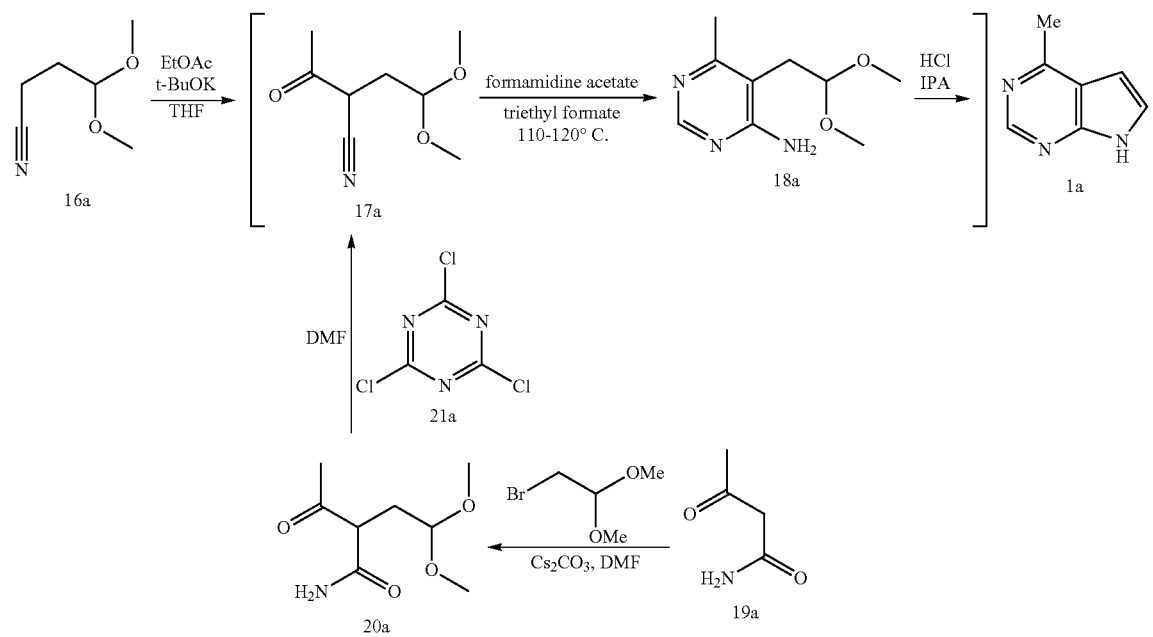

Step 1. 4-Methyl-7H-pyrrolo[2,3-d]pyrimidine (Compound 1a)

A turbid mixture of potassium tert-butoxide (18.31 g, 163 mmol, 2.12 equiv) in THF (100 mL) was cooled in an ice bath before a solution of 4,4-dimethoxybutanenitrile (Compound 16a, 10.00 g, 77 mmol) and ethyl acetate (7.46 g, 85 mmol, 1.1 equiv) in THF (20 mL) were charged over 15 minutes. The mixture was allowed to warm to room temperature and stirred at ambient temperature for 3 hours. 2-Acetyl-4,4-dimethoxybutanenitrile, generated in situ, was then treated with formamidine acetate (65.0 g, 624 mmol, 8.1 equiv), 1-butanol (80 mL) and triethyl orthoformate (56.2 mL, 337 mmol, 4.38 equiv) at ambient temperature. The resulting mixture was heated to 110-120° C. and stirred at 110-120° C. for 1 hour. Additional triethyl orthoformate (26.5 mL, 159 mmol, 2.06 equiv) was added. The mixture was stirred at 110° C. for additional 16 hours. Additional formamidine acetate (31.38 g, 302 mmol, 3.92 equiv) and triethyl orthoformate (56.5 mL, 115 mmol, 1.5 equiv) were added in three portions over 24 hours. The mixture was heated for an additional 24 hours and concentrated under the reduced pressure to a residue. The residue was treated with water (150 mL) and MeTHF (210 mL). The resulting mixture was passed through a bed of Celite (12 g). Two phases of the filtrate were separated and the aqueous phase was extracted with MeTHF (175 mL×2). The combined organic extracts were concentrated under the reduced pressure, and the resulting residue was treated a solution of HCl in IPA (5.5 M, 50.8 g), water (31 mL), and concentrated HCl (12 M, 15.6 g). The mixture was stirred at room temperature for 3 days. A concentrated aqueous NH$_4$OH solution (38.6 g, 28-30%) was added and the mixture was concentrated to a residue, which was triturated with THF (170 mL, 2×150 mL). Filtrates were combined and concentrated to a residue, which was dissolved in DCM (30 mL) and purified by column chromatography over silica gel (SiO$_2$, 120 g), eluting with 0-100% of EtOAc in DCM, to afford the desired product, 4-methyl-7H-pyrrolo[2,3-d]pyrimidine (Compound 1a, 5.1 g, 10.25 g theoretical, 49.8% for three steps), as an off-white crystalline solid, which is identical in every comparable aspect with the compound obtained by Example 11.

Step 2. 2-Acetyl-4,4-dimethoxybutanamide (Compound 20a)

A solution of 3-oxobutanamide (Compound 19a, 5.0 g, 49.5 mmol) in DMF (15 mL) was treated with cesium carbonate (Cs$_2$CO$_3$, 16.11 g, 49.5 mmol, 1.0 equiv) at ambient temperature. The resulting mixture was stirred at ambient temperature. 2-Bromo-1,1-dimethoxyethane (8.36 g, 49.5 mmol, 1.0 equiv) was then added to the mixture and the resulting reaction mixture was heated to 80° C. for 5-8 hours. The reaction mixture was cooled to ambient temperature and then quenched with water (20 mL). The quenched reaction mixture was then extracted with ethyl acetate (3×20 mL) and the combined organic extracts were washed with water (2×10 mL), dried with anhydrous sodium sulfate (Na$_2$SO$_4$), and concentrated under reduced pressure. The residue was purified by silica gel (SiO$_2$) column chromatography to afford 2-acetyl-4,4-dimethoxybutanamide (Compound 20a, 5.8 g, 9.37 g theoretical, 61.9%) as a thick oil, which contains some residual DMF. For 2-acetyl-4,4-dimethoxybutanamide: $^1$H NMR (DMSO-d$_6$, 400 MHz) δ 6.70 (s, 1H), 6.30 (s, 1H), 4.28 (dd, 1H), 3.47 (t, 1H), 3.23 (s, 6H), 2.25 (s, 3H), 2.19, (m, 1H), 2.00 (m 1H); C$_8$H$_{15}$NO$_4$ (MW, 189.21), LCMS (EI) m/e 190.2 (M$^+$+H).

Step 3. 2-Acetyl-4,4-dimethoxybutanenitrile (Compound 17a)

A solution of 2-acetyl-4,4-dimethoxybutanamide (Compound 20a, 1.0 g, 4.23 mmol) in DMF (4 mL) was treated with cyanuric chloride (Compound 21a, 0.39 g, 2.11 mmol, 0.5 equiv). The resulting reaction mixture was stirred at ambient temperature for 1 h. Once the reaction was complete, the reaction mixture was quenched with water (10 mL) and the quenched reaction mixture was extracted with ethyl acetate (3×10 mL). The combined organic extracts were washed with water (2×10 mL), dried with anhydrous sodium sulfate ($Na_2SO_4$), and concentrated under reduced pressure. The residue was purified by silica gel ($SiO_2$) column chromatography to afford 2-acetyl-4,4-dimethoxybutanenitrile (Compound 17a, 280 mg, 724 mg theoretical, 38.7%) as a thick oil. For 2-acetyl-4,4-dimethoxybutanenitrile: $^1$H NMR (DMSO-$d_6$, 400 MHz, a mixture of ketone and enol forms obtained) δ 10.7 (br. s, ½ H for enol form of —OH), 4.38 (m, 1H), 3.25 (m, 6H for two OMe and ½ H for ketone form of —CH—), 2.25-2.50 (m, 2H), 2.15 and 2.25 (s, 3H); $C_8H_{13}NO_3$ (MW, 171.196), LCMS (EI) m/e 172.2 (M$^+$+H). 2-Acetyl-4,4-dimethoxybutanenitrile (Compound 17a) generated by this method reacts with formamidine acetate followed by treatment with HCl to afford 4-methyl-7H-pyrrolo[2,3-d]pyrimidine (Compound 1a) according to Example 11 described above.

Example 13. Preparation of 4-Methyl-(7H-pyrrolo[2,3-d]pyrimidin-4-yl) Hydrochloride (Compound 1a Hydrochloride)

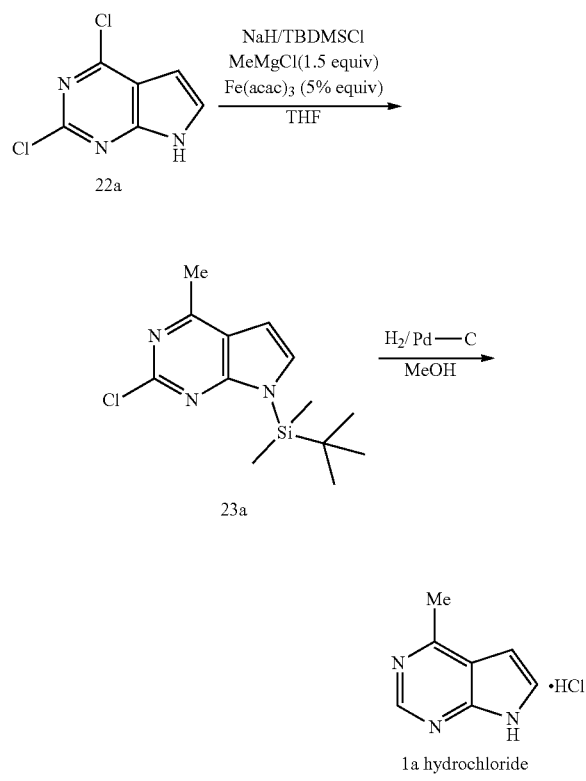

To a reactor under nitrogen were charged 2,4-dichloro-7H-pyrrolo[2,3-d]pyrimidine (Compound 22a, 200 g, 1.064 mole) and THF (1.2 L). The content in the reactor was cooled to below −5° C. before 60% NaH in mineral oil (51 g, 1.28 moles, 1.2 equiv) was added portion wise. During addition of NaH, the internal temperature was maintained at −5 to 5° C. After the addition, agitation was continued for 30 minutes and then a solution of TBDMS-Cl (193 g, 1.28 moles, 1.2 equiv) in THF (200 mL) was added slowly by keeping the internal temperature at −5 to 5° C. Agitation of the reaction mixture was continued for 30 minutes and Fe(acac)$_3$ (18.8 g, 53. 2 mmol, 0.05 equiv) was then added followed by the addition of a 3.0 M solution of MeMgCl in THF (532 mL, 1.596 moles, 1.5 equiv) at −5 to 5° C. After the reaction mixture was kept for an additional 1 h, by which time IPC by HPLC showed the completion of the coupling reaction, the reaction mixture was poured into a solution of EDTA di-sodium salt dihydrate (200 g) in water (2.0 L) while the internal temperature was controlled at below 15° C. The biphasic mixture was diluted with methyl tert-butyl ether (MTBE, 2.0 L), treated with Celite (150 g), and filtered by centrifuge. The solid cake was washed with MTBE and the filtrate was allowed for phase separation. The aqueous phase was separated and extracted with MTBE (1.0 L). The organic phase was combined and washed successively with 3% citric acid aqueous solution (2×400 mL) and brine (600 mL). After being dried over $Na_2SO_4$, the organic phase was filtered and concentrated to dryness. The residue was taken up with petroleum ether (2.0 L) and any insoluble materials were removed by filtration through a thin layer of silica gel. The filtrate was concentrated to give the crude desired product, 7-(tert-butyldimethylsilyl)-2-chloro-4-methyl-7H-pyrrolo[2,3-d]pyrimidine (Compound 22a, 300 g), as an oily residue, which was used directly in the subsequent reaction without further purification.

A mixture of crude 7-(tert-butyldimethylsilyl)-2-chloro-4-methyl-7H-pyrrolo[2,3-d]pyrimidine (Compound 22a, 300 g, 1.064 moles) and 5% palladium on carbon (Pd/C, 30 g) in methanol (1.8 L) was vigorously agitated under 1 atm of hydrogen at 50-55° C. for 3 hours. After IPC by HPLC confirmed the completion of the reaction, the reaction mixture was cooled to 20-25° C. and filtered. The filter cake was washed with methanol and the filtrate was concentrated to dryness. The residue was suspended in ethyl acetate (EtOAc, 225 mL) and agitated at 10-15° C. for 1 hour. The solids were collected by filtration, washed with ethyl acetate and dried under vacuum at 40-45° C. to give 4-methyl-7H-pyrrolo[2,3-d]pyrimidine hydrochloride (Compound 1a hydrochloride, 151.5 g, 180.5 g theoretical, 84% yield for two steps) as light yellow crystalline powders. For Compound 1a hydrochloride: $^1$H NMR (DMSO-$d_6$, 500 MHz) δ ppm 13.54 (br s, 1H), 9.04 (s, 1H), 7.95 (dd, J=3.4, 2.4 Hz, 1H), 7.13 (s, dd, J=3.4, 1.5 Hz, 1H), 2.97 (s, 3H); $^{13}$C NMR (DMSO-$d_6$, 125 MHz) δ ppm 154.0, 151.0, 144.0, 131.6, 117.2, 103.1, 17.6; $C_7H_8ClN_3$ (MW, 169.61; $C_7H_7N_3$ for free base, MW 133.15) LCMS (EI) m/e 134.1 (M$^+$+H, base peak).

Example 14. Preparation of Sodium 2-(7H-pyrrolo[2,3-d]pyrimidin-4-yl)acetate (5b) and 2-(7H-pyrrolo[2,3-d]pyrimidin-4-yl)acetic Acid (Compound 5a)

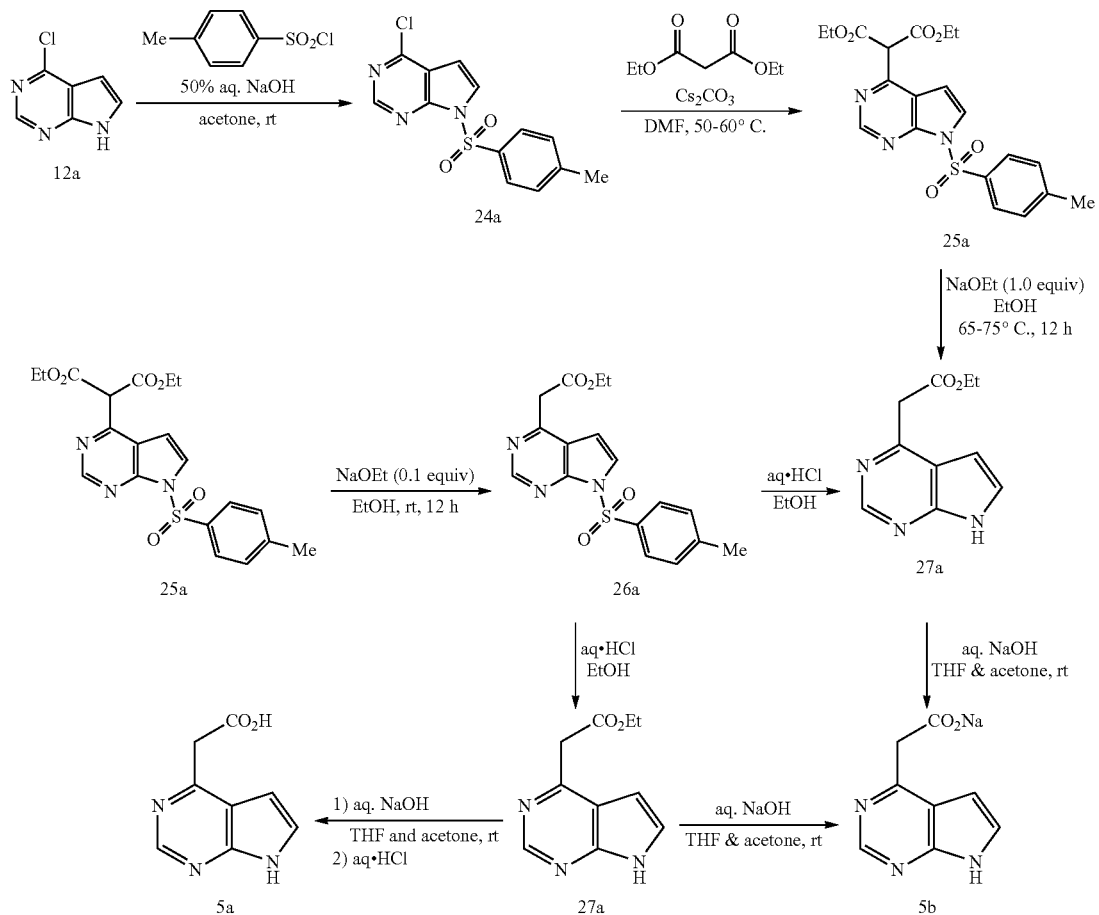

Step 1. 4-Chloro-7-tosyl-7H-pyrrolo[2,3-d]pyrimidine (Compound 24a)

A suspension of 4-chloro-7H-pyrrolo[2,3-d]pyrimidine (Compound 12a, 18.0 g, 117 mmol) in acetone (180 mL) was added a 50% aqueous sodium hydroxide solution (NaOH, 14.07 g, 176 mmol, 1.5 equiv) at ambient temperature. The resulting mixture was then agitated at ambient temperature until a clear solution was generated. p-Toluenesulfonyl chloride (pTsCl, 25.7 g, 135 mmol, 1.15 equiv) was added to the solution at ambient temperature and the resulting reaction mixture was agitated at ambient temperature for 1 hour. When the reaction was complete, the reaction mixture was filtered, and the solids were washed with acetone before being discarded. The filtrate was then concentrated under the reduced pressure, and the residue was treated with methyl tert-butyl ether (MTBE, 180 mL) and n-heptane (180 mL). The resulting mixture was agitated at ambient temperature for 1 hour. The solids were collected by filtration, washed with n-heptane (180 mL), and dried in the vacuum oven to the constant weight to afford the desired product, 4-chloro-7-tosyl-7H-pyrrolo[2,3-d]pyrimidine (Compound 24a, 32.1 g, 36.0 g theoretical, 89.2% yield), as off-white powders, which was used in the subsequent reactions without further purification. For 4-Chloro-7-tosyl-7H-pyrrolo[2,3-d]pyrimidine: $^1$H NMR (DMSO-$d_6$, 400 MHz) δ 8.78 (s, 1H), 8.10 (d, 2H), 7.79 (d, 1H), 7.34 (d, 2H), 6.72 (d, 1H), 2.41 (s, 3H) ppm; $C_{13}H_{10}ClN_3O_2S$ (MW, 307.75), LCMS (EI) m/e 308.1 (M$^+$+H).

Step 2. Diethyl 2-(7-tosyl-7H-pyrrolo[2,3-d]pyrimidin-4-yl)malonate (Compound 25a)

A solution of 4-chloro-7-tosyl-7H-pyrrolo[2,3-d]pyrimidine (Compound 24a, 7.0 g, 22.75 mmol) and diethyl malonate (5.46 g, 34.1 mmol, 1.5 equiv) in anhydrous DMF (30 mL) was treated with solid cesium carbonate ($Cs_2CO_3$, 18.53 g, 56.9 mmol, 2.5 equiv) at ambient temperature. The resulting reaction mixture was them warmed to 50-60° C. and agitated at 50-60° C. for 2-3 hours. When the reaction was complete, the reaction mixture was cooled to ambient temperature before being treated with water (H$_2$O, 80 mL). The quenched reaction mixture was then agitated at ambient temperature for 1 hour followed by at 0-5° C. for 1 hour. The solids were collected by filtration, washed with water (50 mL) followed by n-heptane (50 mL), and dried in the vacuum oven at 40° C. to constant weight to afford the desired product, diethyl 2-(7-tosyl-7H-pyrrolo[2,3-d]pyrimidin-4-yl)malonate (Compound 25a, 6.2 g, 9.81 g theoretical, 63.2% yield), as off-white powders, which were used in the subsequent reactions without further purification. For Diethyl 2-(7-tosyl-7H-pyrrolo[2,3-d]pyrimidin-4-yl)malonate: $^1$H NMR (CDCl$_3$, 400 MHz) δ 8.98 (s, 1H), 8.12 (d, 2H), 7.77 (d, 1H), 7.34 (d, 2H), 6.72 (d, 1H), 5.10 (s, 1H), 4.25 (m, 4H), 2.42 (s, 3H), 1.27 (m, 6H) ppm; C$_{20}$H$_{21}$N$_3$O$_6$S (MW, 431.46), LCMS (EI) m/e 432.3 (M$^+$+H).

Step 3. Ethyl 2-(7-tosyl-7H-pyrrolo[2,3-d]pyrimidin-4-yl)acetate (Compound 26a)

A solution of diethyl 2-(7-tosyl-7H-pyrrolo[2,3-d]pyrimidin-4-yl)malonate (Compound 25a, 4.0 g, 9.27 mmol) in ethanol (EtOH, 20 mL) was treated with a solution of 21% sodium ethoxide in ethanol (NaOEt, 21 wt %, 0.30 g, 0.927 mmol, 0.10 equiv) at ambient temperature and the resulting reaction mixture was agitated at ambient temperature for 12 hours. The reaction mixture was quenched with a 0.1 N aqueous hydrochloric acid solution (10 mL) and the resulting mixture was concentrated under the reduced pressure. The residue was then purified by the silica gel (SiO$_2$) column chromatography to afford the desired product, ethyl 2-(7-tosyl-7H-pyrrolo[2,3-d]pyrimidin-4-yl)acetate (Compound 26a, 2.08 g, 3.33 g theoretical, 62.6% yield), as off-white powders, which were used in the subsequent reaction without further purification. For Ethyl 2-(7-tosyl-7H-pyrrolo[2,3-d]pyrimidin-4-yl)acetate: $^1$H NMR (CDCl$_3$, 400 MHz) δ 8.96 (s, 1H), 8.11 (d, 2H), 7.75 (d, 1H), 7.33 (d, 2H), 6.70 (d, 1H), 4.19 (q, 2H), 4.30 (s, 2H), 2.41 (s, 3H), 1.25 (t, 3H) ppm; C$_{17}$H$_{17}$N$_3$O$_4$S (MW, 359.40), LCMS (EI) m/e 360.2 (M$^+$+H).

Step 4. Ethyl 2-(7H-pyrrolo[2,3-d]pyrimidin-4-yl) acetate (Compound 27a)

A solution of diethyl 2-(7-tosyl-7H-pyrrolo[2,3-d]pyrimidin-4-yl)malonate (Compound 25a, 4.0 g, 9.27 mmol) in ethanol (EtOH, 20 mL) was treated with a solution of 21% sodium ethoxide in ethanol (NaOEt, 21 wt %, 3.0 g, 9.27 mmol, 1.0 equiv) at ambient temperature. The resulting reaction mixture was heated to 65-75° C. and agitated at 65-75° C. for 12 hours. The reaction mixture was quenched with a 1.0 N aqueous hydrochloric acid solution and the resulting mixture was concentrated under the reduced pressure. The residue was then purified by the silica gel (SiO$_2$) column chromatography to afford the desired product, ethyl 2-(7H-pyrrolo[2,3-d]pyrimidin-4-yl)acetate (Compound 27a, 1.3 g, 1.9 g theoretical, 68.3% yield), as off-white powders, which were used in the subsequent reactions without further purification. For Ethyl 2-(7H-pyrrolo[2,3-d] pyrimidin-4-yl)acetate: $^1$H NMR (CDCl$_3$, 400 MHz) δ 11.40 (br s, 1H), 8.90 (s, 1H), 7.42 (d, 1H), 6.65 (d, 1H), 4.23 (q, 2H), 4.13 (s, 2H), 1.27 (t, 3H) ppm; C$_{10}$H$_{11}$N$_3$O$_2$ (MW, 205.22), LCMS (EI) m/e 206.2 (M$^+$+H).

Step 5. Sodium 2-(7H-pyrrolo[2,3-d]pyrimidin-4-yl) acetate (Compound 5b)

A solution of ethyl 2-(7H-pyrrolo[2,3-d]pyrimidin-4-yl) acetate (Compound 27a, 1.2 g, 5.85 mmol) in acetone (10 mL) and THF (10 mL) was treated with an aqueous solution of 6 N sodium hydroxide (6 N NaOH, 1.462 mL, 8.77 mmol, 1.5 equiv) at ambient temperature. The resulting reaction mixture was agitated at ambient temperature for 5 hours. The solids were collected by filtration and the isolated solids were suspended in methanol (MeOH, 4.0 mL). The resulting suspension was then added acetone (15 mL) and the mixture was agitated at ambient temperature for 1 hour. The solids were collected by filtration, washed with acetone (2×5 mL), and dried under vacuum to afford the desired product, sodium 2-(7H-pyrrolo[2,3-d]pyrimidin-4-yl)acetate (Compound 5b, 1.1 g, 1.164 g theoretical, 94.5% yield), as off-white powders, which was used in the subsequent reaction without further purification. For Sodium 2-(7H-pyrrolo [2,3-d]pyrimidin-4-yl)acetate: $^1$H NMR (DMSO-d$_6$, 400 MHz) δ 8.36 (s, 1H), 7.37 (d, 1H), 6.40 (d, 1H), 3.61 (s, 2H) ppm; C$_8$H$_6$N$_3$NaO$_2$ (MW, 199.15; C$_8$H$_7$N$_3$O$_2$ for the corresponding acid, MW 177.16), LCMS (EI) m/e 178.1 (M$^+$+H).

Step 6. 2-(7H-Pyrrolo[2,3-d]pyrimidin-4-yl)acetic Acid (Compound 5a)

A solution of ethyl 2-(7H-pyrrolo[2,3-d]pyrimidin-4-yl) acetate (Compound 27a, 1.2 g, 5.85 mmol) in acetone (10 mL) and THF (10 mL) was treated with an aqueous solution of 6 N sodium hydroxide (6 N NaOH, 1.462 mL, 8.77 mmol, 1.5 equiv) at ambient temperature. The resulting reaction mixture was agitated at ambient temperature for 5 hours. The reaction mixture was then treated with a solution of 1 N aqueous hydrochloric acid (1 N HCl, 9.0 mL) before being concentrated under the reduced pressure. The residue was then purified by the silica gel (SiO$_2$) column chromatography to afford the desired product, 2-(7H-pyrrolo[2,3-d] pyrimidin-4-yl)acetic acid (Compound 5a, 0.83 g, 1.04 g theoretical, 79.8% yield), as off-white solids, which were used in the subsequent reaction without further purification. For 2-(7H-pyrrolo[2,3-d]pyrimidin-4-yl)acetic acid: $^1$H NMR (DMSO-d$_6$, 400 MHz) δ 12.01 (br s, 1H), 8.56 (s, 1H), 7.36 (d, 1H), 6.57 (d, 1H), 3.66 (s, 2H) ppm; C$_8$H$_7$N$_3$O$_2$ (MW, 177.16), LCMS (EI) m/e 178.1 (M$^+$+H).

Example 15. Preparation of 2-(3-(4-(7H-Pyrrolo[2, 3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile Adipic Acid Salt

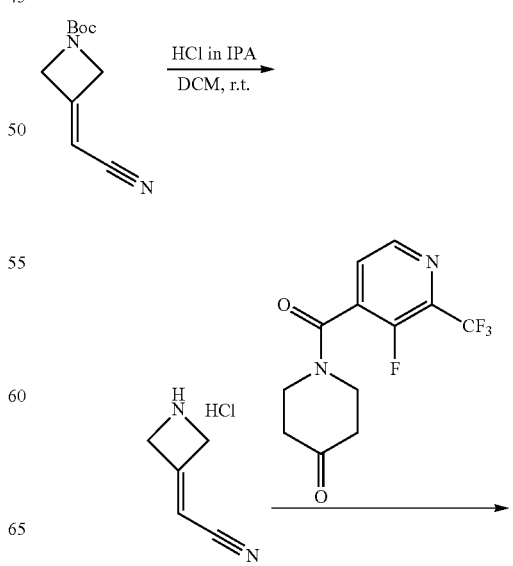

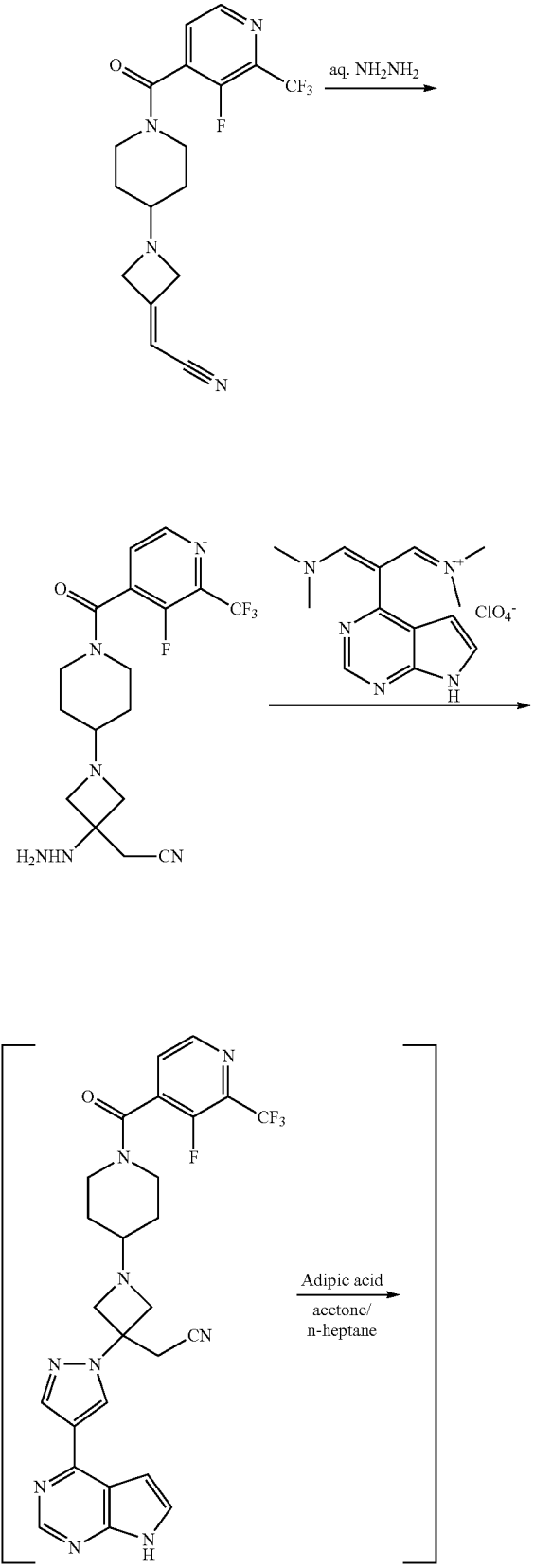

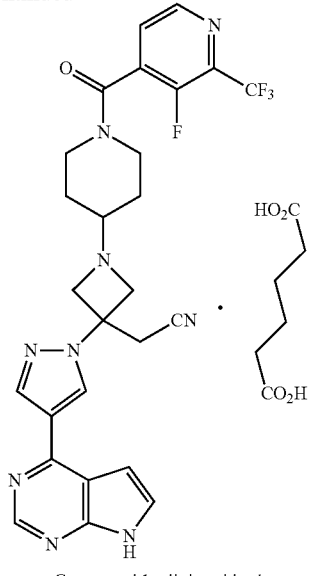

Compound 1 adipic acid salt

Step 1. 2-(Azetidin-3-ylidene)acetonitrile Hydrochloride

To a 0.5 L flask equipped with a nitrogen inlet, a thermocouple, and a mechanical stirrer were added tert-butyl 3-(cyanomethylene)azetidine-1-carboxylate (30 g, 154.46 mmol) and methylenechloride (300 mL) at ambient temperature. The solution was then treated with a solution of 5 M hydrogen chloride (HCl) in isopropanol solution (294.2 mL, 1.54 mol, 10 equiv) at ambient temperature and the resulting reaction mixture was stirred at ambient temperature for 18 hours. After the reaction was complete as monitored by HPLC, the suspension was added tert-butyl methyl ether (TBME, 150 mL), and the mixture was stirred at ambient temperature for 2 hours. The solids was collected by filtration, washed with n-heptane (2×100 mL), and dried on the filtration funnel at ambient temperature for 3 hours to afford 2-(azetidin-3-ylidene)acetonitrile hydrochloride (13.7 g, 20.2 g theoretical, 67.8%) as a white solid. $^1$H NMR (500 MHz, DMSO-$d_6$) δ 9.99 (s, 2H), 5.94 (p, J=2.5 Hz, 1H), 4.85-4.80 (m, 2H), 4.77-4.71 (m, 2H) ppm; $^{13}$C NMR (126 MHz, DMSO-$d_6$) δ 155.65, 114.54, 94.78, 55.26, 54.63 ppm; $C_5H_7ClN_2$ (MW 130.58; $C_5H_6N_2$ for free base, MW 94.11), LCMS (EI) m/e 95 (M$^+$+H).

Step 2. 2-(1-(1-(3-Fluoro-2-(trifluoromethyl)isonicotinoyl)piperidin-4-yl)azetidin-3-ylidene)acetonitrile To a 0.25 L flask equipped with a nitrogen inlet, a thermocouple, and a magnetic stirrer were added 2-(azetidin-3-ylidene)acetonitrile hydrochloride (4.5 g, 34.46 mmol), 1-(3-fluoro-2-(trifluoromethyl)isonicotinoyl)piperidin-4-one (10 g, 34.46 mmol, 1.0 equiv), and methylenechloride (100 mL) at ambient temperature and the resulting mixture was then treated with sodium triacetoxyborohydride (14.6 g, 68.93 mmol, 2.0 equiv) at ambient temperature. The reaction mixture was stirred at ambient temperature for 2 hours before being quenched with saturated sodium bicarbonate (NaHCO$_3$) aqueous solution (50 mL). The two phases were separated and the aqueous phase was extracted with dichloromethane (200 mL). The combined organic phase was washed with water (50 mL) and brine (50 mL) and concentrated under reduced pressure to afford the crude desired product, which was purified by column chromatography (SiO$_2$, 0-10% of ethyl acetate in hexane gradient elution) to afford 2-(1-(1-(3-fluoro-2-(trifluoromethyl)isonicotinoyl)piperidin-4-yl)azetidin-3-ylidene)acetonitrile (9.5 g, 12.7 g theoretical, 74.8%) as a white solid. $^1$H NMR (400 MHz, CDCl$_3$) δ 8.57 (d, J=4.7 Hz, 1H), 7.54 (t, J=4.6 Hz, 1H), 5.29 (p, J=2.4 Hz, 1H), 4.18-4.08 (m, 1H), 4.08-4.03 (m, 2H), 3.98-3.94 (m, 2H), 3.57-3.39 (m, 2H), 3.17-3.04 (m, 1H), 2.56 (tt, J=7.4, 3.5 Hz, 1H), 1.86-1.77 (m, 1H), 1.75-1.64 (m, 1H), 1.54-1.43 (m, 1H), 1.43-1.31 (m, 1H) ppm; $^{13}$C NMR (101 MHz, CDCl$_3$) δ 161.34, 160.73, 152.62 (d, J=269.1 Hz), 145.75 (d, J=6.1 Hz), 136.73 (qd, J=36.1, 12.0 Hz), 134.56 (d, J=16.9 Hz), 126.89, 120.58 (qd, J=275.0, 4.9 Hz), 115.11, 92.04, 62.05, 60.57 (2C), 44.47, 39.42, 29.38, 28.47 ppm; C$_{17}$H$_{16}$F$_4$N$_4$O (MW 368.33), LCMS (EI) m/e 369 (M$^+$+H).

Step 3. 2-(1-(1-(3-Fluoro-2-(trifluoromethyl)isonicotinoyl)piperidin-4-yl)-3-hydrazineylazetidin-3-yl)acetonitrile To a flask under nitrogen was charged 2-(1-(1-(3-fluoro-2-(trifluoromethyl)isonicotinoyl)piperidin-4-yl)azetidin-3-ylidene)acetonitrile (1.2 g, 3.26 mmol, 1.0 equiv) and acetonitrile (10 mL). Hydrazine hydrate (0.40 g, 6.84 mmol, 2.1 equiv) was slowly added to the reaction mixture over 30 minutes with reaction temperature controlled below 25° C. The reaction was completed after stirring at ambient temperature for 5 hours. Upon completion, the reaction solvent was evaporated in vacuo. The residual reaction mixture was diluted by DCM (10 mL) and washed by brine (5 mL). The organic layer was separated and collected. The aqueous layer was extracted by another portion of DCM (10 mL), and the organic layer was collected. The combined organic layer was evaporated in vacuo. The crude desired product, 2-(1-(1-(3-fluoro-2-(trifluoromethyl)isonicotinoyl)piperidin-4-yl)-3-hydrazineylazetidin-3-yl)acetonitrile (0.52 g, 37%), was obtained as a light yellow gel, which was directly used in the next step without further purification. $^1$H NMR (DMSO-d$_6$, 400 MHz) δ 8.66 (d, J=4.7 Hz, 1H), 7.89 (t, J=4.7 Hz, 1H), 4.10-3.99 (m, 1H), 3.91 (s, 1H), 3.52-3.20 (m, 4H), 3.11-2.94 (m, 5H), 2.90 (s, 2H), 2.38 (dt, J=8.2, 4.6 Hz, 1H), 1.76-1.64 (m, 1H), 1.63-1.51 (m, 1H), 1.35-1.01 (m, 2H) ppm; $^{13}$C NMR (DMSO-d$_6$, 101 MHz) δ 160.20, 152.13 (153.45, 150.81), 146.22 (146.25, 146.19), 134.70 (134.79, 134.62), 127.53, 120.60 (121.99, 121.94, 119.28, 119.26), 118.98, 61.41, 58.75, 55.83, 44.20, 28.84, 28.08, 24.28 ppm, only peaks visible; C$_{17}$H$_{20}$F$_4$N$_6$O (MW 400.38), LCMS (EI) m/e 401.3 (M$^+$+H), 423.3 (M$^+$+Na).

Step 4. 2-(3-(4-(7H-Pyrrolo[2,3-c]pyrimidin-4-yl)-1H-pyrazol-1-yl)-1-(1-(3-fluoro-2-(trifluoromethyl)isonicotinoyl)piperidin-4-yl)azetidin-3-yl)acetonitrile To a solution of 2-(1-(1-(3-fluoro-2-(trifluoromethyl)isonicotinoyl)piperidin-4-yl)-3-hydrazineylazetidin-3-yl)acetonitrile (0.606 g, 1.51 mmol, 1.30 equiv) in ethanol (3 mL) was added vinamidinium perchlorate (0.40 g, 1.16 mmol) in one portion. The resulting reaction mixture was stirred at ambient temperature for 16 hours. Upon completion, the reaction solvent was evaporated in vacuo. The residual reaction mixture was diluted by DCM (10 ml) and washed by brine (5 mL). The organic layer was separated and collected. The aqueous layer was extracted by another portion of DCM (10 mL), and the combined organic layer was evaporated in vacuo. The crude desired product, 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile (0.58 g, 95%) was obtained as a yellow gel, which was directly used in the next salt formation step without further purification. The free base obtained by this synthetic method is identical in every comparable aspect with the compound obtained by the previously reported synthetic methods (see e.g. U.S. Publication No.: 2011/0224190, the disclosure of which is incorporated herein by reference in its entirety). $^1$H NMR (400 MHz, DMSO-d$_6$) δ 12.17 (d, J=2.8 Hz, 1H), 8.85 (s, 1H), 8.70 (m, 2H), 8.45 (s, 1H), 7.93 (t, J=4.7 Hz, 1H), 7.63 (dd, J=3.6, 2.3 Hz, 1H), 7.09 (dd, J=3.6, 1.7 Hz, 1H), 4.10 (m, 1H), 3.78 (d, J=7.9 Hz, 2H), 3.61 (t, J=7.9 Hz, 1H), 3.58 (s, 2H), 3.46 (m, 1H), 3.28 (t, J=10.5 Hz, 1H), 3.09 (ddd, J=13.2, 9.5, 3.1 Hz, 1H), 2.58 (m, 1H), 1.83-1.75 (m, 1H), 1.70-1.63 (m, 1H), 1.35-1.21 (m, 2H) ppm; $^{13}$C NMR (101 MHz, DMSO-d$_6$) δ 160.28, (153.51, 150.86), 152.20, 150.94, 149.62, (146.30, 146.25), 139.48, (134.78, 134.61), (135.04, 134.92, 134.72, 134.60, 134.38, 134.26, 134.03, 133.92), 129.22, 127.62, 126.84, 121.99, 122.04, (124.77, 122.02, 119.19, 116.52), 117.39, 113.00, 99.99, 61.47, 60.49, 57.05, 44.23, 28.62, 27.88, 27.19 ppm; C$_{26}$H$_{23}$F$_4$N$_9$O (MW, 553.51), LCMS (EI) m/e 554.1 (M$^+$+H).

Step 5. 2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile Adipic Acid Salt To a 0.5 L flask equipped with a mechanical stirrer, a thermocouple, an addition funnel, and a nitrogen inlet was added a solution of crude 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile (31.38 g, 56.7 mmol) in acetone (220 mL) and adipic acid (8.7 g, 59.53 mmol, 1.05 equiv) at ambient temperature. The reaction mixture was then heated to reflux to give a solution. n-Heptane (220 mL) was gradually added to the reaction mixture at 40-50° C. in one hour. The resulting mixture was gradually cooled to ambient temperature in one hour and stirred at ambient temperature for an additional 16 hours. The solids were collected by filtration, washed with n-heptane (2×60 mL), and dried under vacuum at 50° C. with nitrogen sweeping to constant weight to afford 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile adipic acid salt (34.0 g, 39.7 g theoretical, 85.6% for two steps) as a white to off-white solid. $^1$H NMR (400 MHz, DMSO-d$_6$) δ 12.16 (s, 1H), 12.05 (brs, 2H), 8.85 (s, 1H), 8.72 (s, 1H), 8.69 (d, J=4.7 Hz, 1H), 8.45 (s, 1H), 7.93 (t, J=4.7 Hz, 1H), 7.63 (dd, J=3.6, 2.3 Hz, 1H), 7.09 (dd, J=3.6, 1.7 Hz, 1H), δ 4.11 (dt, J=11.0, 4.4 Hz, 1H), 3.77 (d, J=7.8 Hz, 2H), 3.60 (t, J=7.8 Hz, 2H), 3.58 (s, 2H), 3.44 (dt, J=14.4, 4.6 Hz, 1H), 3.28 (t, J=10.4 Hz, 1H), 3.09 (ddd, J=13.2, 9.6, 3.2 Hz, 1H), 2.58 (tt, J=8.6, 3.5 Hz, 1H), 2.28-2.17 (m, 4H), 1.83-1.74 (m, 1H), 1.67 (d, J=11.0 Hz, 1H), 1.59-1.46 (m, 4H), 1.37-1.21 (m, 2H) ppm; $^{13}$C NMR (101 MHz, DMSO-d$_6$) δ 174.38, 160.29, (153.52, 150.87), 152.20, 150.94, 149.63, (146.30, 146.25), 139.48, (134.79, 134.62), (135.08, 134.97, 134.74, 134.62, 134.38, 134.24, 134.04, 133.93), 129.21, 127.62, 126.84, 122.05, (124.75, 122.02, 119.29, 116.54), 117.39, 113.01, 99.99, 61.47, 60.50, 57.06, 44.24, 33.42, 30.70, 28.63, 27.89, 27.20, 24.07 ppm; $C_{32}H_{33}F_4N_9O_5$ (MW 699.66; $C_{26}H_{23}F_4N_9O$ for free base, MW, 553.51), LCMS (EI) m/e 554.0 (M$^+$+H).

Example 16. Alternative Preparation of 2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile Adipic Acid Salt

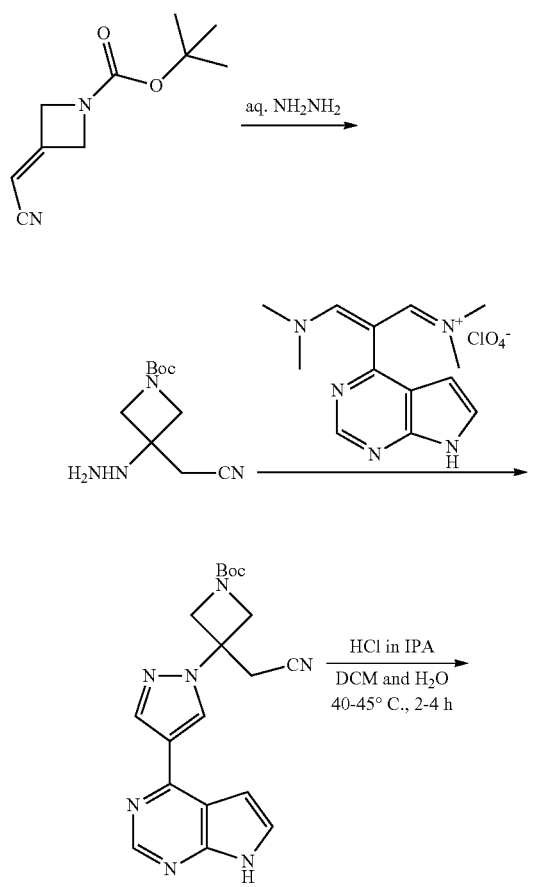

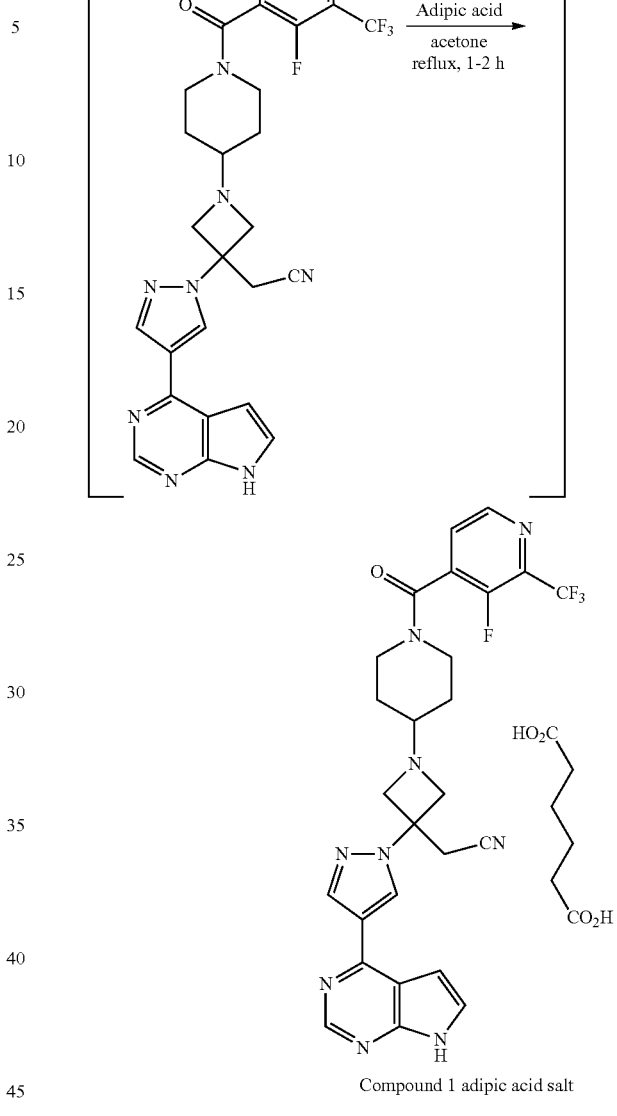

Compound 1 adipic acid salt

Step 1. tert-Butyl 3-(cyanomethyl)-3-hydrazineylazetidine-1-carboxylate

To a reaction vial under nitrogen was charged tert-butyl 3-(cyanomethylene)azetidine-1-carboxylate-3-ylidene)acetonitrile (2.0 g, 10.3 mmol, 1.0 equiv) and acetonitrile (10 mL). Hydrazine hydrate (1.26 g, 21.6 mmol, 2.1 equiv) was slowly added to the reaction mixture over 20 minutes with reaction temperature controlled below 25° C. The reaction was completed after stirring at ambient temperature for 1 hour. Upon completion, the reaction solvent was evaporated in vacuo. The residual reaction mixture was diluted by DCM (10 mL) and washed by brine (5 mL). The organic layer was separated and collected. The aqueous layer was extracted by another portion of DCM (10 mL), and the combined organic layer was evaporated in vacuo. The crude desired product, tert-butyl 3-(cyanomethyl)-3-hydrazineylazetidine-1-carboxylate (INCB125078, 2.40 g, 95%), was obtained as a white solid, which was directly used in the next step without

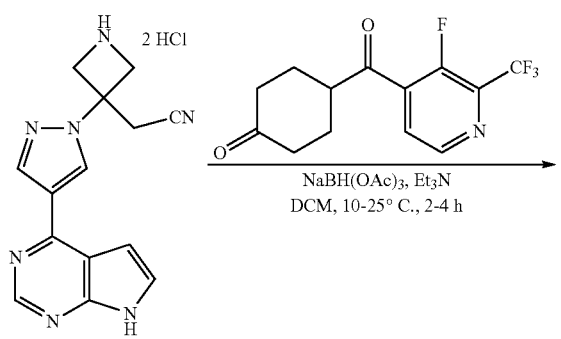

further purification. For INCB125078: $^1$H NMR (CDCl$_3$, 400 MHz) δ 3.80 (q, J=9.4 Hz, 4H), 3.17 (br, 3H), 2.90 (s, 2H), 1.43 (s, 9H) ppm; $^{13}$C NMR (CDCl$_3$, 101 MHz) δ 156.40, 117.19, 80.34, 57.09, 56.07, 28.46, 24.82 ppm; C$_{10}$H$_{18}$N$_4$O$_2$ (MW 226.28), LCMS (EI) m/e 227.3 (M$^+$+H).

Step 2. tert-butyl 3-(4-(7H-Pyrrolo[2,3-d]pyrimidin-4-yl)-1H-pyrazol-1-yl)-3-(cyanomethyl)azetidine-1-carboxylate To a solution of tert-butyl 3-(cyanomethyl)-3-hydrazineylazetidine-1-carboxylate (2.40 g, 10.59 mmol, 1.30 equiv) in ethanol (20 mL) was added vinamidinium perchlorate (INCB122809 perchlorate, 2.80 g, 8.15 mmol) in one portion. The resulting reaction mixture was stirred at ambient temperature for 4 hours. Upon completion, the reaction mixture was added n-heptane (10 mL) and stirred at ambient temperature for another 1 hour. The reaction mixture was filtered and the solid was washed by n-heptane (10 mL). After drying overnight night by pulling air through the wet cake, the crude desired product, tert-butyl 3-(4-(7H-pyrrolo[2,3-d]pyrimidin-4-yl)-1H-pyrazol-1-yl)-3-(cyanomethyl)azetidine-1-carboxylate (3.10 g, 95%), was obtained as a brown solid, which was directly used in the next step without further purification. $^1$H NMR (CDCl$_3$, 400 MHz) δ 10.54 (s, 1H), 8.85 (s, 1H), 8.48 (s, 1H), 8.35 (s, 1H), 7.44 (d, J=3.4 Hz, 1H), 6.79 (d, J=3.5 Hz, 1H), 4.55 (d, J=9.7 Hz, 2H), 4.30 (d, J=9.7 Hz, 2H), 3.34 (s, 2H), 1.47 (s, 9H) ppm; $^{13}$C NMR (CDCl$_3$, 101 MHz) δ 156.00, 152.55, 151.37, 150.40, 140.94, 128.55, 126.06, 123.05, 115.41, 114.34, 100.67, 81.33, 59.00, 56.99, 28.42, 28.25 ppm; C$_{19}$H$_{21}$N$_7$O$_2$ (MW 379.42), LCMS (EI) m/e 380.4 (M$^+$+H).

Step 3. 2-(3-(4-(7H-Pyrrolo[2,3-d]pyrimidin-4-yl)-1H-pyrazol-1-yl)azetidin-3-yl)acetonitrile Dihydrochloride Salt To a 0.5 L flask equipped with a nitrogen inlet, a thermocouple, an additional funnel, and a mechanical stirrer were added tert-butyl 3-(4-(7H-pyrrolo[2,3-d]pyrimidin-4-yl)-1H-pyrazol-1-yl)-3-(cyanomethyl)azetidine-1-carboxylate (15 g, 39.5 mmol), water (7.5 mL, 416 mmol) and dichloromethane (75 mL) at room temperature. The mixture was stirred at room temperature to generate a suspension. To the suspension was added a solution of 5 M hydrogen chloride (HCl) in isopropanol (55 mL, 275 mmol, 7.0 equiv) in 5 minutes. The resulting reaction mixture was then heated to gentle reflux and maintained at reflux for 3-4 hours. After the reaction was completed as monitored by HPLC, tert-butyl methyl ether (TBME, 45 mL) was added to the reaction suspension. The mixture was gradually cooled to room temperature, and stirred for an additional one hour. The solids were collected by filtration, washed with tert-butyl methyl ether (TBME, 45 mL) and dried under vacuum at 50° C. with nitrogen sweeping to constant weight to afford 2-(3-(4-(7H-pyrrolo[2,3-d]pyrimidin-4-yl)-1H-pyrazol-1-yl)azetidin-3-yl)acetonitrile dihydrochloride salt (13.6 g, 13.9 g theoretical, 98%) as an off-white to light yellow solid. $^1$H NMR (400 MHz, D$_2$O) δ 8.96 (s, 1H), 8.81 (s, 1H), 8.49 (s, 1H), 7.78 (d, J=3.8 Hz, 1H), 7.09 (d, J=3.7 Hz, 1H), 4.93 (d, J=12.8 Hz, 2H), 4.74 (d, J=12.5 Hz, 2H), 3.74 (s, 2H) ppm; $^{13}$C NMR (101 MHz, D$_2$O) δ 151.35, 143.75, 143.33, 141.33, 132.03, 131.97, 115.90, 114.54, 113.85, 103.18, 59.72, 54.45 (2C), 27.02 ppm; C$_{14}$H$_{15}$Cl$_2$N$_7$ (C$_{14}$H$_{13}$N$_7$ for free base, MW 279.30), LCMS (EI) m/e 280 (M$^+$+H).

Step 4. 2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile To a 0.5 L flask equipped with a nitrogen inlet, a thermocouple, an additional funnel, and a mechanical stirrer were added 2-(3-(4-(7H-pyrrolo[2,3-d]pyrimidin-4-yl)-1H-pyrazol-1-yl)azetidin-3-yl)acetonitrile dihydrochloride salt (20 g, 56.78 mmol), dichloromethane (200 mL), and triethylamine (TEA, 16.62 mL, 119.2 mmol, 2.1 equiv) at ambient temperature. The mixture was stirred at ambient temperature for 30 minutes before 1-(3-fluoro-2-(trifluoromethyl)-isonicotinoyl)piperidin-4-one (17.15 g, 57.91 mmol, 1.02 equiv) was added to the mixture. The mixture was then treated with sodium triacetoxyborohydride (25.34 g, 113.6 mmol, 2.0 equiv) in 5 minutes at ambient temperature (below 26° C.). The resulting reaction mixture was stirred at ambient temperature for 2 hours. After the reaction was complete as monitored by HPLC, the reaction mixture was quenched with saturated NaHCO$_3$ aqueous solution (200 mL). The two phases were separated and the aqueous phase was extracted with methylene chloride (200 mL). The combined organic phase was washed with 4% brine (100 mL) followed by solvent switch of methylene chloride to acetone by distillation. The resulting solution of the desired crude product in acetone was directly used for the subsequent adipate salt formation. A small portion of solution was purified by column chromatography (SiO$_2$, 0-10% of MeOH in EtOAc gradient elution) to afford the analytically pure 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile as an off-white solid. The 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile obtained by this synthetic method is identical in every comparable aspect with the compound obtained by Example 15 and previously reported synthetic methods (see e.g., U.S. Publication No.: 2011/0224190, the disclosure of which is incorporated herein by reference in its entirety). $^1$H NMR (400 MHz, DMSO-d$_6$) δ 12.17 (d, J=2.8 Hz, 1H), 8.85 (s, 1H), 8.70 (m, 2H), 8.45 (s, 1H), 7.93 (t, J=4.7 Hz, 1H), 7.63 (dd, J=3.6, 2.3 Hz, 1H), 7.09 (dd, J=3.6, 1.7 Hz, 1H), 4.10 (m, 1H), 3.78 (d, J=7.9 Hz, 2H), 3.61 (t, J=7.9 Hz, 1H), 3.58 (s, 2H), 3.46 (m, 1H), 3.28 (t, J=10.5 Hz, 1H), 3.09 (ddd, J=13.2, 9.5, 3.1 Hz, 1H), 2.58 (m, 1H), 1.83-1.75 (m, 1H), 1.70-1.63 (m, 1H), 1.35-1.21 (m, 2H) ppm; $^{13}$C NMR (101 MHz, DMSO-d$_6$) δ 160.28, (153.51, 150.86), 152.20, 150.94, 149.62, (146.30, 146.25), 139.48, (134.78, 134.61), (135.04, 134.92, 134.72, 134.60, 134.38, 134.26, 134.03, 133.92), 129.22, 127.62, 126.84, 121.99, 122.04, (124.77, 122.02), 119.19, 116.52), 117.39, 113.00, 99.99, 61.47, 60.49, 57.05, 44.23, 28.62, 27.88, 27.19 ppm; C$_{26}$H$_{23}$F$_4$N$_9$O (MW 553.51), LCMS (EI) m/e 554.1 (M$^+$+H).

Step 5. 2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile Adipic Acid Salt To a 0.5-L flask equipped with a mechanical stirrer, a thermocouple, an addition funnel, and a nitrogen inlet was added a solution of crude 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile (31.38 g, 56.7 mmol) in acetone (220 mL) and adipic acid (8.7 g, 59.53 mmol, 1.05 equiv) at ambient temperature. The reaction mixture was then heated to reflux to give a solution. n-Heptane (220 mL) was gradually added to the reaction mixture at 40-50° C. in one hour. The resulting mixture was gradually cooled to ambient temperature in one hour and stirred at ambient temperature for an additional 16 hours. The solids were collected by filtration, washed with n-heptane (2×60 mL), and dried under vacuum at 50° C. with nitrogen sweeping to constant weight to afford 2-(3-(4-(7H-Pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile adipic acid salt (34.0 g, 39.7 g theoretical, 85.6% for two steps) as a white to off-white solid. $^1$H NMR (400 MHz, DMSO-$d_6$) δ 12.16 (s, 1H), 12.05 (brs, 2H), 8.85 (s, 1H), 8.72 (s, 1H), 8.69 (d, J=4.7 Hz, 1H), 8.45 (s, 1H), 7.93 (t, J=4.7 Hz, 1H), 7.63 (dd, J=3.6, 2.3 Hz, 1H), 7.09 (dd, J=3.6, 1.7 Hz, 1H), δ 4.11 (dt, J=11.0, 4.4 Hz, 1H), 3.77 (d, J=7.8 Hz, 2H), 3.60 (t, J=7.8 Hz, 2H), 3.58 (s, 2H), 3.44 (dt, J=14.4, 4.6 Hz, 1H), 3.28 (t, J=10.4 Hz, 1H), 3.09 (ddd, J=13.2, 9.6, 3.2 Hz, 1H), 2.58 (tt, J=8.6, 3.5 Hz, 1H), 2.28-2.17 (m, 4H), 1.83-1.74 (m, 1H), 1.67 (d, J=11.0 Hz, 1H), 1.59-1.46 (m, 4H), 1.37-1.21 (m, 2H) ppm; $^{13}$C NMR (101 MHz, DMSO-$d_6$) δ 174.38, 160.29, (153.52, 150.87), 152.20, 150.94, 149.63, (146.30, 146.25), 139.48, (134.79, 134.62), (135.08, 134.97, 134.74, 134.62, 134.38, 134.28, 134.04, 133.93), 129.21, 127.62, 126.84, 122.05, (124.75, 122.02, 119.29, 116.54), 117.39, 113.01, 99.99, 61.47, 60.50, 57.06, 44.24, 33.42, 30.70, 28.63, 27.89, 27.20, 24.07 ppm; $C_{32}H_{33}F_4N_9O_5$ (MW 699.66; $C_{26}H_{23}F_4N_9O$ for free base, MW, 553.51), LCMS (EI) m/e 554.0 (M$^+$+H).

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A process of preparing itacitinib, or a salt thereof, comprising:
reacting a compound of formula 3:

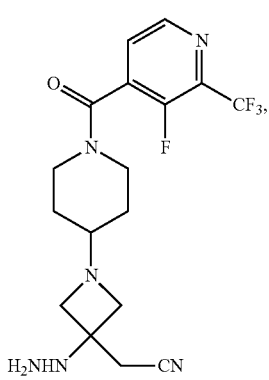

or a salt thereof, with a reagent selected from (i) a salt of formula 2a, or a salt thereof, and (ii) a compound of formula 2b:

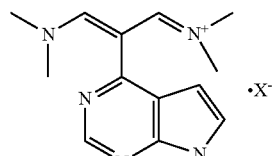

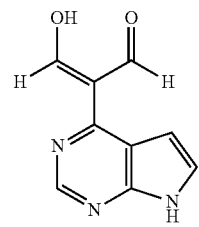

wherein X$^-$ is a counter anion.

2. A process of preparing itacitinib, or a salt thereof, comprising:
reacting a compound of formula 3:

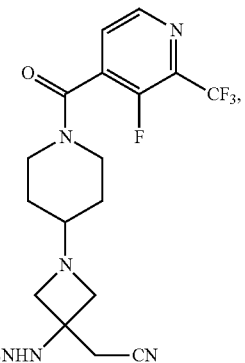

or a salt thereof, with a reagent selected from (i) a salt of formula 2a, and (ii) a compound of formula 2b:

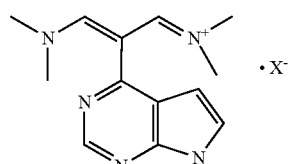

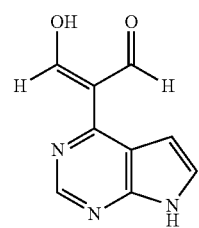

wherein X$^-$ is a counter anion.

3. The process of claim 1, wherein X$^-$ is selected from Cl$^-$, BF$_4^-$, PF$_6^-$, AsF$_6^-$, SbF$_6^-$, and ClO$_4^-$.

4. The process of claim 1, wherein X⁻ is Cl⁻.

5. The process of claim 1, wherein the reagent is the salt of formula 2a.

6. The process of claim 1, wherein the reagent is the compound of formula 2b.

7. The process of claim 1, wherein the salt of formula 2a or the compound of formula 2b is prepared by a process comprising:

reacting the compound of formula 1a:

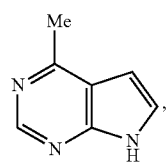

1a or a salt thereof, with a Vilsmeier reagent formed from dimethylformamide.

8. The process of claim 7, wherein the Vilsmeier reagent is prepared by a process comprising reacting dimethylformamide with a chlorinating agent.

9. The process of claim 8, wherein the chlorinating agent is selected from oxalyl chloride, phosphorus oxychloride, and triphosgene.

10. The process of claim 8, wherein the chlorinating agent is oxalyl chloride.

11. The process of claim 7, wherein the product of the reacting with the Vilsmeier reagent has formula 2d:

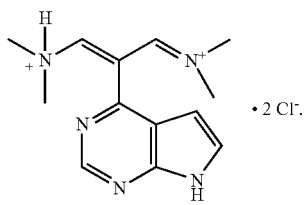

2d

12. The process of claim 11, wherein further comprising reacting a salt of formula 2d:

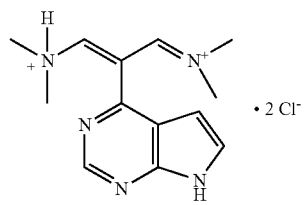

2d with a base to form a salt of formula 2c:

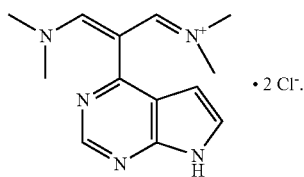

2c

13. The process of claim 7, wherein the reacting with the Vilsmeier reagent produces a salt of formula 2c:

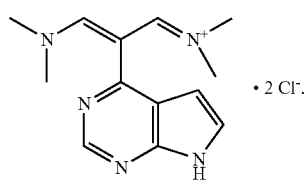

2c

14. The process of claim 12, further comprising:
reacting the salt of formula 2c:

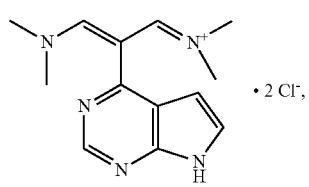

2c with a salt of formula M⁺X⁻ to form the salt of formula 2a, wherein:
M⁺ is a counter cation; and
X⁻ is a counter anion other than Cl⁻.

15. The process of claim 12, wherein the compound of formula 2b is prepared by a process comprising reacting the salt of formula 2a or the salt of formula 2c with a base to form the compound of formula 2b.

16. The process of claim 7, wherein the compound of formula 1a, or the salt thereof, is prepared by a process comprising:
deprotecting a compound of formula 1aP:

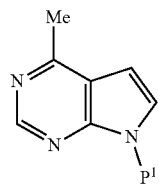

1aP wherein P¹ is an amino protecting group.

17. The process of claim 16, wherein P¹ is selected from (R¹)₃Si, wherein R¹ is $C_{1-6}$ alkyl.

18. The process of claim 17, wherein R¹ is methyl, ethyl, propyl, isopropyl, butyl or t-butyl.

19. The process of claim 16, wherein the compound of formula 1aP is prepared by a process comprising:
reacting a compound of formula 2P:

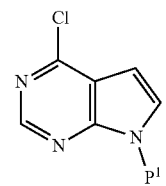

2P with MeMgBr in the presence of a Grignard catalyst, wherein P¹ is an amino protecting group.

20. The process of claim 19, wherein the compound of formula 2P is prepared by a process comprising:
protecting a compound of formula 12a:

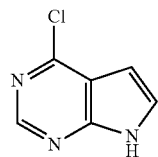

12a to form the compound of formula 2P.

21. The process of claim 20, wherein the protecting comprises reacting the compound of formula 12a with an alkali metal hydride and P¹—Y, wherein Y is halo.

22. The process of claim 21, wherein P¹—Y is $(R^1)_3Si$—Y, wherein Y is halo and $R^1$ is $C_{1-6}$ alkyl.

23. The process of claim 20, wherein the compound of formula 12a is prepared by a process comprising:
reacting a compound of formula 11a:

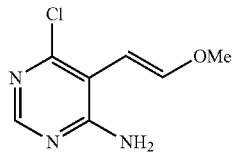

11a or a salt thereof, with a strong acid.

24. The process of claim 23, wherein the compound of formula 11a, or a salt thereof, is prepared by a process comprising:
reacting a compound of formula 10a:

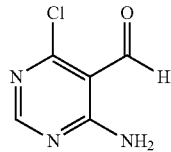

10a or a salt thereof, with (methoxymethyl)triphenylphosphonium chloride and a base.

25. The process of claim 24, wherein the compound of formula 10a, or a salt thereof, is prepared by a process comprising:
reacting a compound of formula 9a:

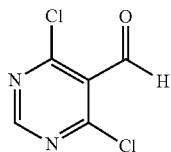

9a with ammonia.

26. The process of claim 25, wherein the compound of formula 9a is prepared by a process comprising:
reacting a compound of formula 8a:

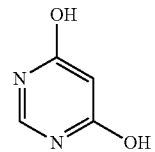

8a with a Vilsmeier reagent formed from dimethylformamide.

27. The process of claim 26, wherein the Vilsmeier reagent is prepared by a process comprising reacting dimethylformamide with a chlorinating agent.

28. The process of claim 20, wherein the compound of formula 12a is prepared by a process comprising:
reacting a compound of formula 15a:

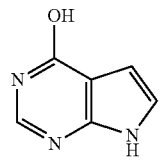

15a with a chlorinating agent.

29. The process of claim 28, wherein the compound of formula 15a is prepared by a process comprising:
reacting a compound of formula 14a:

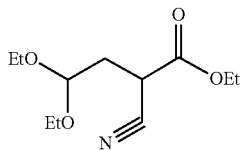

14a with formamidine acetate and an alkali metal hydroxide to generate a compound of formula 14aa:

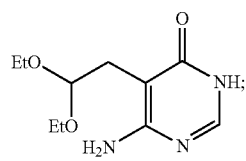

14aa and reacting the compound of formula 14aa with a strong acid.

30. The process of claim 29, wherein the compound of formula 14a is prepared by a process comprising:

reacting a compound of formula 13a:

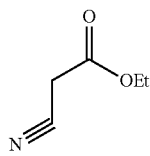

13a with bromoacetaldehyde diethyl acetal and sodium tert-amyloxide.

31. The process of claim 7, wherein the compound of formula 1a, or the salt thereof, is prepared by a process comprising:
reducing a compound of formula 23P:

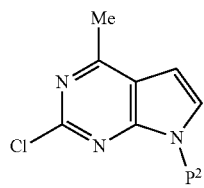

23P wherein P² is an amino protecting group.

32. The process of claim 31, wherein the reducing of the compound of formula 23P is accomplished by a process comprising reacting the compound of formula 23P with hydrogen gas in the presence of a catalyst.

33. The process of claim 31, wherein the compound of formula 23P is prepared by a process comprising:
reacting a compound of formula 22P:

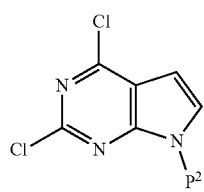

22P with MeMgBr in the presence of a Grignard catalyst, wherein P² is an amino protecting group.

34. The process of claim 33, wherein the compound of formula 22P is prepared by a process comprising:
protecting a compound of formula 22a:

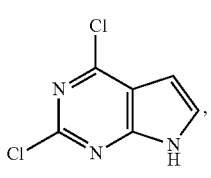

22a to form the compound of formula 22P.

35. The process of claim 34, wherein the protecting comprise reacting the compound of formula 22a with an alkali metal hydride and P²—Y, wherein Y is halo.

36. The process of claim 35, wherein P² is (R¹)₃ Si, wherein R¹ is $C_{1-6}$ alkyl.

37. The process of claim 7, wherein the compound of formula 1a, or the salt thereof, is prepared by a process comprising:
reacting a compound of formula 18a:

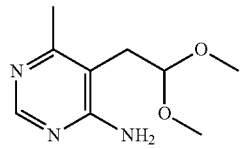

18a or a salt thereof, with an acid to form the compound of formula 1a.

38. The process of claim 37, wherein the compound of formula 18a, or a salt thereof, is prepared by a process comprising:
reacting a compound of formula 17a:

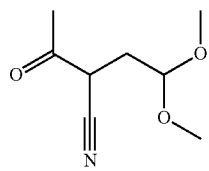

17a or a salt thereof, with formamidine acetate and triethyl orthoformate to form the compound of formula 18a, or a salt thereof.

39. The process of claim 38, wherein the compound of formula 17a, or a salt thereof, is prepared by a process comprising:
reacting a compound of formula 20a:

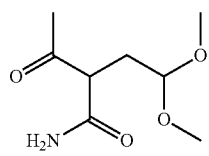

20a or a salt thereof, with a compound of formula 21a:

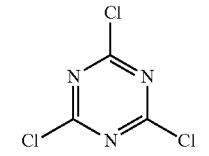

21a to form the compound of formula 17a, or a salt thereof.

40. The process of claim 39, wherein the compound of formula 20a, or a salt thereof, is prepared by a process comprising:

reacting a compound of formula 19a:

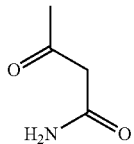
19a with bromo-1,1-dimethoxyethane and a base to form the compound of formula 20a.

41. The process of claim 40, wherein the base is an alkali metal carbonate.

42. The process of claim 38, wherein the compound of formula 17a, or a salt thereof, is prepared by a process comprising:

reacting a compound of formula 16a:

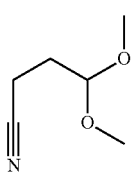
16a with ethyl acetate and a base to form the compound of formula 17a, or a salt thereof.

43. The process of claim 42, wherein the base is an alkali metal alkoxide.

44. The process of claim 2, wherein the salt of formula 2a or the compound of formula 2b is prepared by a process comprising:

reacting the compound of formula 5a:

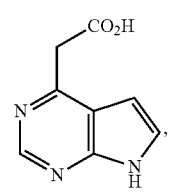
5a or a salt thereof, with a Vilsmeier reagent formed from dimethylformamide.

45. The process of claim 44, wherein the Vilsmeier reagent is prepared by a process comprising reacting dimethylformamide with a chlorinating agent.

46. The process of claim 45, wherein the chlorinating agent is selected from oxalyl chloride, phosphorus oxychloride, and triphosgene.

47. The process of claim 45, wherein the chlorinating agent is oxalyl chloride.

48. The process of claim 44, wherein the product of the reacting with the Vilsmeier reagent has formula 2d:

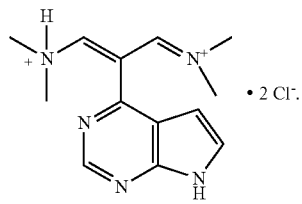
2d

49. The process of claim 48, further comprising reacting the salt of formula 2d:

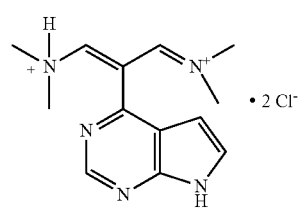
2d with a base to form a salt of formula 2c:

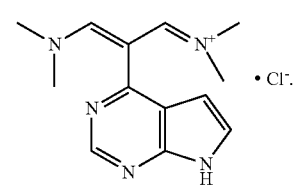
2c

50. The process of claim 44, wherein the reacting with the Vilsmeier reagent produces a compound of formula 2c:

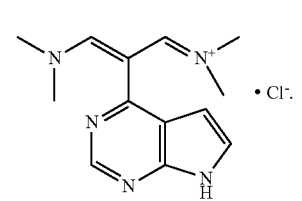
2c

51. The process of claim 49, further comprising:
reacting the salt of formula 2c:

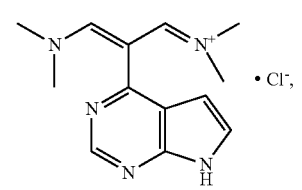
2c with a salt of formula M⁺X⁻ to form the salt of formula 2a, wherein:
M⁺ is a counter cation; and
X⁻ is a counter anion other than Cl⁻.

52. The process of claim 49, wherein the compound of formula 2b is prepared by a process comprising reacting the salt of formula 2a or the salt of formula 2c with a base to form the compound of formula 2b.

53. The process of claim 44, wherein the compound of formula or the salt thereof, is prepared by a process comprising:

hydrolyzing a compound of formula 27a:

27a in water in the presence of a base.

54. The process of claim 53, wherein the base, present for the hydrolyzing of the compound of formula 27a, is sodium hydroxide; and the compound of formula 5a, or the salt thereof, is a sodium salt of the compound of formula 5a.

55. The process of claim 54, further comprising reacting the sodium salt of the compound of formula 5a with a strong acid.

56. The process of claim 53, wherein the compound of formula 27a is prepared by a process comprising:

reacting a compound of formula 26P:

26P with a strong acid, wherein $P^1$ is an amino protecting group.

57. The process of claim 56, wherein $P^1$ is p-toluenesulfonyl.

58. The process of claim 56, wherein the compound of formula 26P is prepared by a process comprising:

reacting a compound of formula 25P:

25P with alkali metal alkoxide to form the compound of formula 26P, wherein $P^1$ is an amino protecting group.

59. The process of claim 58, wherein the compound of formula 25P is prepared by a process comprising:

reacting a compound of formula 2P:

2P with diethyl malonate and a base, wherein $P^1$ is an amino protecting group.

60. The process of claim 1, wherein the itacitinib, or the salt thereof, is itacitinib adipate.

61. The process of claim 60, wherein the itacitinib adipate is prepared by a process comprising reacting the itacitinib with at least one equivalent of adipic acid.

62. The process of claim 1, wherein the compound of formula 3, or the salt thereof, is formed by a process comprising:

reacting a compound of formula A1:

A1 with hydrazine.

63. A process of preparing itacitinib, or a salt thereof, comprising reacting a salt of formula 2c:

2c with a compound of formula 3:

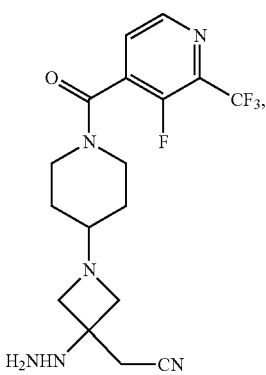

or a salt thereof, to form the itacitinib, or the salt thereof.

64. The process of claim 63, further comprising reacting the itacitinib with at least one equivalent of adipic acid.

65. The process of claim 63, wherein the itacitinib, or the salt thereof, is itacitinib adipate.

66. The process of claim 63, wherein the salt of formula 2c is prepared by a process comprising reacting a salt of formula 2d:

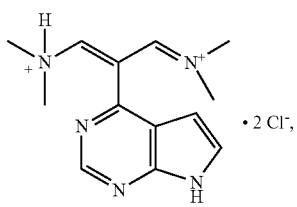

with a base to form the salt of formula 2c.

67. The process of claim 66, wherein the salt of formula 2d is prepared by a process comprising:
reacting a compound of formula 2P:

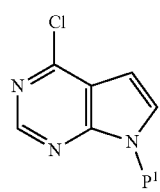

with MeMgBr in the presence of a Grignard catalyst to form a compound of formula 1aP:

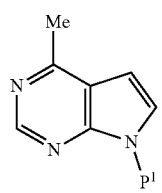

deprotecting the compound of formula 1aP to form a compound of formula 1a:

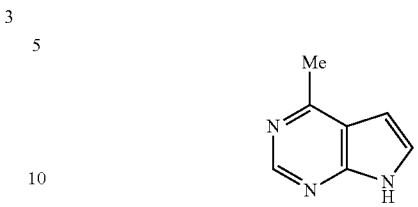

or a salt thereof; and reacting the compound of formula 1a, or the salt thereof, with a Vilsmeier reagent formed from dimethylformamide and a chlorinating agent to form the salt of formula 2d;

wherein $P^1$ is an amino protecting group.

68. The process of claim 66, wherein the salt of formula 2d is prepared by a process comprising:
reacting a compound of formula 22P:

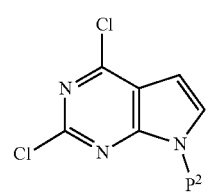

with MeMgBr in the presence of a Grignard catalyst to form a compound of formula 23P:

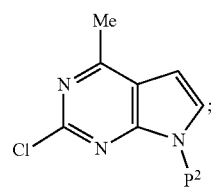

reducing the compound of formula 23P to form a compound of formula 1a:

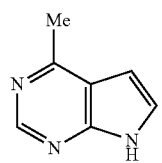

or a salt thereof; and reacting the compound of formula 1a, or the salt thereof, with a Vilsmeier reagent formed from dimethylformamide and a chlorinating agent to form the salt of formula 2d;

wherein $P^2$ is an amino protecting group.

69. A compound of formula 3, having the formula:
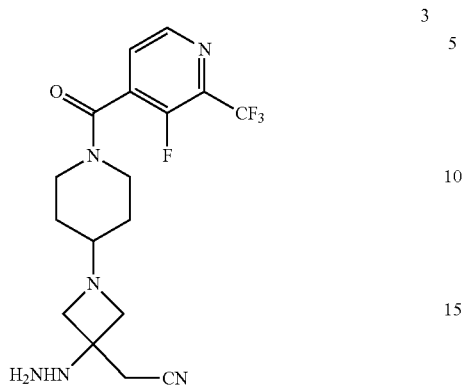
or a salt thereof.

UNITED STATES PATENT AND TRADEMARK OFFICE
CERTIFICATE OF CORRECTION

| | | |
|---|---|---|
| PATENT NO. | : 11,897,889 B2 | Page 1 of 1 |
| APPLICATION NO. | : 17/404461 | |
| DATED | : February 13, 2024 | |
| INVENTOR(S) | : Jiacheng Zhou et al. | |

It is certified that error appears in the above-identified patent and that said Letters Patent is hereby corrected as shown below:

On the Title Page

Column 2 (Other Publications), Line 2, delete "Heterocycl" and insert -- Heterocycle --.

In the Claims

Column 111, Lines 60-65, Claim 12, before "Cl$^-$" delete "2";

Column 112, Lines 5-11, Claim 13, before "Cl$^-$" delete "2";

Column 112, Lines 20-22, Claim 14, before "Cl$^-$" delete "2";

Column 115, Line 66, Claim 36, delete "($R^1$)$_3$ Si," and insert -- (R1)$_3$Si, --;

Column 117, Line 16, Claim 40, delete "20a." and insert -- 20a, or a salt thereof. --;

Column 119, Line 4, Claim 53, after "formula" insert -- 5a, --;

Column 121, Lines 32-35, Claim 66, delete "Cl$^-$," and insert -- Cl$^-$ --.

Signed and Sealed this
Fifteenth Day of October, 2024

Katherine Kelly Vidal
*Director of the United States Patent and Trademark Office*